United States Patent [19]

Töpfer et al.

[11] Patent Number: 6,133,506
[45] Date of Patent: Oct. 17, 2000

[54] **KETO-ACYL-(ACP) REDUCTASE PROMOTER FROM *CUPHEA LANCEOLATA***

[75] Inventors: Reinhard Töpfer, Bergheim; Christa Höricke-Grandpierre, Bonn; Barbara Klein; Jeff Schell, both of Cologne, all of Germany

[73] Assignee: Max-Planck-Gesellschaft zur Forerung Der Wissenschaft E.V., Munich, Germany

[21] Appl. No.: 08/617,860

[22] PCT Filed: Sep. 5, 1994

[86] PCT No.: PCT/EP94/02950

§ 371 Date: May 23, 1996

§ 102(e) Date: May 23, 1996

[87] PCT Pub. No.: WO95/07357

PCT Pub. Date: Mar. 16, 1995

[30] Foreign Application Priority Data

Sep. 4, 1993 [DE] Germany ............................ 43 29 951

[51] Int. Cl.[7] .............................. A01H 5/00; C07H 21/04; C12N 15/82
[52] U.S. Cl. ......................... 800/298; 435/468; 536/24.1; 800/278
[58] Field of Search .................................. 536/24.1, 23.2, 536/23.6; 435/172.3, 320.1, 419, 468; 800/205, 278, 298

[56] References Cited

FOREIGN PATENT DOCUMENTS

| | | | |
|---|---|---|---|
| 9218634 | 10/1992 | WIPO | C12N 15/82 |
| WO 92/18634 | 10/1992 | WIPO . | |
| 9311243 | 6/1993 | WIPO | C12N 15/51 |
| 9417188 | 8/1994 | WIPO | C12N 15/52 |
| 9423027 | 10/1994 | WIPO | C12N 15/11 |
| WO 94/23027 | 10/1994 | WIPO . | |

OTHER PUBLICATIONS

Baumlein, Helmut, et al., "Cis–analysis of a seed protein gene promoter: the conservative RY repeat CATGCATG within the legumin box is essential for tissue–specific expression of a legumin gene", *The Plant Journal*, vol. 2, No. 2, pp. 233–239 (1992).

Baumlein, Helmut, eg al., "A novel seed protein gene from *Vicia faba* is developmentally regulated in transgenic tobacco and Arabidopsis plants", *Mol. Gen. Genet*, vol. 225, pp. 459–467 (1991).

Colot, Vincent, et al., "Molecular characterization of an active wheat LMW glutenin gene and its relation to other wheat and barley prolamin genes", *Mol. Gen. Genet*, vol. 216, pp. 81–90 (1989).

de Silva, Jacqueline, et al., "The isolation and functional charaterisation of a *B.napus* acyl carrier protein 5' flanking region involved in the regulation of seed storage lipid systhesis", *Plant Molecular Biology*, vol. 18, pp. 1163–1172 (1992).

Keddie, James S., "Cloning and characterisation of an oleosin gene from *Brassica napus*", *Plant Molecular Biology*, vol. 19, pp. 443–453 (1992).

Knutzon, Deborah S., "Modification of Brassica seed oil by antisense expression of a stearoyl–acyl carrier protein desaturase gene", *Proc. Nat. Acad. Sci., USA*, vol. 89, pp. 2624–2628 (Apr. 1992).

Kondo, Hiroki, et al., "Acetyl–CoA carboxylase from *Escherichia coli*; Gene organization and nucleotide sequence of the biotin carboxylase subunit", *Proc. Natl. Acad. Sci. USA*, vol. 88, pp. 9730–9733, (Nov. 1991).

Luo, Kiaochun, et al., "Structural features of the acetyl–CoA carboxylase gene: Mechanisms for the generation of mRNAs with 5' end heterogeneity", *Proc. Natl. Acad. Sci. USA*, vol. 86, pp. 4042–4046 (1989).

Matzke, A.J.M., et al., "Deletion analysis of a zein gene promoter in transgenic tobacco plants", *Plant Molecular Biology*, vol. 14, pp. 323–332 (1990).

Robert, Laurian S., et al., "Tissue–Specific Expression of a Wheat High Molecular Weight Glutenin Gene in Transgenic Tobacco", *The Plant Cell*, vol. 1, pp. 569–578 (Jun. 1989).

Scherer, Donna E., et al., "Isolation of a cDNA clone for the acyl carrier protein–I of spinach", *Plant Molecular Biology*, vol. 9, pp. 127–134 (1987).

Stayton, Mark, et al., "High Level, Seed–specific Expression of Foreign Coding Sequences in *Brassica napus*", *Aust. J. Plant Physiol.*, vol. 18, pp. 507–517 (1991).

Egli, Margaret A., et al., (Abstract 384), "Cloning and Sequence Analysis of a Maize Acetyl–CoA Caroxylase Gene", *Supplement to Plant Physiology* (*Annual Meeting of the American Society of Plant Physiologists*), vol. 102, p. 70 (1993).

Yanai, Yukihiro, et al., (Abstract 382), "RFLP Mapping of an Arabidopsis Acetyl–CoA Carboxylase Gene", *Supplement to Plant Physiology* (*Annual Meeting of the American Society of Plant Physiologists*), vol. 102, p. 70 (1993).

Slabas, A. R., et al., (Abstract 119: 221570p) "Biochemistry and molecular biology of lipid biosynthesis in plants: potential for genetic manipulation", *Plant Biochem*, vol. 119, p. 557 (1993).

Schulte, et al., (Abstract Y 315), "Strategies for the isolation of genes involved in de novo fatty acid biosynthesis", *J. Cell. Supp., Crop Improvement via Biotechnology: An International Perspective* (Keystone Symposia on Molecular & Cellular Biology), p. 227, Supplement 16F, Apr. 3–16 1992.

Klein et al., Isolation and Characterization of a cDNA from *Cuphea lanceolata* encoding a Beta–Ketoacyl–ACP Reductase, Mol. Gen. Genet. (1992) 233:122–128.

(List continued on next page.)

*Primary Examiner*—Amy J. Nelson
*Attorney, Agent, or Firm*—Davidson, Davidson & Kappel, LLC

[57] ABSTRACT

Promoters in the 5' non-translated region of genes from *Cuphea lanceota* that code for β-ketoacyl-(ACP) reductase are disclosed, as well as alleles and derivatives of said promoters. These promoters in the 5' non-translated region may for example be coupled with foreign genes, forming chimeric genes, and be transmitted to plants in appropriate vector systems.

10 Claims, 11 Drawing Sheets

OTHER PUBLICATIONS

De Silva J, et al. The isolation and functional characterisation of a *B. napus* acyl carrier protein 5' flanking region involved in the regulation of seed storage lipid synthesis. Plant Mol. Biol. 18:1163–1172, 1992.

O'Neil J, et al. "Cloning and charaterization of genomic B–ketoacyl–ACP synthase genes from castor." J. Cell. Biochem. 16F: 227, 1992.

Benfey PN, et al. "The cauliflower mosaic virus 35S promoter: Combinatorial regulation of transcription in plants." Science 250: 959–966, Nov. 1990.

Kim Y, et al. "A 20 nucleotide upstream element is essential for the nopaline synthase (nos) promoter activity." Plant Mol. Biol. 24: 105–117, 1994.

*Acl1;1* spezifische Sonde
Specific probe

SEQUENCE LISTING (1) GENERAL INFORMATION:

(iii) NUMBER OF SEQUENCES: 35

(2) INFORMATION FOR SEQ ID NO: 1:

(i) SEQUENCE CHARACTERISTICS:
      (A) LENGTH: 3250 base pairs
      (B) TYPE: nucleic acid
      (C) STRANDEDNESS: double stranded
      (D) TOPOLOGY: linear

```
    (ii) MOLECULE TYPE: genomic DNA (iii) HYPOTHETICAL: no (iii) ANTI-SENSE: no (vi) ORIGINAL SOURCE:
         (A) ORGANISM: Brassica napus (vii) IMMEDIATE SOURCE:
         (A) LIBRARY: genomic Lambda FIX II
         (B) CLONE: BnACCaseg3

(ix) FEATURE:
         (A) NAME/KEY: CAAT-signal
         (B) LOCATION: 2283..2286

(ix) FEATURE:
         (A) NAME/KEY: TATA-signal
         (B) LOCATION: 2416..2422

(ix) FEATURE:
         (A) NAME/KEY: transcription start
         (B) LOCATION: 2456

(ix) FEATURE:
         (A) NAME/KEY: start codon
         (B) LOCATION: 2506..2508

(ix) FEATURE:
         (A) NAME/KEY: CDS
         (B) LOCATION: join(2506..2803, 2896..3236)

(xi) SEQUENCE DESCRIPTION: SEQ ID NO: 1:

GTCGACAGAG ACAGGTTCGT TCATGGCTTT GATTTTGCTC CTGCATGTTG CTGTTTCCTG      60

TAACATAAAA AATATAAGTT GCCTTTCATC TGTTCACCTA ATATGTGAAA AAAATTCATT    120

TAACGTTCCA GTGGCTTCTG ATACAAGTGA TTACTAACAT TTGACAGGAT AACAAAGGTG    180

TTGAGGACTT TGGCGATATT ATCAGAGAAG GAGGTGGAGC TTTAGCGAAA GGCCTGTTTA    240

GAGGAGTCAC AGGCATATTG ACAAAGCCTC TCGAAGGTGC AAAATCTTCT GGTGTCGAAG    300

GATTTGTCTC AGGTTTTGGG AAAGGAATTA TCGGTGCTGC TGCCCAACCT GTGAGTGGAG    360

TTCTGGATCT TCTGTCAAAA ACCACTGAAG GTGCAAATGC CATGAGGATG AAGATAGCAG    420

CAGCAATCAC TTCAGATGAA CAACTTCTTC GCCGGAGACT TCCACGAGCT GTTGGTGCTG    480

ATAGCCTGCT TCGTCCTTAC AACGAATACA GAGCACAGGG GCAGGTACAA ATTTGTACTC    540

ATGACTCTTT TCAAACTGTA TTCCACTAGT GGTTTCTCTC CTGATGAGGA ATGGATTTAT    600

TCGTGATGAT GATACGTATG CAATGATTCA TTCGTCTAAC TTTTGCACTT ACAGGTCATA    660

TTGCAGTTGG CAGAATCTGG ATCATTCCTT GGCCAGGTTG ACCTGTTCAA AGTACGTGGG    720

AAATTTGCTT TGACAGATGC TTATGAAAGT CATTTCATCC TACCAAAAGG AAAAGTTCTA    780

ATGATCACAC ATCGAAGAGT AATATTGCTA CAAGTGAGTC ACACAATAAC CTCTTACTCT    840

TCTCAGTATA TGCATAAGGT CTATAATTGG TCTAGTGTTC GTCCTCGGTA TCTATGTAGC    900

CAAGAAATCC TCTTTGACAT TAGCAACATT TTATTTTATT TCCAGCAACC GTCCAACATA    960

ATGGGTCAAA GAAAATTCAT CCCGGCCAAA GATGCGTGCT CTATACAGTG GGACGTTCTA   1020

TGGACTGATC TTGTATTTAT GGAACTGACT GAGGCGAAAA AGGACCAGCC TAACTCCCCA   1080

CCGTCACGGC TTATTCTCTA TCTGAAATCA AAGCCAAATG ATTCGAAGGA ACAAGTCCGT   1140

GTTGTCAAAT GCAGTCCCAA CACGAAGCAG GCCCTTGATG TTTACTCAGC CATCGATACA   1200

ACCATTAACT TGTACGGGCA AAATGATTCA AAGGTTAGTG TAGCTTCTTT TTTCTTTCAC   1260

AATTAATTAA CAATAATGTC ACCCCTTGTT TTGTTACAAA AAAAAAAAA AAAAAAATG    1320
```

-continued

```
TCACCCCTTG TTTAAAACAA ATTCAGAATA TATGTTTTGG TTATTTGATT TAGGCATTGG   1380

TGAAAAACAA AGTGACAAGG CCGTATTCCC CGATATCTGA GAGTTCTTGG GCTGAAGGAG   1440

GTTCTCAACA AATGCCAGCT TCAGTTGCAC CATCTTCAAC CTTTGGCACA AGCCCAACGA   1500

CCAGCTCAAG TTAAAATCAA TCTTTAAGCT GCATCTTCTT GCTCTGTCAC CTTCTCGCCC   1560

GCCACCCTGG TAAATATTTT TTTCCTGCTT CTTCCTCTGA TCATTTCTCC ATTTGCCTCT   1620

GAACATGTAC TTCTGCCTGA TGATTTACTA TAACACAAAC ACAATCTAAT GGTTTCTATG   1680

CGTGTTTTTC GTTACTCAGT GTTCTTGTTC GAATACTAAC AGACATGTTT TCGTTTGTGT   1740

TCTTAGGTGG GTGAGATGAA ACACAGCTTT GGTATAAAGA CTTTTTCATC GTGCTCAAAT   1800

TTTCTTTCTC GCGTAGGATT TTCGTAAATC ATATCCGTAG AACCATATAT GTGTGTATAT   1860

ATAAACCTCT GCAGTAAAGA CTTTTCCAAC AGTAAACTCG TGTTGATCAA CACATGTATA   1920

TCGAAGCTGC CTTATATAAT TTTATTGTTT TTAGAGAATG TTGTCAAAAA GAACAAAAGA   1980

AACTATACTA TTATCTACTA AGATGATTTT ACAACTCAGT TATGTCTTTT CTAGTTAACT   2040

TTAAAAATAC AACTACAATG TTTTAATAAG TATCTATCTA TATTATTAAA ACAGGTTCAT   2100

TGCTGTTTTT TTTTCTTTTT TAATAAAAAA AACTCAGTTT TACTCAAAAC TAGAAAGATA   2160

TTTTTTTTTA TTTTATAAAT GCATAACTTT GATATCATCA TAAACATTTT AAATTGCTAC   2220

ATAGTTTACG AATAATAATT TATTTAGGTG AAAGAATTTT TTAAAAAAAG AGGTTAATCT   2280

ACCAATTGAA TATGATATTG TCATATTTAA TTCATAAAAT TCTTACTGAT TTGCAAGAAA   2340

AAAATAAATG GGCTAATCCT GTACCAGCCC TAACTCTTAA CTAAAAATAG GGTTGGGTTA   2400

AAATAGGGAT GGGTTTATAT TACACAAAGG AGGGCTTAAA CCTAACCCTG GACACAACAT   2460

CCCTCTCATT TTGGTCTGGC TTGATTGCAA AGTTTTCTAT CAAAC ATG GAG ATG        2514
                                                 Met Glu Met
                                                  1

AGA GCT TTG GTT TCG TGT TCT GCT GCC GGA AAT GGA GCT TCT GAT CGG    2562
Arg Ala Leu Val Ser Cys Ser Ala Ala Gly Asn Gly Ala Ser Asp Arg
     5                  10                  15

TTT AGA CTC TCC AAT GTT TCA CCA TGG ATC ACA TCA GCT CGT GGT GCA    2610
Phe Arg Leu Ser Asn Val Ser Pro Trp Ile Thr Ser Ala Arg Gly Ala
 20                  25                  30                  35

AGT GGC AGT GAC TCC CCA GCC ACA GTG AAG CTG GGA AGC AGC TCT ATG    2658
Ser Gly Ser Asp Ser Pro Ala Thr Val Lys Leu Gly Ser Ser Ser Met
             40                  45                  50

ATC AGA GCC TTC AAA GGA GTT TCG ATT TAC AAA AAC AAG ACC AGA AGA    2706
Ile Arg Ala Phe Lys Gly Val Ser Ile Tyr Lys Asn Lys Thr Arg Arg
                 55                  60                  65

AAT GTT TTG TCT CAA AGG AAC AAA CAG TTT CGT CCT ATG GCC TAC TTA    2754
Asn Val Leu Ser Gln Arg Asn Lys Gln Phe Arg Pro Met Ala Tyr Leu
         70                  75                  80

GGA AGG AAG GAC TTG AGC AGC CCT GAT CCG ACC TCC TTC TGC GAT AAT  G 2803
Gly Arg Lys Asp Leu Ser Ser Pro Asp Pro Thr Ser Phe Cys Asp Asn
     85                  90                  95

GTTTGCTTTA TTATTTTTGC ATTTTATTTA AAGTCGTATG CATATCGATG AACTAAGCAA   2863

ATCGTATTAT TTTTGCATTT TTATTTTTAC AG  AT ATA TCT GAA CCT CAA GGG    2915
                                    Asp Ile Ser Glu Pro Gln Gly
                                         100                 105

ACT GGA TCC ATT AAT GGG AAT GAT CAT AGT GCT GTA AGA GTG TCT CAA    2963
Thr Gly Ser Ile Asn Gly Asn Asp His Ser Ala Val Arg Val Ser Gln
             110                 115                 120

GTC GAT GAG TTC TGT AAG GCT CAC GGT GGA AAA AGG CCA ATC CAT CGC    3011
Val Asp Glu Phe Cys Lys Ala His Gly Gly Lys Arg Pro Ile His Arg
 125                 130                 135
```

```
ATT TTG GTT GCT ACC AAC GGA ATG GCA GCT GTC AAG TTT ATA CGA AGT        3059
Ile Leu Val Ala Thr Asn Gly Met Ala Ala Val Lys Phe Ile Arg Ser
    140                 145                 150

GTT AGA GCA TGG TCT TAC CAA ACA TTT GGC TCG GAA AAA TCC ATA TCA        3107
Val Arg Ala Trp Ser Tyr Gln Thr Phe Gly Ser Glu Lys Ser Ile Ser
155                 160                 165                 170

TTG GTG GCC ATG GCG ACT CCT GAA GAC ATG CGG ATC AAT GCG GAA CAT        3155
Leu Val Ala Met Ala Thr Pro Glu Asp Met Arg Ile Asn Ala Glu His
                175                 180                 185

ATC AGA ATC GCT GAT CAG TTT ATG CAA GTC CCG GGT GGA ACG AAC AAT        3203
Ile Arg Ile Ala Asp Gln Phe Met Gln Val Pro Gly Gly Thr Asn Asn
            190                 195                 200

AAC AAT TAT GCT AAT GTT CAT CTT ATT GTA GAG GTGAGTGCAA CTTT            3250
Asn Asn Tyr Ala Asn Val His Leu Ile Val Glu
        205                 210
```

(2) INFORMATION FOR SEQ ID NO: 2:

(i) SEQUENCE CHARACTERISTICS:
        (A) LENGTH: 4450 base pairs
        (B) TYPE: Nucleic acid
        (C) STRANDEDNESS: double stranded
        (D) TOPOLOGY: linear (ii) MOLECULE TYPE: genomic DNA (iii) HYPOTHETICAL: no (iii) ANTI-SENSE: no (vi) ORIGINAL SOURCE:
        (A) ORGANISM: Brassica napus (vii) IMMEDIATE SOURCE:
        (A) LIBRARY: genomic Lambda FIX II
        (B) CLONE: BnACCaseg1

(ix) FEATURE:
        (A) NAME/KEY: CAAT-Signal
        (B) LOCATION: 3124..3127

(ix) FEATURE:
        (A) NAME/KEY: TATA-Signal
        (B) LOCATION: 3328..3333

(ix) FEATURE:
        (A) NAME/KEY: Transcription start
        (B) LOCATION: 3367

(ix) FEATURE:
        (A) NAME/KEY: Startcodon
        (B) LOCATION: 4089..4091

(ix) FEATURE:
        (A) NAME/KEY: CDS
        (B) LOCATION: 4089..4421

(xi) SEQUENCE DESCRIPTION: SEQ ID NO: 2:

```
GAGCTCCTTG CGATGAACGG AGTTTGTCTT CAACCATCTC GTATATGCGC TTTCTTCTCC      60

TTCATGCTCC TCTTCTTGAT TCAGGAGGTA CCACATTAGC ATTCCAAACA TCATCTGGAA     120

CAACCCCACT ATCCTCAGGA ACACCTATTG GATTGATAGT TTCTTGATAA GTTGTTCTCC     180

AAGTGGAAGT CGTGTACATG TCATCCGTTA GGGAGGATGG GGCTCGACCA ACAGTTAAAC     240

CAGCCTTGAT TGCGTGTCTA CATGGGATTT TCAGTAGGTC GTATTTCCCA CATGAGCAGG     300

TTCTTCTGTC CAAATCAACC AGGCAGTCAA TTGTATCTCT GCGAACTAAA AAACGGTACT     360

CGTCAACTGG CTGCACCAGA AACGTTTTAC CCTTATTAAT CCGTCTGTCT ATCTTTTTCT     420
```

```
CGATGGCAAT AGTTAATGGT TTTGTGTGCT TCCTGCTTCG TGTGCGGCAT TAGAAGAACC    480

AACGGGTCAG CATTTCTATG ATGCTATCCA ACAAAGGAAT GACTGGATAC TCTCTTAGTG    540

TGCGCAAAGC AGAGTTTATT GATTCAGCTG GGTTTGTCGT CCTAATGTCA TACTTGAATC    600

CTGGAAACTG ACAACGAGCC CACTTTGTAA CATCTGCATC TGTTAAATAT TTTCCAATAG    660

TTGGACTAAT ATTACACATA GCTTGGAATC GCTTCTGAAA ATCAATGACT CTATAAGCTT    720

TAGAAGCTTT TGCAATCAAT CCAGCCAGTC TCTTTCCTCT GTAATGTGTG ACCACATTAT    780

TCAACAAATG GTGGATGCAA ATTCCATGTT GAGAAAGAGG ATACACATTC TCTATTGCCT    840

TACAAAGTGA GGCATTTCTG TCTGACACAA AAGCTAGAGA ATGCTCGTCC GCAACAACAA    900

CCTTTAGCTG TCTCATAAAC CAATCCCATG AACGATCATT TTCTGAGTCC ACGACCGCAA    960

ACACAACATG ATACAAGTTA GAGTTTCCAT CTAAAGTTGT CGCAGCAAGT AATACCCCTT   1020

TGTATTTGCT CTTTAAAAAT GTCCCATCAA CAACAAGAAC TTGTCGCATG GCTGTCTGAA   1080

AACCTCGTAC TGATTGGCCA AACGAAGCGA AGAGAAAATC TGAATCTACC ATCAACATCA   1140

GTTTTATAAA ACATATGCAT TCCTGGATTA GCTTCTCTCA GCATGTGCAA GTACTTTGGA   1200

ATTTTTCCAA AACTCTTCTC TGGAATACCT CCAACCATGC TAATTGCAAA CTCCCGAGCA   1260

TCTCATGCTA AGGACTTAGA TATCTCGCAT CCATGTTCCA TCCTCATAAT CTGTATGACA   1320

TCATTAGTTT TGGGACCTTC TTTCACACCA TCATACCTAT GCATTATTAG TCCGCCAATT   1380

GTTTTTGCAA AAGCTGTCCG ACCACCATTA TTCATACTCG ACGCAGCGCA TGTATGATCC   1440

GCCACATATT TTTTGATGAT GATATATGTG GAACCTGATA ACCCCTCAGC CCGAACACTC   1500

CATTTGCAAT GGTTGTCAAT GCATCAGATG TACCAAAGTT TTCTGTCAGA TTTCACAACT   1560

TTGTAATCGA AGTTATGCTT CATTGCTGAC ATTTCCAAAG CTGCTTTCAA CATGGTTTTG   1620

TTTTGAAACG TTTCACCCCT CTTCACAACA TCCATCAAAG AAAACACTTT TTCCACTATC   1680

GTCTTCTTTT GCACTTATGG CGAGAACATC ATCTTCTTCA TAGCCGTATG AGTTACAATT   1740

ATCTTCAACA TCTTTGCTTG ATTCAGATGA ACTAATAGTG TCATCTCGAG GTGGAAATGA   1800

GGAAGGTTCA CCTTGCTCTC TGAAATGCGA GTTAGATTTC TCATTATCAG CCCCAATGTT   1860

GTCGTTGTTT CCACTGATAG GTGAAGTTGA CACACACAAC CTTGTAGAAG CTTTTCCACG   1920

TACATATGTA AGAAAATTTT TGACTTGCCG ATCACTCTCA ATGATAACTG GGGACAGTC    1980

TATTGAACTG ATTAACTCCA TATGTAAGTA GCTTAACTCA AGCTCGACAA GGTTTTGGTC   2040

AGTTCCAAAA TCTTCAAAGG AACTTGTCAA TTCCATGTAC AGTACTCTAC CTCGTTTGTT   2100

CTTATCAACC GCAAATCCCC ATCCTTTAAG GGGATCAAAT TTCCACAACA CACAAGAAGC   2160

ATATATATGC ATCTTCTTCA ACAAGAAATT CAAAATTTTT GGATGAAAAA AAAATCAAAA   2220

TCGTCTCACC AAGAAGAAGA CCACGATTTT TTTTAAAAAA ATTTACTTGG AAAACACGAA   2280

ATTTTAGGAA AATAGATTTA GAATATATTC TCTTAACAGA TTTTGGAGAT ATTTAAGGAA   2340

AATATACAAT TCAAAATTCG TAGAACATAC ATTACGTTGT CCGTAGAATA AAGGAATTTG   2400

GTAGATTATG GAATCATATT ATCGCAGTCA TGAGACATGG CAGATTTTGT CATTTCGCCT   2460

TTGTAGATAT ATTGGAAATA ATAGTTAATC AAATCTACCG TAGTTCAGAA ATAAAAGAAA   2520

TGGTAGTCGA TTAATTCTAT CATGTCTATC GTAGTTCAAA AATAAAAGAA ATGATAGTCG   2580

TTTAATTCTA CCATGCTAGA ATTATAACAA ATGCTCGATT TAACGTTCTG CTGGTTGCAG   2640

ATATTCATGT AGTTAGCCGA ATATGCAATC TACATCCTCG TAGACACTAG ATTATGTTTT   2700

CTGCCATCAG TAGACCAAAA TATGAAATTG TGTTCCACAA ATATTTATTC AACCAAAGTA   2760

TTTTTCATAT GTTTGTCTAT TGTTTATATA CATTTTCCAT ATTTTTCCAT ATTTTTCTGA   2820
```

```
TTCTTAAAAT AATTGATATG ATTTTTCAAA GTTGATCAGG GTATCTAAAT CCAAATTTGA      2880

CAAAAAAAAA ATTTATGGCA AAGAGACAAT GTACTTGTTT TTCTATTTCG ATTTGGCAAT      2940

TTTTTTTTTT TTTACCGAAA GGAATCATAA CATTAAACCA ACCAACTAAT TAGAAAAGAA      3000

AAATAGAGAG AGAGAAGAAT TTGACTTCAC TTTATTATGG AATGGTAAAT AGTGAAAAGG      3060

TGAAAAAAAT TATTAAAAAA AACTTGACAA GAGATTTTTT TGTTTTTAAC AGAATGTAAG      3120

AACCAATAAA AAGAGTGCGG AAAAAACAAG AGTGGAAGGT TTGATGAGGA GAGAGGTAGC      3180

TGAGGAACAA CTACGGCGCC TCCTAACCAA AAAAAAAAGA GAAAAAGAAA AAGAAAAAGA      3240

AAAAAAAATG GAGAAGGTGT GGAGTGTGGC GGAGGCAGAG ACCACGTGCA CTCTTTTCTC      3300

TACACCTTCA TCTTCTTCAT CTGCCACTAT TAAGTCTTCG GACCCCACCT CCTTCCGTCT      3360

CCTCTAACTC CAACCTAACT CTCTTCTTCC CTCTCCCGCC TCTTTAAACC CACCCTTCTC      3420

TCTCTCTTCT GCTCTGAGAT GATTCTTTAA CTTCTCTCAA CTGAAATTGG GATTCTCAGC      3480

TTTTCCTACA AGGTTCGGAC TTTCTCTTTA ATTGGGGTTT GTGATTCCTA ACTGCTGATT      3540

ATTCCTGATC TCACCATCTG AACTTTACTC TTGTGTTGGC TGTTATTTGA GATGAGTTGT      3600

AGTTCCTGAT TTCAATTCCT TATTGGAGCT ACCTCTTAGA GTTTCTCACT TCATTTTTTT      3660

TTTCTTCCGG GATGTGGAGT GTTTTCATCG TTAGTTGGTT TTTAGATCTC TCAGATTTTG      3720

TTTTCCTTTC TACAAGAAAC TGGTTATCGG AAGAGATAAT TAAGTTTTTT TCTTTTCTTT      3780

TCAAAAAGAG TATTTTGTGA TGATTTCTAA CTTTCAAGAG ATCTTTGCTT ATGATTGTGT      3840

TTTGCTTGTC GTATACTTTT CTTCTTCTAA AATACAGCAA AACATTGCTG TCATCTTCTT      3900

CTTCTCTTTT TTTTTTTTTT TTGTGAGCAT CTTCATTTAA TAAAAAATAC ACAAAGCAAT      3960

GCTGTCATCT GCGGATATTT TTAAGCAGAT CAAGATCATT ATTTTCTGTT TCCTAGTGAT      4020

AGTATCTAAG GGGTTTTATT ACATCAGTTT CCTGTTTCAC TATGTCTTTG TTTTACAGAA      4080

GAATAACA ATG GCT GGC TCT GTT AAC GGG TAT CAA ACT CCC GGT AGA AAT      4130
         Met Ala Gly Ser Val Asn Gly Tyr Gln Thr Pro Gly Arg Asn
            1               5                  10

CAT GTT TCG GTG TCT GAA GTG GAT GAC TTT TGC ATT GCA CTT GGA GGG          4178
His Val Ser Val Ser Glu Val Asp Asp Phe Cys Ile Ala Leu Gly Gly
 15              20                  25                  30

AAA AGG CCA ATC CAT AGC ATT TTG ATC GCT AAC AAT GGA ATG GCA GCT          4226
Lys Arg Pro Ile His Ser Ile Leu Ile Ala Asn Asn Gly Met Ala Ala
                35                  40                  45

GTT AAG TTT ATA CGC AGT GTC AGA ACA TGG GCT TAC GAA ACA TTT GGC          4274
Val Lys Phe Ile Arg Ser Val Arg Thr Trp Ala Tyr Glu Thr Phe Gly
             50                  55                  60

ACC GAG AGA GCT ATT TTG TTG GTT GGG ATG GCG ACT CCT GAA GAC ATG          4322
Thr Glu Arg Ala Ile Leu Leu Val Gly Met Ala Thr Pro Glu Asp Met
         65                  70                  75

AGG ATC AAT GCC GAG CAT ATC AGA ATC GCT GAT CAG TTT GTC GAG GTT          4370
Arg Ile Asn Ala Glu His Ile Arg Ile Ala Asp Gln Phe Val Glu Val
     80                  85                  90

CCC GGA GGA ACT AAC AAT AAC AAT TAT GCC AAC GTT CAG CTT ATC GTT          4418
Pro Gly Gly Thr Asn Asn Asn Asn Tyr Ala Asn Val Gln Leu Ile Val
 95                 100                 105                 110

GAG GTGGGTGAAT ACAACCAATA GTAATAATA                                     4450
Glu (2) INFORMATION FOR SEQ ID NO: 3:

(i) SEQUENCE CHARACTERISTICS:
        (A) LENGTH: 3350 Base pairs
```

(B) TYPE: Nucleic acid
        (C) STRANDEDNESS: Double stranded
        (D) TOPOLOGY: linear (ii) MOLECULE TYPE: DNA (genomic)

(iii) HYPOTHETICAL: NO (iii) ANTI-SENSE: NO (vi) ORIGINAL SOURCE:
        (A) ORGANISM: Brassica napus (vii) IMMEDIATE SOURCE:
        (A) LIBRARY: genomic Lambda FIX II
        (B) CLONE: BnACCaseg10

(ix) FEATURE:
        (A) NAME/KEY: Startcodon
        (B) LOCATION: 2611..2613

(ix) FEATURE:
        (A) NAME/KEY: CDS
        (B) LOCATION: join(2611..2908, 3001..3341)

(xi) SEQUENCE DESCRIPTION: SEQ ID NO: 3:

```
GATCCATTTT AATATTCATC ATCCTACCTG CTAGAGACAA TTTAAAGAGA CCTTTTCTAC      60

AACCAGTGTA GATTGGTTGA TTTGCAGCAT CTAGCATTTC ATAAAACCTT TTGCATCCAA     120

ATTAGGTTCT TCTACATTTC CAGTTCTATC ATCTATTGTT GTAGTTGTTT CTAAAAATGC     180

ATCAGTAATC ATGTCTTGAA CCCTATCATG ATCTACCATC TGACCTTCTT GATGATAATT     240

ATATTCATTA CGCAAATGAT TCGGTTCTTC ATTATTACCA ACATCCTCAA AATTATTATT     300

ACTATTACTA GCTTCATTTC CACCATAACC CTCTCCGTGT TGATACCAAA TATAATATTG     360

TGGTGTAAAT CCTATGTTTA CTAAATGCTT CCATACAGTT TCACTACGTG CAAATTTTGA     420

ATTCTCTCAT TTCCGACAAG GTCAGAACAT CTTACCGCTT TCCTGCGTGA TCGGTGTAGA     480

GTCCGCCTGG TACATGAATG TCTCTAACCC GCTCAGAAAT GCATTCGTCA CTCTCCCTTC     540

CGAATCTTTA TGAGAATACA TCCAACTCCG TAGCTCTTAA ATATTACCAC CGTCCGCCAT     600

TTTTTTTTCG GAATTTTTTT TTTGGAAATT GTTTTGGGAT TTTTTGGGAA TTTTTTTTTT     660

TAATTTTTTC TGGAATTTTT TTTCTCAAAA CTTTTTTCTT CTTCTTTTCC TTTGTGTGTT     720

GTGAGAGAGT GAGTTGTGAG AAATGACATA TATATAGAAA AAATTTCGAA TTTGGTAGAT     780

GAAGTATAAC AATGATTTTA CTAGGAAAAT TTTACTAGGG TTTTACATCT CTCTTACATC     840

GGTTTTACAA GAAATTTACA ACGAAATTAG GCAATTCAAA GCGCATTGAA TACACGTTTT     900

CACCAGTAAA TAACAGTAAC ATGTTTTATC TTAATATCCT CGTATATTTA CGATGAATAT     960

TGTTCGCGAC GTACTTTCGT CGTAAATGTA CAATGTATTT ACGACAAAAT GTTTTTCTTG    1020

TAATTTTACG TCTACGTTAC GACGAATTTC TATTTCGTCG TAACATCCTC GTAAACTACT    1080

CGTAAGTTTA CGAGGAAAAA TTTTTCTCGT AACTTTTCGT CGTTACGGAA ACGTTTTCTT    1140

GTAGTGAGAG AATACACTAA TTTTTATCAA ATCTTTATTA TTCAACATCA TTAATTTTTA    1200

TATATACTTT AGTAACATTA GAAAATTCCG TAACTTTTAT TTAAGGAAAA AATAAAAAAT    1260

ATTAATAATA AATTTATGGT TAGTTTAATA AAAAGTTTAT TATATATTTA GATGAACCAA    1320

CATGTTTCTC TAAGAATTCT AAAACTCATT GTGGTGATGA CACATGACTA CCCTAAATGT    1380

TGTAATGATT CTCTTTTAAT ATATATGAGA TATAATTTTA GCGAATAAAA TTATATATTG    1440

TAATGACTTC TAATGAACTA TATATCTTCG TATGTTTTCA TGTCATGGAT ACACAGAGAA    1500

AAATTAATTT GGGTGTGGAC AACATTGGAA TAGCATTCAT TCATTTTGAC ACCCGACCCA    1560
```

```
GACCCGCGGT TGAACCTGTA AATCCGGTAA CCCAGAAAAA ACTTGGTTTG AGTTTAGTGA    1620

AAAACCCAAT ATTTAGAAAC CCGTAAAAAT CCAGTAAAAC TCGAAACCTG ATACCGGTTG    1680

AACCACCAAT TGAACCAATA AATAACTTTT ACTTCTTTTT TGAGTTTTTA ATTATGTTTT    1740

TAGATTATAT TTTATATTCT AAATTTCCAA TTAAGAAATT AGGTGCTGAC AAAAAAAAGA    1800

TGTTAGATTT TCACTTTTCA ATTTTATATT TGTGATTTTA GATTTGATG AAGATTTTAC     1860

TATGCCATCT GAAGAAAATG AAGTGAACGA TGGTAGAGAG AACCAAAATT AGTTGAAGTG    1920

ATTTGGTGTT AGTTTATTTC TGTTATTGAC AATTTATTAC AATGATCTTT TATTTTTGGT    1980

TTATTTTGTA TTTAAAGTTT AATTTATTAT TCACATTAAA TATTTAAATA TTTATAAATT    2040

TTATGTCTTG ATTTTTTTAT ATATCATAAC TCTTACTTTG TTAGAAAAAT TTATAAATAG    2100

TCTAAACTAT TTTTTGATAT TTTGTATGTC AAATGAAAAT AAAAATTTAA AACTAAAATT    2160

AAATATTTTC TAAATGTTTT TAAACATAAA ATATATACAT ACCCAAACTA TTATTTTATG    2220

TTTTAAAAAC ATTTTAAATT ATTAAATTTT AGTTTCTATA TTTTTATTTA CATAGCTGAT    2280

ATATTATTAT ATAATAAAAT TAATTCATTT ATTAACCCGC GGTTAACCTG CGGTCGATCC    2340

AGTGACCCAG CAACCCGGTA AATCGTCCGG TTCAGTGTCC AGGTCGGATT TAAAAATATC    2400

GGGTATTATA CTTTTTTCTT GGTTTAGAAT ATATTTGAAT CGTAGATTTA GTGCTGTCTA    2460

AATATTAGGA AAGTTATTTT ATATCTTTAA AATGAAAAGA TTTAATATGG AGGGTACTTG    2520

AGTATTTTTA CAAGGTTCTA GGGTTACGTT TTCTACAACA CTATTCACGG TCATTTTGGT    2580

CTGGCTTGGT TGCAAAGTTT TCTGTCAAAC ATG GAG ATG AGA GCT TTA GTT TCG    2634
                                 Met Glu Met Arg Ala Leu Val Ser
                                  1               5

TGT TCT GCT GCC GGA AAT GGA GCT TCT GAT CGG TTT AGA CTC TCC AAT     2682
Cys Ser Ala Ala Gly Asn Gly Ala Ser Asp Arg Phe Arg Leu Ser Asn
 10              15                  20

GTT TCA CCA TGG ATC ACA TCA GCT CGT GGT GCA AGT GGC AGT GAC TCC     2730
Val Ser Pro Trp Ile Thr Ser Ala Arg Gly Ala Ser Gly Ser Asp Ser
 25              30                  35                  40

CCA GCC ACA GTG AAG CTG GGA AGC AGC TCT ATG ATT AGA GCT TTC AAA     2778
Pro Ala Thr Val Lys Leu Gly Ser Ser Ser Met Ile Arg Ala Phe Lys
             45                  50                  55

GGC GTT TCG ATT TAC AAA AAC AAG ACC AGA AGG AAT GTT CTG TCT CAA     2826
Gly Val Ser Ile Tyr Lys Asn Lys Thr Arg Arg Asn Val Leu Ser Gln
             60                  65                  70

AGG AAC AAA CAG TTC CGT CCT ATG GCC TAC TTA GGA AGG AAG GAC TTG     2874
Arg Asn Lys Gln Phe Arg Pro Met Ala Tyr Leu Gly Arg Lys Asp Leu
         75                  80                  85

AGC AGC CCT GAT CCG ACC TCC TTC TGC GAT AAT  G GTTTGCTTTA           2918
Ser Ser Pro Asp Pro Thr Ser Phe Cys Asp Asn
     90                  95

TTATTTTGC ATTTTATTTA AAGTCGTATT CATATCGATG AAACTAAGCA AATCGTAATA    2978

TTTTTGCATT TTATTTTTAC AG  AT ATA TCT GAA CCT CAA GGG ACC GGA TCC    3029
                        Asp Ile Ser Glu Pro Gln Gly Thr Gly Ser
                                100                 105

ATT AAT GGG AAT GAT CAT AGT GCT GTA AGA GTG TCT CAA GTC GAT GAG     3077
Ile Asn Gly Asn Asp His Ser Ala Val Arg Val Ser Gln Val Asp Glu
110             115                 120                 125

TTC TGT AAG GCT CAT GGT GGA AAA AGG CCA ATC CAT AGC ATT TTG GTT     3125
Phe Cys Lys Ala His Gly Gly Lys Arg Pro Ile His Ser Ile Leu Val
                130                 135                 140

GCT ACC AAT GGA ATG GCA GCT GTC AAG TTG ATA CGG AGT GTT AGA GCA     3173
Ala Thr Asn Gly Met Ala Ala Val Lys Leu Ile Arg Ser Val Arg Ala
            145                 150                 155
```

```
TGG TCT TAC CAA ACA TTT GGC TCG GAA AAA TCC ATA TCA TTG GTG GCC      3221
Trp Ser Tyr Gln Thr Phe Gly Ser Glu Lys Ser Ile Ser Leu Val Ala
        160                 165                 170

ATG GCG ACT CCT GAA GAC ATG CGG ATC AAT GCG GAA CAT ATC AGG ATC      3269
Met Ala Thr Pro Glu Asp Met Arg Ile Asn Ala Glu His Ile Arg Ile
        175                 180                 185

GCT GAT CAG TTT ATG CAA GTC CCG GGT GGA ACG AAC AAT AAC AAT TAT      3317
Ala Asp Gln Phe Met Gln Val Pro Gly Gly Thr Asn Asn Asn Asn Tyr
190             195                 200                 205

GCT AAT GTT CAT CTT ATT GTA GAG GTGAGTGCA                            3350
Ala Asn Val His Leu Ile Val Glu
                210
```

(2) INFORMATION FOR SEQ ID NO: 4:

(i) SEQUENCE CHARACTERISTICS:
        (A) LENGTH: 1200 Base pairs
        (B) TYPE: Nucleic acid
        (C) STRANDEDNESS: Double stranded
        (D) TOPOLOGY: linear (ii) MOLECULE TYPE: DNA (genomic)

(iii) HYPOTHETICAL: NO (iii) ANTI-SENSE: NO (vi) ORIGINAL SOURCE:
        (A) ORGANISM: Cuphea lanceolata (vii) IMMEDIATE SOURCE:
        (A) LIBRARY: genomic Lambda FIX II
        (B) CLONE: ClACPg1

(ix) FEATURE:
        (A) NAME/KEY: TATA-Signal
        (B) LOCATION: 1051..1054

(ix) FEATURE:
        (A) NAME/KEY: Startcodon
        (B) LOCATION: 1160..1162

(ix) FEATURE:
        (A) NAME/KEY: CDS
        (B) LOCATION: 1160..1200

(xi) SEQUENCE DESCRIPTION: SEQ ID NO: 4:

```
CTGCAGGAGC AATTGCATCA AAAACACCCT TCACCTGAAG TAGACCATCA TAAAAGACAA     60

CTTTAATCAT TCAACAGCAT ATTTTTACAA AGTAGATTGT CAAAGAAAAA ATAACTAAGG    120

GAAAATGAGA TGTTGACAAC CTGCAAAGCT AAATCTCGGG TTGGCAGCAC CACTAAAGCA    180

CGGAGGCATT TGACAGCACG AGTTGAAAGC TTCTGCACAA TTGGCAGGGC ATAAGCTAAA    240

GTTTTCCCGC TTCCAGTTGG GGAGTTGATG CAGAGGTCTC GCTCAAATGC GCCTGGTCCA    300

ATCGTCTCTT GCCATACTGC GACTTGCACC GGGAAGAGCG AAGCGATATC CATCTTCTCC    360

AAAGCCGCTT TCAGCCTAAA ATGAAAGGAG TTGCATTGAA AATTCAGTGA ACAACAGAA     420

GTTCAACAAC TTAAATGACG AAATTGAGGC ACTGAATTTA ACTAGGAAAA ACTGTATATG    480

CCAATGACTT TATATTACTG AAACAATTCT CACGCAGCCA CAAGGGCAAA CTCAACAGTG    540

CACAACTGTA AAAATCATTC GACAAGACGA AACATATAGG AAAGGACAAC CTTTGGGACA    600

TACACAATAA CAAGAGACAA CAAAAAGGGT TTGTTCCGAC ACAAACTTTG CAAAGTTTGA    660

GACTTTCTTT TGTCGGGCAT CAATATATCT CCAGAACGAC TAAACTGAGA CAGTTATGGT    720

AAGCTGGTGA TGGATGGACA GAAAGAGAAA GCAAAACCAA CCTGGGGTCG AGAAAAGGAA    780
```

```
GAAGCCTTCA GCTGACAATC TTGCAACAGA CTGACGTCCA CTGGACTTCT CATCCATGGC    840

AGCACCGGCA CGCCATCCCC TCCCCCTTCT CTTCTTCACC CATCGCTTCC CAACAAGAGG    900

CAGAGGCAGT GGCGGCAAAG CAAAGCCCTT AACAAGAAAA GCATCAATGA GCAGTTGCTG    960

GTGGGCTTAA CAGGGCCGAA TAGGGATAGA GTTATCCATG TTACCAAACA GCAGCCTTAA   1020

AAGTTCGATA CAAACAAGGC CGTACGTCCC TATAAACTAA CGGCAACCCA CCAAACCTTA   1080

ACAAACAACC AAACCAAACC AACTAACACT AGGCCACGCC TCTCTCGCCT CATTTGCTCG   1140

CTCCCTCCCT CCCCCATCA ATG GCT TCC GCA GCT GCC GGT GCT TCC ATC TGC   1192
                     Met Ala Ser Ala Ala Ala Gly Ala Ser Ile Cys
                      1               5                      10

ATC AAG TC                                                          1200
Ile Lys (2) INFORMATION FOR SEQ ID NO: 5:

(i) SEQUENCE CHARACTERISTICS:
        (A) LENGTH: 1103 Base pairs
        (B) TYPE: Nucleic acid
        (C) STRANDEDNESS: Double stranded
        (D) TOPOLOGY: linear (ii) MOLECULE TYPE: DNA (genomic)

(iii) HYPOTHETICAL: NO (iii) ANTI-SENSE: NO (vi) ORIGINAL SOURCE:
        (A) ORGANISM: Cuphea lanceolata (vii) IMMEDIATE SOURCE:
        (A) LIBRARY: genomic Lambda FIX II
        (B) CLONE: ClKASIg2

(xi) SEQUENCE DESCRIPTION: SEQ ID NO: 5:

CATGCAGCGG TAGTTGCTAT AGATGACAAC CGCAGTTTCC CCGGCCGGCG GGCACTTCTC     60

CGGGTAACCG CGTAAAAGGG TCCCTCTTAC TCTTCATCAG AAGGTCGAAA GCCGCCATCT    120

TCCCTTCCTT CTCCCTCTCC TCCCTGTCCC TCTGGATGAA AGGGTTATTA CTGAGGGACC    180

GGGCTTTTCC GTCTGTCACC GAAGATGACT TCGGCTCGGG TTTTTGCTCT GCCGTTGTCT    240

CGGGACGCAG AGACTGAGTC TTTTTCAGGT CTTTCCCCGG CGGTTTCGGA GTCAGCTTGG    300

CGTCAAGCTC CTCAAGAGTG TGGAAAGACA GGTTCTTGCG GGGTGCTGTT GGCGGGGACT    360

CCGGCTTGGC CTTGGCCTTG GCCTGTGGGG CGGTGGGCTT AAGGTCCTGG AGAGCCATGC    420

TAACCTCTAC CCATGTAGAT TTCGGGCGTC ATCGGCTTTC TCAAGCTTGT TAAGCTGGTC    480

GAGGATGGTG GCCGGAAGCT TAGCCGGCTT CTCCGGCGTT GTCGAGGGTG GCTGGTCCTG    540

GTCCTGGTCC TGGTCCTGAT CCTGGTCCTC CTTGGCGGGG TTGTCCACAA CAATCCAAGG    600

TTCCTTGATG GAGTTGATGT CGAAGACGGC GAAGCTGGAT GGCGCGGGC AGTAAGCGTC     660

GGCCTTGACG GCGGCACTTC TGGAGGATGC GCAGCCCATC GTCACTAGGG TTTGAGGCTC    720

AAGTGTGGAT TGAAAGGCTA TATGAAGGTG GTGGGAAAT GGGTGGAGGA GGTTTTGTCT     780

GGGACTTGGA GGGTTTTGTG GCGGTTTGTT GGCTGCCTTG TGGGCCTATG AACTGAACGT    840

GTGGTGGCTA TCCCGCCAAA TCTGCGCCTC ATCGCATAAG ACACGCTGGC CATGACATTG    900

TCTCAAACCT GCACCAAGGA TATCATTTCT TGGACGTTGT CGTGGCTCGT TTTTTGTTAC    960

TATGTTATGT AAATATCTCA ATTTGCCCGA CTAGATTTGG CCTCATATTT CGATACAACC   1020

CATCTAAACA TCTCGAATCC GATAAGCCTA TTCAATTGGG AATTGCCTCA TAGCTAAGGT   1080
```

```
AGATGTGGAT TCAATGATTA CTC                                              1103
```

(2) INFORMATION FOR SEQ ID NO: 6:

(i) SEQUENCE CHARACTERISTICS:
        (A) LENGTH: 278 Base pairs
        (B) TYPE: Nucleic acid
        (C) STRANDEDNESS: Double stranded
        (D) TOPOLOGY: linear (ii) MOLECULE TYPE: DNA (genomic)

(iii) HYPOTHETICAL: NO (iii) ANTI-SENSE: NO (vi) ORIGINAL SOURCE:
        (A) ORGANISM: Cuphea lanceolata (vii) IMMEDIATE SOURCE:
        (A) LIBRARY: genomic Lambda FIX II
        (B) CLONE: ClKASIg2

(xi) SEQUENCE DESCRIPTION: SEQ ID NO: 6:

```
GATCTCTATG CAGCGTAGTT GTATAGATGA CAACCGCAGT TCCCGCCGCG GCACTTCTCC         60

GGTAACCGCT AAAAGGTCCC TCTTAATCTT CATCAGAAGG TCGAAAGCGC CATCTTCCCT        120

TCCTTCTCCT ATCTCCTGTC CTCTGATAAA GGTTATTACT GAGGACCGGC TTTCCGTCTG        180

TCACGAAGAT ACTTCGCTCG GTTTTGCTCT GCCGTTGTCT CGGACGCAGA GACTGATCTT        240

TCAGTCTTCC CGCGTTCGAG TCACTTGCTC AACTCCTC                                278
```

(2) INFORMATION FOR SEQ ID NO: 7:

(i) SEQUENCE CHARACTERISTICS:
        (A) LENGTH: 214 Base pairs
        (B) TYPE: Nucleic acid
        (C) STRANDEDNESS: Double stranded
        (D) TOPOLOGY: linear (ii) MOLECULE TYPE: DNA (genomic)

(iii) HYPOTHETICAL: NO (iii) ANTI-SENSE: NO (vi) ORIGINAL SOURCE:
        (A) ORGANISM: Cuphea lanceolata (vii) IMMEDIATE SOURCE:
        (A) LIBRARY:genomic Lambda Fix II
        (B) CLONE: ClKASIg2

(xi) SEQUENCE DESCRIPTION: SEQ ID NO: 7:

```
AACAGGTTGG CATTTAAAAA AAGAATAATA GTCTCGTTAG TTACAAAGTT TGTCGTTTAT         60

TGTCGCTCTC AGGTTATAAA CATATGCTGT ATTGAATTTC TGACGCTTCA TTTGTTAATG        120

ATGTTGCAAA AGATCGATGA ATCATTTAGT TTGCACCAGA AATTTAAATT TACATATCTT        180

AACCCACATA ATTTTATTTG TAATGGCGAC TCGA                                    214
```

(2) INFORMATION FOR SEQ ID NO: 8:

(i) SEQUENCE CHARACTERISTICS:
        (A) LENGTH: 1191 Base Pairs
        (B) TYPE: Nucleic acid
        (C) STRANDEDNESS: Double stranded
        (D) TOPOLOGY: linear (ii) MOLECULE TYPE: DNA (genomic)

```
        (iii) HYPOTHETICAL: NO (iii) ANTI-SENSE: NO (vi) ORIGINAL SOURCE:
              (A) ORGANISM: Cuphea lanceolata (vii) IMMEDIATE SOURCE:
              (A) LIBRARY: genomic Lambda FIX II
              (B) CLONE: ClKASIg2

(ix) FEATURE:
              (A) NAME/KEY: Startcodon
              (B) LOCATION: 1143..1145

(ix) FEATURE:
              (A) NAME/KEY: CDS
              (B) LOCATION: 1143..1191

(xi) SEQUENCE DESCRIPTION: SEQ ID NO: 8:

CGCGTAAAGG GAAATCCGAC TTCCCAATTA TGTTCTAAAG CATCTTTTAT ATTGCACATA       60

AAAAAGACAG CTAGCCGCAA GAACAGGTTG GCATTAAAAA AAAGAATAAT AGTCTCGTTA      120

GTTACAAAGT TGGTCGTTTA TTGTCGCTCT CAGGTTATAA ACATAGCATG TATGAATTTC      180

TGAGCTTCAT TTATTAATGA TATTGCAAAA GATCGATGAA TCATTTAGTT TGCACCGGAA      240

ATTTAAATTT ACATATCTTA ACCCACATAA TTTTATTTGT AATGGCGACT CGATTCAAAT      300

CGATTTCATG GGACGGGATT GAAATTTGAA ACGTATGTAA ATACCAACTC CGGAGAAAAT      360

GGGAAGATTG TACTTTGCCT ACATATTCAG GTGCATTTTA CCCGGATAAT GATGATATAT      420

ATAACGTTTG GTGTAGATGG AGATACGATA TATTCTTAGA TTCTTCTATT GAAAATAACA      480

TATATTCATG AGATAATTCG GAAAATACTC TATTCTTATG AGATTCCCTA ACATATAAAA      540

GAATATCATT ATGGAGAAAC AATAGAAAAT AGAGTATATT CAGGCGAGGT CAGAGATGCA      600

TCAGTTTATA AGATAGGCTT ATTTCAAGTG GACATCGTCT AGATAGGCTT TATAATACCG      660

AGTCAATAAA AATTCATCTT CATCGATTAG AAAGTGTAGA TTAATTAGGT CCGGGTAGAG      720

TACAATATTA GATGAGCAAT TTAACACATG ATTGTCACAT TTACTTGCGG ACTCCACGGC      780

ATGTTATATG TCTTGTACAA AAATGGACAT CGTCTAGATA GTCTTAATGA TACTGAGTCA      840

ATAAAAATAC ATGTATTTAA TATGCCATGT TATGTAGGTT TGCTAGTAAC GTCTAATATT      900

CTTGACAAAA ATGGTTTATG TGTATCGTAA TCATCGCGGC CGTTGAGGGC ACTCACGAAA      960

ATGGGAACAT GCCTTTGCTC GGCGGATTAT ACAAAAACAA CAGCAGCCTC TATCGATCTA     1020

TCGCCTCTGA AAACCCAAAG TTCAATCTCC TATTAATATT ATTGCCATTG TAAGTTCATC     1080

ACGTAGTTCC CCTTAATTAA TATTACTTGA CAAGGAGAAC TAGAGTAGGA AGGACACACG     1140

GG ATG GCG GGA ATC GCC GGG ACT TGT TCT ACC GGA GTG CTC CTG AGC       1187
   Met Ala Gly Ile Ala Gly Thr Cys Ser Thr Gly Val Leu Leu Ser
    1               5                  10                  15

AAG C                                                                  1191
Lys (2) INFORMATION FOR SEQ ID NO: 9:

(i) SEQUENCE CHARACTERISTICS:
             (A) LENGTH: 2450 Base pairs
             (B) TYPE: Nucleic acid
             (C) STRANDEDNESS: Double stranded
             (D) TOPOLOGY: linear (ii) MOLECULE TYPE: DNA (genomic)

(iii) HYPOTHETICAL: NO
```

```
    (iii) ANTI-SENSE: NO (vi) ORIGINAL SOURCE:
          (A) ORGANISM: Cuphea lanceolata (vii) IMMEDIATE SOURCE:
          (A) LIBRARY: genomic Lambda FIX II
          (B) CLONE: ClKASIg4

(ix) FEATURE:
          (A) NAME/KEY: Startcodon
          (B) LOCATION: 1963..1965

(ix) FEATURE:
          (A) NAME/KEY: CDS
          (B) LOCATION: 2402..2450

(xi) SEQUENCE DESCRIPTION: SEQ ID NO: 9:

CCCGGGATTG CTTCTTTTCT TGCTGCATAA GTAATCATAC ATACTATTTA GTACCTAACA      60

CATCAATTTC GTTATTCAGT TTGCAAAGTT ACATTAATAA AGTCCCGGAA TATTATTTTC     120

GTCATCAAGT TTGCAGAACT GCATAAATTG CATGATCATC GATTTATCAA AATTATCAAG     180

ATACATCACT TATTCTGATG GTAATGAATC TGACTTTAAT TCTAAAGACT GGATACATAG     240

ACGATTCTCG ACAGAGAACT CGAGTCATCA TCGCTACGCA CTTTTGTGTT TGCAAATTTA     300

GATCGCCATC AACCCATCTT CACTAGCCAT ATCAAATGTA TTTGTTTATT CTATAAAATA     360

AAACAATTTG AAATATTAAG ATCATAGATT TAACAAAAAT TTTAGTAATT ATTCTAATAA     420

ACGATCTACA TTTACTAATA AATAATCGAA TGACATATGA ATGGAAGTAC TATATTTTCA     480

ATTGCCATTG AAACACTTTA AAAATCATTA TTAAATATAA AAATTAGTTG CTAGATTTAG     540

ATTAGATTTT TTCTAAACTA TTTTCCTTTT GAGTACAAAA TCATCTAAAA AGTACCTACA     600

AGGAGTAAAA ACATGTAAAA GACTAGGGGT GGCAAAAAAG ACCAGGCGGC CCAGCTCGTT     660

TGAGCCCCAC CCGATAATAT ATTTTCTGTA AAATTTTTAA AAGTATGTCA TAAAATTTTT     720

TTTTTAAAA ATTAATTTAA TAAATTATAT ATATATATAA CTATTTATAA GAAATATATA     780

TTTAATATAA CTTTTATTGA TTTAAAATAT TAACGGGCCA GTTCGAAAAT TTTGTACCTA     840

GCCCGTGCTG CCCGAAAATG ATCCGTGCCT CATATTGAGG CCCAGACACG GCCCAATAAT     900

ACCGGGTTGG AGGGCCGGGC CCAAAATTGA CGCCCCTAAA AAAATACCTC TTCATAGATA     960

TTATATTAAC TGGGAATCAT CGGCCTCCAC TAATCTTGAA TATTAAGGTT AATTATCTAT    1020

TAACAAGTGC GTTCACGAAT TTTAAATCAT TGATCGGAGA CACGTAAAAG GAAATTCGAC    1080

TTTCCAATTA TTTTCTAAAG CATCTCTAAT ATTGCACATA AATAAGACAG CTAGCCGCAA    1140

GAACAGGTTG GCATTTACTA AAAGAATAAT AGTCTCGTTA GTTACAAAGT TGGTCGTTTT    1200

TTGTCGCTCT CAGGTTATTA ACATAGCATG TATGAATTCT GAGCTTCATT TATTAATGTT    1260

ATTGCAAAAG ATCGATGAAG CATTTAGTTT GCACCGGAAA TTTAAATTTA CATATCTTAA    1320

CCCACATAAT TTTATTTGTA ATGGCGACTC GATTCAAATC GATTTCATGT GACGGGATTG    1380

AAATTTGAAA CGTATGTAAA TACCAACTCC GGAGATGCAT CAGTTTATAA GATAGGCTTA    1440

TTTCAAGTGG ACATCGTCTA GATAGGCTTT ATTATACCGA GTCAATAAAA ATTCATCTTC    1500

ATCGATTAGA AAGTGTAGAT TAATTAGGTC CGGGGTAGAG TACAATATTA GATGAGCAAT    1560

TTAACACATG ATTGTCACAT TTACTTGTGG ACTCCACAGC ATGTTATGTG TCTTGTACAA    1620

AAATGGACAT CGTCTAGATA GTCTTAATAA TACCGAGTCA ATAAAAATAC ATGTATTTAA    1680

TATGCCATGT TATGTAGGTT TGCTAGTAAC GTCTAATATT CTTGACAAAA ATGGTTTATG    1740

TGTATCGTAA TCATCGCGGC TGTTGAGGGC ACTCACGAAA ATGGGAACAT GCCTTTGCTC    1800
```

```
GGCGGATTAT ACAAAAACAA CAGCAGCCTC TATCGATCTA TCGCCTCTGA AAACCCAAAG    1860

TTCAATCTCC TATTAATATT GTTGCCATTG TAAGTTCATC ACGTAGTTCC CCTTAATTAA    1920

TATTACTTGA CAAGGAGAAC TAGAGTCGTA AGGACACACG GGATGGCGGG AATCGCCGGG    1980

ACTTGTTCTA CCGGAGTGCT CCTGAGAGGA AGAGATCAGT ACAATGGGCT CAGGCCGATG    2040

GAGAGCGTAA AGGTGGCAGT TCCCGTTACT AGGAAGATCT CTTCTACACC AAGTAAGAAA    2100

TGAAACTATA TCTTGAGCTA TTTACTTGTT ATGTTATGTT CCTGTGAATA CCGGGTTACA    2160

AACATGATGT GGTTGATGAA CTGATCAGCG CTATGATTTG TTATGTAATG AAATGGTTCG    2220

ACGTTTTTTC CTTGAAAGTT AGGAAGTATT TACATCGGTT TCGGCCTTAT TGCCTGCCCA    2280

ATATGTTTCA ATGCATCTTG TTCCATCTAT AGTGTCATGT TTCATTCATA GATCATGGTT    2340

AAGTTTATTG GCCTTTTTTT TCCTGAGTGC AGCACGGAGA ATCAAGGCCA TGGCCTCCCA    2400

G ACT GTC TCG CCT CCA AAG CGG GAG AAA GAT CCC AAG AAG AGG ATT       2446
  Thr Val Ser Pro Pro Lys Arg Glu Lys Asp Pro Lys Lys Arg Ile
   1               5                  10                  15

GTA A                                                                2450
Val
```

(2) INFORMATION FOR SEQ ID NO: 10:

(i) SEQUENCE CHARACTERISTICS:
        (A) LENGTH: 287 Base pairs
        (B) TYPE: Nucleic acid
        (C) STRANDEDNESS: Double stranded
        (D) TOPOLOGY: linear (ii) MOLECULE TYPE: DNA (genomic)

(iii) HYPOTHETICAL: NO (iii) ANTI-SENSE: NO (vi) ORIGINAL SOURCE:
        (A) ORGANISM: Cuphea lanceolata (vii) IMMEDIATE SOURCE:
        (A) LIBRARY: genomic Lambda FIX II
        (B) CLONE: ClKASIg8

(xi) SEQUENCE DESCRIPTION: SEQ ID NO: 10:

```
ATGCAGCGTA GTTGTATAGA TGACAACCGC AGTTTCCCCG GCCGGCGGGC ACTTTCTCCG     60

GGTAAGCACT AAAAGGGTTC CTCTTGCTCT TCATCAGAAG GTCGAAAGCA GCCATCTTTC    120

CTTCCTTCTT CCTCTCCTCC CTGTCCCTCT GGATGAAAGG GGTATTACTG AGGGACCGGG    180

CTTTTTCCGC CTGTCACCGA AGATGACTTC AGCTCTGGGT TTTTTGCTCC GCCCTCGTTT    240

CTGGGACGCA GAGAACTGTA GTTTTTTTTT AAGGTCTTTT CCCCACG                 287
```

(2) INFORMATION FOR SEQ ID NO: 11:

(i) SEQUENCE CHARACTERISTICS:
        (A) LENGTH: 693 Base pairs
        (B) TYPE: Nucleic acid
        (C) STRANDEDNESS: Double stranded
        (D) TOPOLOGY: linear (ii) MOLECULE TYPE: DNA (genomic)

(iii) HYPOTHETICAL: NO (iii) ANTI-SENSE: NO (vi) ORIGINAL SOURCE:
        (A) ORGANISM: Cuphea lanceolata (vii) IMMEDIATE SOURCE:
    (A) LIBRARY: genomic Lambda FIX II
    (B) CLONE: ClKASIg8

(xi) SEQUENCE DESCRIPTION: SEQ ID NO: 11:

```
TGGAAGGTGG TGGGGAAAAT GGGTGGAGGA GGTTTAGTCT GGGACTTGGA GGGTTTTGTG      60
GCAGTTTTGT TGGCTGCCTT TGGGGCCTAT GAACTGAACG TGTGGTGGCT ATCCCGCCAA     120
AATCTGCGCC TCATCGCATA AGACACCGAT GGCCATGACA TTGTCTCAAA CCTGCGCAAG     180
GATATCATTT CTTGGACGTT GTCGTGGCTC GGTTTTTTTG TTACTATGTT ATGTAAATAT     240
CTCAATTTGC CCGACTAGAT TTGGCCTCAT ATTTCGATAC AACTCATCTA AACATCTCGA     300
ATCCGATAAG CCTATTCAAT TGGGAATTGC CTCATTGCTA AGGTAGCTGT GGATTCAATG     360
ATTACTTGAT AGACAAGCAA CTAATGGCGA ACATGGTCAC GGGTTTTCTC CTTTCACCCC     420
CCAAACTGCT ATACAATGCA AAGATCTCTG AAGCAATTAT CTCTTTGAAC CTCCCGGGAT     480
TGCGTTTTTT TCTTTCTATT TGGTACCTGA CACATCAAGA CAACCGCAGT TTCCCCGGCC     540
GGCGGGCACT TCTCCGGGTA AGCACTAAAA GGGTCCCTCT TGCTCTTCAT CAGGGTTATT     600
GTCTCATGAG CGGATACATA TTTGAATGTA TTTAGAAAAA TAAACAAATA GGGGTTCCGC     660
GCACATTTCC CCGAAAAGTG CCACCTGACG TCT                                 693
```

(2) INFORMATION FOR SEQ ID NO: 12:

(i) SEQUENCE CHARACTERISTICS:
        (A) LENGTH: 564 Base pairs
        (B) TYPE: Nucleic acid
        (C) STRANDEDNESS: Double stranded
        (D) TOPOLOGY: linear (ii) MOLECULE TYPE: DNA (genomic)

(iii) HYPOTHETICAL: NO (iii) ANTI-SENSE: NO (vi) ORIGINAL SOURCE:
        (A) ORGANISM: Cuphea lanceolata (vii) IMMEDIATE SOURCE:
        (A) LIBRARY: genomic Lambda FIX II
        (B) CLONE: ClKASIg8

(xi) SEQUENCE DESCRIPTION: SEQ ID NO: 12:

```
ATCTGACTTT AATTCTAAAA GACTGGATAC GGTGACGATT CTCGACAGAG AACTCGGAGT      60
CATCATCGCT ACCACACTTT TTTGTTGGCA AAATTTAGAT CGCCGTCACC CCATCTTCAC     120
TAGCCCATAT AAAATATATA TTTTTTACCT TACCAAATTT TTTTTTTTAT TCTGTAAAAT     180
AAAACCAAAT TGAATTATTA AGATCATAGA TTTAACAAAA TTTTAGTAAT TAATTAATTA     240
CTAAAACTTT ATTAATTGTT GTAATAAACG ATCTATATTT ACTAATAAAT AATCGAATGA     300
CATATGAATG GAAGTACCTA TAATTTCAAT TGTCATTGAA ACACTTTAAA AATCATTATT     360
AAATATAAAA ATGAGTTGCT AGATTAGAT TATATTTTTT CTAAACTATA AATTAGGTTT     420
CCTTTGAGTA CAAAATCATC TAAAAATACT TAAAGGAGTA AAAACATGTA AAGACTAGG     480
GGTGGCAAAA AAGACCAGGC GACCGTACGA AAATTTTCAG ACCGGCTTGA GCCCCACCCC     540
CGATAATATA TTTCTGTAAA AATT                                           564
```

(2) INFORMATION FOR SEQ ID NO: 13:

(i) SEQUENCE CHARACTERISTICS:
        (A) LENGTH: 290 Base pairs (B) TYPE: Nucleic acid
        (C) STRANDEDNESS: Double stranded
        (D) TOPOLOGY: linear (ii) MOLECULE TYPE: DNA (genomic)

(iii) HYPOTHETICAL: NO (iii) ANTI-SENSE: NO (vi) ORIGINAL SOURCE:
        (A) ORGANISM: Cuphea lanceolata (vii) IMMEDIATE SOURCE:
        (A) LIBRARY: genomic Lambda FIX II
        (B) CLONE: ClKASIg8

(xi) SEQUENCE DESCRIPTION: SEQ ID NO: 13:

TTTATAGGAA ATATATCTCT ACTAATATAT TAAGAAACTT TTGTTTGTTC TCACTATTTT      60

GTTTTTTCAA TTTTACTATT TTAATTTTAT TTTTCTCATT CTTTCCATTA CTATTTGATT     120

TTTTTCCTTT AATAACCAAA ATATCCATTC ATATTTTTAC TTTTTATAAA TATATTTTTC     180

TTATTAAATT TACTTTTTAT TTATTTTTTA TTCGCTTTTA ATTTTTTATA CAAATCTAAT     240

AATCTTTTTT ATCTGCGGAT CAACCGCTTG TATATTAATA TAACTTTTAT                290

(2) INFORMATION FOR SEQ ID NO: 14:

(i) SEQUENCE CHARACTERISTICS:
        (A) LENGTH: 246 Base pairs
        (B) TYPE: Nucleic acid
        (C) STRANDEDNESS: Double stranded
        (D) TOPOLOGY: linear (ii) MOLECULE TYPE: DNA (genomic)

(iii) HYPOTHETICAL: NO (iii) ANTI-SENSE: NO (vi) ORIGINAL SOURCE:
        (A) ORGANISM: Cuphea lanceolata (vii) IMMEDIATE SOURCE:
        (A) LIBRARY: genomic Lambda FIX II
        (B) CLONE: ClKASIg8

(xi) SEQUENCE DESCRIPTION: SEQ ID NO: 14:

CCTAAAAAAA CACCTTCTTT ATAGATATTA TGGTAACTGG GAATCATCTG CCTCCACTAA      60

TCTGAATATT AAGGTTAATT ATCTCTTAAC AAGTCGTTCA ACGAATTTTA AATCATTGAT     120

CGGAGACACG TAAAAGGAAA TTCGACTTTC CAATTATTTT TTAAAGCATC TCTAATATTG     180

CACATAAATA AGACAGCTAG CCGCAAGAAC AGGTTGGCAT TTACAAAAAG AATAATAGTC     240

TCGTTA                                                                246

(2) INFORMATION FOR SEQ ID NO: 15:

(i) SEQUENCE CHARACTERISTICS:
        (A) LENGTH: 227 Base pairs
        (B) TYPE: Nucleic acid
        (C) STRANDEDNESS: Double stranded
        (D) TOPOLOGY: linear (ii) MOLECULE TYPE: DNA (genomic)

(iii) HYPOTHETICAL: NO (iii) ANTI-SENSE: NO (vi) ORIGINAL SOURCE:

(A) ORGANISM: Cuphea lanceolata (vii) IMMEDIATE SOURCE:
            (A) LIBRARY: genomic Lambda FIX II
            (B) CLONE: ClKASIg8

(xi) SEQUENCE DESCRIPTION: SEQ ID NO: 15:

AGAATATGCA TCAGTTTTAT AAGATAGGCT TTATTTCAAG TGGACATCGT CTAGATAGGC      60

TTTATAATAC CGAGTCCATA AAATTTCATC TTCATGATTA GAAAGCGTAG ATTAATTAGG     120

TCCGGGGTAG AGTACAATAT TAGATGAGCA ATTTAACACA TGATTGTCAC ATTTACTTGT     180

GGACTCCACG GCATGTTATA TGTCTTGTAC AAAAATGGAC ATCGTCT                   227

(2) INFORMATION FOR SEQ ID NO: 16:

(i) SEQUENCE CHARACTERISTICS:
            (A) LENGTH: 438 Base Pairs
            (B) TYPE: Nucleic acid
            (C) STRANDEDNESS: Double stranded
            (D) TOPOLOGY: linear (ii) MOLECULE TYPE: DNA (genomic)

(iii) HYPOTHETICAL: NO (iii) ANTI-SENSE: NO (vi) ORIGINAL SOURCE:
            (A) ORGANISM: Cuphea lanceolata (vii) IMMEDIATE SOURCE:
            (A) LIBRARY: genomic Lambda FIX II
            (B) CLONE: ClKASIg8

(ix) FEATURE:
            (A) NAME/KEY: Startcodon
            (B) LOCATION: 66..68

(ix) FEATURE:
            (A) NAME/KEY: CDS ( incomplete transit peptide )
            (B) LOCATION: 66..150

(xi) SEQUENCE DESCRIPTION: SEQ ID NO: 16:

CATCACGTAG TCCCCCTAAA TCAATATCAC TGACAAGGAG AACTAGAGTA GGAAGGACAC      60

ACGGG ATG GCG GGA ATT CGC GGG ACT TGT TCT ACG GGA GTG CTC TTG        107
      Met Ala Gly Ile Arg Gly Thr Cys Ser Thr Gly Val Leu Leu
       1               5                  10

AGG GGA AGA GAT CAG TAC AAC GGG CTC AGG CCG ATG GAT AGC G             150
Arg Gly Arg Asp Gln Tyr Asn Gly Leu Arg Pro Met Asp Ser
 15              20                  25

TAAAGGTGCC AGTTCCCGTT ACTAGGAAGA TCTCTTGTAC ACCACGTATG AAATGAAACT     210

ATATCTTGAG CTATTTACTT GTTATGTTAT GTTCCTGCGA ATACCGGGTT ACAAACATGA     270

TGTGGTTGAT GAACTGATCA GCGCTATGAT TTGTTATGAA ATGAAATGGT TCGACGTTTT     330

TTCCTTGAAA GTTAGGAAGT ATTTACATCG GTTTCGGCCT TATTCATAGA TCATGGTTAA     390

GTTTAATGGC CTTTTTTTCT GATCTGCAGC ACGGAGAATC AAGGCCAT                  438

(2) INFORMATION FOR SEQ ID NO: 17:

(i) SEQUENCE CHARACTERISTICS:
            (A) LENGTH: 1350 Base pairs
            (B) TYPE: Nucleic acid
            (C) STRANDEDNESS: Double stranded
            (D) TOPOLOGY: linear (ii) MOLECULE TYPE: DNA (genomic)

-continued

```
    (iii) HYPOTHETICAL: NO (iii) ANTI-SENSE: NO (vi) ORIGINAL SOURCE:
          (A) ORGANISM: Cuphea lanceolata (vii) IMMEDIATE SOURCE:
          (A) LIBRARY: genomic Lambda FIX II
          (B) CLONE: ClKASIg13

(ix) FEATURE:
          (A) NAME/KEY: Startcodon
          (B) LOCATION: 473..475

(ix) FEATURE:
          (A) NAME/KEY: CDS ( mature protein )
          (B) LOCATION: 1075..1350

(xi) SEQUENCE DESCRIPTION: SEQ ID NO: 17:

CACGCATTGA GAAGGATATG GTGACCTCAT AATTAAATCC CGACTAATTT GATTTCGCTT      60

CGGATCGCAC ACCTACACGT GGTGAGTGAG GCTCCTAAAA ATATTTTCTC CATTCACTTA     120

TAAATTTATC TGTAAGTGGG CGACACTCAA ATTTATTTTC ATGTGACATT TACTTGTGTA     180

CTCCAACGGC ATAATTAATG TATGGCCATT TCATATGCCA TCTTATGTTG GTTTGTTAGT     240

AACGTCTAAT ATTTTCATGA CAAAAAAGGT TTATGTGTTT CGGGATCATC GACGCCGTTG     300

AGGACATGCC TTTGCTTGGC GGATATACAA ACATCAGCAC CTCTATGGAT CAATGCCTCT     360

GAAATCCAAT GTTCATCCCC TATTAATAAT ATTGCCATTG AATTTCATCA CATAGTTCCA     420

CTCGTAATAT TTTACTTAAC AAAGGAGAAC TTGAGGTAGG AAAGGACACG GGATGGCGGG     480

AATCACCGGA CTTGTTCTAC CGGTGTGCTG CTGCGGGGAA GAGAGTCGGG GACCGTCAAT     540

GGGGTTGCTT CCCTGACTCA GTTCAATGGA CTCAGGCCGA TGGAGAGCGT GAAGATGGCG     600

GTTCCGGCAA CTAGGAAGAT CTCTTCTACG CCGTGTAAGA TTGAAAACAA TAGCTTGAGC     660

TCTTTATTGT TTGGTTATGA CAAAGTCGTG CCATTTATGT TTATGTATGT TCCTGCCAAT     720

ACCGGGTTAC AAACATGATA TGGTTGATGA ACTGATCACT ATAACTTGTT ATGAGATGAG     780

TTGGATCGAC ATTTTTAATT TGAAATTTAG GAAGCATTTG CATCGGCTTC GGCCTTAATT     840

TTACTTGCCT AATATGTTTC AATGCATCTT TTCACTCAAC CGGATCACTT GTTGAGGCGG     900

ACAATGGTCG AAGGTTTCAA ACATGTTTGT CTAGAGTTTG GATGTCTTTC AAGTTTGGTG     960

TCTTGTTTCA TTCATAGATC ATGATTAAGT TTAATGGCTT TGGCCTTGTT TTTTTTATTT    1020

TCCTGATGTG CAGTACGGAA ATGCGGGGGA AGGATCAAGG CCATGGCTTC CCAG ACG       1077
                                                            Thr
                                                             1

GGC GCA CGT CCT AAG CGG GAG AAA GAT CCC AAG AAG AGA ATT GTA ATA      1125
Gly Ala Arg Pro Lys Arg Glu Lys Asp Pro Lys Lys Arg Ile Val Ile
          5                  10                  15

ACG GGG ATG GGA CTT GTA TCT GTT TTC GGT AAC GAC ATC GAC ACT TTC      1173
Thr Gly Met Gly Leu Val Ser Val Phe Gly Asn Asp Ile Asp Thr Phe
         20                  25                  30

TAC AAC AAG CTC CTG GAG GGG GAG AGT GGA ATC AGC ATC ATT GAT AGG      1221
Tyr Asn Lys Leu Leu Glu Gly Glu Ser Gly Ile Ser Ile Ile Asp Arg
     35                  40                  45

TTT GAT GCC TCG AGC TTT TCC GTG AGG TTT GGT GGC CAG ATC CGT GAT      1269
Phe Asp Ala Ser Ser Phe Ser Val Arg Phe Gly Gly Gln Ile Arg Asp
 50                  55                  60                  65

TTC TCC TCC AAG GGG TAC ATA GAC GGG AAG AAT GAT CGT CGC CTT GAT      1317
Phe Ser Ser Lys Gly Tyr Ile Asp Gly Lys Asn Asp Arg Arg Leu Asp
                 70                  75                  80
```

```
GAC TGT TGG AGG TAC TGC TTA GTT GCA GGC AAA                           1350
Asp Cys Trp Arg Tyr Cys Leu Val Ala Gly Lys
         85                  90
```

(2) INFORMATION FOR SEQ ID NO: 18:

(i) SEQUENCE CHARACTERISTICS:
        (A) LENGTH: 1141 Base pairs
        (B) TYPE: Nucleic acid
        (C) STRANDEDNESS: Double stranded
        (D) TOPOLOGY: linear (ii) MOLECULE TYPE: DNA (genomic)

(iii) HYPOTHETICAL: NO (iii) ANTI-SENSE: NO (vi) ORIGINAL SOURCE:
        (A) ORGANISM: Cuphea lanceolata (vii) IMMEDIATE SOURCE:
        (A) LIBRARY: genomic Lambda FIX II
        (B) CLONE: ClKASIg19

(ix) FEATURE:
        (A) NAME/KEY: Startcodon
        (B) LOCATION: 521..523

(ix) FEATURE:
        (A) NAME/KEY: CDS ( mature protein )
        (B) LOCATION: 956..1141

(xi) SEQUENCE DESCRIPTION: SEQ ID NO: 18:

```
CAAGTGGACA TCGTCTAGAT AGGCTTTATA ATACCGAGTC AATAAAAATT CATCTTCATC      60

GATTAGAAAG TGTAGATTAA TTAGGTCCGG GGTAGAGTAC AATATTAGAT GAGCAATTTA     120

ACACATGATT GTCACATTTA CTTGTGGACT CCACGGCATG TTATGTGTCT TGTACAAAAA     180

TGGACATCGT CTAGATAGGC TTAATAATAC TCGAGTCAAT AAAAATACAT GTATTTAATA     240

TGCCATGTTA TGTAGGTTTG CTAGTAACGT CTAATATTCT TGACAAAAAT GGTTTATGTG     300

TATCGTAATC ATCGCGACGT TGAGGGCACT TACGAAAATG GAACATGCC TTTGCTCGGC      360

GGATTATACA AAAACAACAG CAGCCTCTAT CGATCTATTG CCTCTGAAAA CCCAAAGTTC     420

AATCTCCTAT TAATATTGTT GCCATTGTAA GTTCATCACG TAGTTCCCCT TAATTAATAT     480

TACTTGACAA GGAGAACTAG AGTCGTAAGG ACACACAGAC ATGGACGGAA TACGCCGGAC     540

TTGTTCTACC GGAGTGCTCC TGAGGGGAAG AGATCAGTAC AATGGGCTCA GGCCGATGGA     600

TAGCGTAAAG GTGGCAGTTC CCGTTACTAG GAAAATCTCT TCTACACCAA GTAAGAAATG     660

AAACTATATC TTGAGCTATT TACTTGTTAT GTTATGTTCC TGCGAATACC GGGTTACAAA     720

CATGATGTGG TTGATGAACT GATCAGCCCT ATGATTGTTA TGAATGAATG GTTCGACGTT     780

TTTTCCTTGA AAGTTAGAAG TATTTACATC GGTTTCGGCC TAATTGCCTG CCCAATATGT     840

TTTAATGCAT CTTGTTCCAT TGAAGTGTC ATGTTTCATT CATAGATCAT GGTTAAGTTT      900

ATTGGCCTTT TTTTTGCTGA TCTGCAGCAC GGAGAATCAA GCCATGGCCT CCCAG ACT      958
                                                               Thr
                                                                 1

GTC TCG CCT CCG AAG CGG GAG AAA GAT CCC AAG AAG AGG ATT GTA ATA      1006
Val Ser Pro Pro Lys Arg Glu Lys Asp Pro Lys Lys Arg Ile Val Ile
           5                  10                  15

ACG GGG ATG GGT CTT GTA TCT GTT TTC GGG AAC GAC ATT GAC ACT TAC      1054
Thr Gly Met Gly Leu Val Ser Val Phe Gly Asn Asp Ile Asp Thr Tyr
         20                  25                  30

TAC AAC AAG CTC CTT GAG GGG GAG AGT GGA ATC AGC ATC ATT GAT AGG      1102
```

```
Tyr Asn Lys Leu Leu Glu Gly Glu Ser Gly Ile Ser Ile Ile Asp Arg
     35                  40                  45

TTT GAT GCC TCG AGC TTT TCC GTG AGG TTC GGT GGC CAG                    1141
Phe Asp Ala Ser Ser Phe Ser Val Arg Phe Gly Gly Gln
 50                  55                  60
```

(2) INFORMATION FOR SEQ ID NO: 19:

(i) SEQUENCE CHARACTERISTICS:
        (A) LENGTH: 3750 Base pairs
        (B) TYPE: Nucleic acid
        (C) STRANDEDNESS: Double stranded
        (D) TOPOLOGY: linear (ii) MOLECULE TYPE: DNA (genomic)

(iii) HYPOTHETICAL: NO (iii) ANTI-SENSE: NO (vi) ORIGINAL SOURCE:
        (A) ORGANISM: Cuphea lanceolata (vii) IMMEDIATE SOURCE:
        (A) LIBRARY: genomic Lambda FIX II
        (B) CLONE: ClKASIg20

(ix) FEATURE:
        (A) NAME/KEY: Startcodon
        (B) LOCATION: 3068..3070

(ix) FEATURE:
        (A) NAME/KEY: CDS ( mature protein )
        (B) LOCATION: 3661..3750

(xi) SEQUENCE DESCRIPTION: SEQ ID NO: 19:

```
AGAGAAGCCT CGGCTTCCTT AACAATTTCC TCAATGACTG ACTCCTTGTG TATGGTCTCC      60

CTGCACATGA TGCTTCCTAT CACGAATGGG GTTAGCCCTT TCTCTACCCC TTTCTTGAGA     120

AGCATGGTGG AAATCCGTAG AGTTCGAGCA CATTCAGTCG GGACTTCCCA CCCGAAGAAC     180

TTCAGCATCG CAATGTCTTC TCCGCGTCAA GGGATCTTAT GTATTCCACG GTGTTAGGGG     240

AGAATGGCTG TTTGGCTTGT GGCCAGTAGA GCCAGTCGAA GGTGCAATCT TCAAACTGTA     300

AGAGAATAAT GGAGAGATAT GTCAGCATAT TATGCCCGGA ATATGGTAAA AGACGACTAG     360

CCAAGGGAAA CTCACATTCT CAGGAAGACA GTAGCCATGG TCGACTATGA CATGGTCTCA     420

AATGTGCGCC AAGGATATCA ATTCTTGGAC GTTGTCGTGG CTCATTTTTC ATGTCACGTA     480

AATATCCCAA TTTTCCTGAC TAGATGTGGC CTCATATTTT GATACAACTT TATCTAAGGG     540

TAACCTGATC AATTCATGCT TGTGCTTGCT CGATTCAGTA TTTAGAATTA CAATGAAATT     600

CAATCCGACA TAGCTATGGT AGCTGTGGAT TTGATGATAA CTTGATAGAC AAGTATGATC     660

AATGTTCAAT TATATCGGGT TCCTTCCGAT TTTATACTGT CAAAGCAACT AATGGCGAAC     720

ATGGTCGACT TGCACCGGTT CTCTCCTTTC ACCTCTGAAC TGCTGCACAA TACATCCTGG     780

TAATGATACA TCCTAGAGTT AGTAGGAGAA TCAATGGATA CTAATAGTAT GACGATCCCA     840

TGTAGAGAGT TCAATGATAA AAAAAAGGGG ACAATGTATG CAATGAAGCA AGCCAAATTC     900

GAAGTGAATC CCGCTTTCTT ACCCCATTTA ACATAACAAA GGATAACATT GATATTCAAG     960

CATGTATCTG AAGAATCTTT TGGTATTTGA TACTCACTTA AACGGAGTTA ATCCGATGTT    1020

CTGGATGTAA CTATTTGAAC AAGAAATTTA CCGAAAAAGA AACAAGATTG ATTGGGGATA    1080

AGCCAAGGTC AAGAATAACA TACCTTGCTC AGATTCATCC TAGCTGTCCT CCTCTCCCAG    1140

AAACCAACCT CATCCATGCT TTGGCGCCTC CTGAAGTACC TACCCCCAGA AGCTACGAAA    1200
```

```
CCCGGGCAAG GCCTGTAAGC TTTGATAGGC CACCAACCAA AGCCAGGGAC TGTCGCAATG    1260

CCTCCTTGAA TCCTCCCCTC TCCATTGCAT CCTCTCTCGA TTTCAGCCTT ACCACAGGCC    1320

TTACATCCAC TGCCACTGCA AAAATCAAAC CGAATTCACC AACATGTTGG ATAGCCATAC    1380

GTCCGTGCAA ATATATTATG CATCTCCGCA CTACCCTCAT GCATCTAAAA GTAAGCATTA    1440

ATAATACTAA ATGCACAAAC TACAACTACC ATCCAACTAT TGCCAAGGAT TTTGCTTCTT    1500

CTGTTCAACA CATACATAAT TACCGAACCC AGCTTTTGAT GATTAATCTC GATCAGCCCT    1560

CGACAAGTAA CGGCGGAGAT TTAGTGAATG ATAATAAACC TCGCGAAACC TCATAACAAG    1620

CCACGCAAAG CATTTTCAGG AAGATTGCAT CAGTAGTAGT TGGCTGAGCT CAACAACTCT    1680

AAAAACACAC ACACACATTG TGCCCAGAAA TGATTACATA ACAATTAAAT TTACAGTTCA    1740

ATGTAAAAAA AGCTTCATTT TTCGACTGCT TGACAATCAT ACGACCGGAA CAAAACAATA    1800

AACGACAGCA ATTGACGATG TTCTTTTATT CAAAACTGGT GAAATTCATT CAAGGAAAGG    1860

TTTTGCAGCT ACCAATCCTA CTCAAGCATG CATCCAACAA GTTAAGATTT TAAGGCATT    1920

AATGAAAAAG GGTCGACCTG AAAGGGGATC CATCGCCGGA ATCAAGTGAT TGGGAGGGAG    1980

GAGGGGAAAA GGGTTCTTCG TCTACAGCGG GAGGGGGAGG GGAAGAAGTG GAAGCAGAAC    2040

AGGGAGGGGG TTTGACAGTG AGCTTGGAGG GTGGAGGGAG CCAGACGAAG GGCGATGGAC    2100

CATTCAACGG AGAAGCGGAG AGACGAAGGT GAGGTTGAGA AACGGAGCGG CAGTTTGGGA    2160

AGAGAGGAGA TGAAGACATC ATCGCCATTC TTCCTCTGCC TCTGCAACTG ACACACTCTC    2220

TCCCGCTTCT CTTCTCCAAA TAATGAGGAT AATGGCTGGC CACAAATTAT TAATTAATTT    2280

AAGAGAATTA AATAAGGTAA TATAATTTTA AATATTTTAT ATGAAGTTAT ATAAATCATG    2340

TTAAAGAATT TGATCATTTA ATTTTTTTTA TTATTAATTT AAACGAAAAA TTAAAATGAA    2400

AAAGTCAACA TACGTTCATA AAATTATGAA CAATGTTTTT CTACTTTTAT TGATATTTTA    2460

TTTTCATTTA TTTATACTAT CTAATTGTTA ATTTATATT ATTTGCATAA ATTTAATATA    2520

CACATCATGG TCACATTTTT AATTATAAGA TTTTTTTTAT TTGAAATAGA ATAGTTTCTA    2580

TTTTTAATTG TTATTTTAGT TTTTTATATA TATTTTAATA GGTAATTTTC GTAAATTTTA    2640

AAGTGATGAT AACGTACCAC TACTTTTATT GATTGCACCC CAATATTTGC GTATCCTAAC    2700

CCATATAAAT TTTATTTGTA AGTGGGCGAC ACTCAAAATT GATTTCATGT GACATTTATT    2760

TGTGGACTCC ACGGCATAAT ATAAGTTTGC AACTTCATAT GCCATCTTAT GTTGGTTTGT    2820

TTGTAACGTA TAATATTTTT TCAAGACAAA AAAGGTTTAT GTGTTTCGGG ATCATCGACG    2880

CCGTTGAGGG ACATGCCTTT GCTTGGCGGA TTATACAAAA ACATCAGCAC CCTCTATGGA    2940

TCAATGGCCT CTGAAAATCC AATGTTTCAT CCCCTATTAA TAATATTGCC ATTGAATTTT    3000

CATCACATAG TTCCACTCGT AATATATTAC TTGACAAAGG AGAACTTGAG ATAGGAAAGG    3060

ACACGGGATG GCGGGAATCA CCGGGACTTG TTCTACCGGT GTGCTGCTGA GGGGAAGAGA    3120

GTCGGGGACC GTCAATGGGG CTGCTTCCCT GACTCAGTAC AATGGACTCA GGCCGATGGA    3180

GAGCATGAAG ATGGCGGTTC CGACAACTAG GAAGATCTCT TCTACGCCGT GTAAGATTGA    3240

AAACAATAGC TTGAGCTCTT TATTGTTTGG TTATGACAAA GTCGTGCCAT TTATGTTTAT    3300

GTATGTTCCT GCCAGTACCG GGTTACAAAC ATGATATGGT TGATGAACTG ATCACTATAA    3360

CTTGTTATGA GATGAGTTGG ATCGACATTT TTTATTTGAA AGTTAGGAAG CGTTTGCATC    3420

GGCTTTGGCC TTATTACTTG CCTAATATCT TTCATGCATT TTTTCACTGA ACCGGATCAC    3480

TTGTTGAGGC GGATGGTGGT CGAAGGTTTC GAACATGTTT GTCTTGAGCT TGGATGTCTT    3540

CCAAGTGTGG TGTCCTGTTT CATTCATAGA TCATGATTAA GTTTAATGAC TTTGGCCTTG    3600
```

```
TTTTTTTCCT GATGTGCAGT ACGGAAATGC GGGGGAAGGA TCAAGGCCAT GGCTTCCCAG      3660

ACG GGC GCA CGT CCT AAG CGG GAG AAA GAT CCC AAG AAG AGA ATT GTA       3708
Thr Gly Ala Arg Pro Lys Arg Glu Lys Asp Pro Lys Lys Arg Ile Val
 1               5                  10                  15

ATA ACG GGG ATG GGA CTT GTA TCT GTT TTT GGT AAC GAC ATC                3750
Ile Thr Gly Met Gly Leu Val Ser Val Phe Gly Asn Asp Ile
              20                  25                  30
```

(2) INFORMATION FOR SEQ ID NO: 20:

(i) SEQUENCE CHARACTERISTICS:
        (A) LENGTH: 1570 Base pairs
        (B) TYPE: Nucleic acid
        (C) STRANDEDNESS: Double stranded
        (D) TOPOLOGY: linear (ii) MOLECULE TYPE: DNA (genomic)

(iii) HYPOTHETICAL: NO (iii) ANTI-SENSE: NO (vi) ORIGINAL SOURCE:
        (A) ORGANISM: Cuphea lanceolata (vii) IMMEDIATE SOURCE:
        (A) LIBRARY: genomic Lambda FIX II
        (B) CLONE: ClKRg2

(ix) FEATURE:
        (A) NAME/KEY: TATA-Signal
        (B) LOCATION: 1412..1429

(ix) FEATURE:
        (A) NAME/KEY: Transcription start
        (B) LOCATION: 1445

(ix) FEATURE:
        (A) NAME/KEY: Startcodon
        (B) LOCATION: 1512..1514

(ix) FEATURE:
        (A) NAME/KEY: CDS
        (B) LOCATION: 1512..1570

(xi) SEQUENCE DESCRIPTION: SEQ ID NO: 20:

```
TGTTGTCGAC TCAGGTCATT CGCTTTCCAT CATTTCTTTT GTCATATCTT CTGTTAAATC        60

TCAGTAATGA CAACTGGATT CACGGATATT ATGGTCTTCG AATAAATTTG CTTTTGAGAT       120

GAAAAACTAT TTGAATGCTG CTTTGATGAT GATCGAGTCA TTGGTATTTC ACTTACTTGA       180

CTTAATATTT TCGTTTGTTT AGGAAGAGTT ATAGTTCATG CTCTCGAGGA GAAAGCTAGA       240

GCTTACTATA ACTTGGAAAG TCTTTGGACG TCTGAACCCC CGCTGAAGGA ATCCAAACAG       300

GTAATGTTAA AGCTGCATGG AATGTATGCC GTTGTTTCTT GCGCTATGCA ATTTTAAATG       360

TTCAATCGGG CATCTACTTT GCAATACATA TGAAAAGGAG ATATAATGTC GTTTTGATAT       420

CCTACCTCTT TCTCGACAAC CATTGAAAAC TGTGTACTGG ATTTATTGTA ATTGGGACCC       480

AATTTCCTCA CACACTCTCG CGGGCCTCGG AGTTATACTG TCCGAGAGGT CATAATTTAG       540

TGGTTTGTTT TGAAATAAGC CGCCCTTACG TGCAATTCTC ATTTGGTGAT TTGAATGTAC       600

TCATTTGGGT TCCCTCATGC ATTATTATGA GCTTATATAG AATTGATAAA TGTAGTAGAT       660

TGGATACAAT AAGATCTGTA CTTCCAGTCA GACAAGAACA CTTTCTATTT GCTGTGCTG       720

TTTTGATAAA CCAAATCATC GATTCTTTTC CATCCAAATAT GTTGTCTGGA AAACCCTTTT       780

ATTTTTTCCT CTGGTTGTGT CTCATCTTGC GACGATGGCA TGAGAATGCA TTCCTAACAG       840
```

```
-continued

CTACCTTCAT CTTGGTCAGG ATTTGGATAA AGCTTTTGTG AAGATTCGTC CTAAGAACAA      900

CTCCAAGAAA CCATCCAAGC TCTCTGTCTA AGATATAGTT CACATAATCA CTCCCAGATT      960

TCGTCACCTG GTACTTTTAT TCCTAAGACA AATGAGGTTT ATTTCTTCAT ATATCCAATT     1020

CCAATGATCC AATGTTAGTA TTTCAATAGT AAATTCAACT TTCAACTACT CATATCGACG     1080

GCCTTTCAGA CAAAAAATTA TGAAAAAAAA TCATCAGGGT TAGCCAACGT TCGTTCTGTG     1140

ACAGATTTGA AATTTCGGGT AGATATCATA TGGGTGAGCC AACGGTCACT TGATGAGATC     1200

AGACAAATGA CGTCAGGGTT AGTGGGTGAT CTGTAAATAA GAGAACAATG TGAGGGCAGT     1260

TATGTCATTT AAAAAAGCCC CGCAAGGTCC TGAGCTGAGC CGAGCCTCGT TTCCATCGCC     1320

TCAACCATTC TTCTCTCGGA GCTCCCAAAG CTCGCTCTCT CTCTCTCTCT CTCTCTCTCT     1380

CTCTCGCTCC TCTTCCTTCC ATTCTTTCGC CTATATATAT ATATATATAC TTAGTTTCAG     1440

TTCCATTTTC ATTTCTGGCT TCCTTCTTGT TCGCCCGATC TCCTTCCCTC CTCCCTCTCC     1500

GTAGACTCGC C ATG GCC GCC GCC GCC GCC GCC GGT TGT TCC GGC GCT GTC     1550
             Met Ala Ala Ala Ala Ala Gly Cys Ser Gly Ala Val
               1               5                  10
GCT CTT AAG TCG CTC GGA GG                                            1570
Ala Leu Lys Ser Leu Gly
        15

(2) INFORMATION FOR SEQ ID NO: 21:

(i) SEQUENCE CHARACTERISTICS:
        (A) LENGTH: 926 Base pairs
        (B) TYPE: Nucleic acid
        (C) STRANDEDNESS: Double stranded
        (D) TOPOLOGY: linear (ii) MOLECULE TYPE: DNA (genomic)

(iii) HYPOTHETICAL: NO (iii) ANTI-SENSE: NO (vi) ORIGINAL SOURCE:
        (A) ORGANISM: Cuphea lanceolata (vii) IMMEDIATE SOURCE:
        (A) LIBRARY: genomic Lambda FIX II
        (B) CLONE: ClKRg3

(ix) FEATURE:
        (A) NAME/KEY: TATA-Signal
        (B) LOCATION: 827..838

(ix) FEATURE:
        (A) NAME/KEY: Transcription start
        (B) LOCATION: 864

(ix) FEATURE:
        (A) NAME/KEY: Startcodon
        (B) LOCATION: 916..918

(ix) FEATURE:
        (A) NAME/KEY: CDS
        (B) LOCATION: 916..926

(xi) SEQUENCE DESCRIPTION: SEQ ID NO: 21:

CTGCAGTATT ATGAAAAAGA ACTATAATGT CGGTTTCCAA TCCTACTACC TCTTCTCGAC       60

AACCATTGAA AATGAAACTA TTAGATGCTT GTTATGGATT TATAGTAGTT GAATTCCCAA      120

TGCACTTACC ATTGCCTCGA GTCATACTGT CTGATTGGTC AAAGCCGTTT GTTTTGAAGA      180

AGTCGCATCT TGCTGTAAAG TTTTCGTTAC GGTGATTTGA TATATTTGGG CTTCCTGATG      240

CACTTTTATG AGCTTATACA TGAATATTGA CACAACAAGA TCTGTATTGC TGTGCTGTTT      300
```

```
TGTTGAACCA AAACAGCGAT TATTTTGCCC TTCCGGTTTC ATTTCCTAAC AGCTTAAGTT        360

CATCTTGGTT AGGATTTGGA TAAAGCATTT GTGAAGATTC GGCCTAAGAA CAACTCCAAG        420

AAACCATCCA AGGTCTCTTC CTAAGATTGC ACCTGGTACT TTTGTTCCCG AGGTTTGTGT        480

GTGCTCATTT CTCCATGTAT CCTAGAGAAT GATCCTGTGA ATTGTCATTC CATGCCGATG        540

AGGAATCGAA GCCAATGTTT AGTACTTCTA TAATAAATTC CGGCATTCGA CATCTGATTT        600

TGGTAGATAA AATCTCAGGA TTTAACTTAC ACTAGAGGTT TGTACTGAAT CGAGTCAATT        660

CAATTATGGT ATGGGTGGGG GGCATGTAAT TAAGAGAACA AAAGGAGGGC AAATATGGAA        720

ATTGGGAGCC CTGCAAATTA GGAGCAGCCT CGCCTCGTTT CCATCGCCGC AAGCTTTCTT        780

CTGTCGGAGC TCCCAAAGCT CTCTCGTCTC GCCTTCTTCT CCACTCTATA TATATATAGG        840

TTCAGTTCTC TCTTCATTTT TCCATTTCTG GCTACCTTCT TAGCATCCCG ATCTCTTTCA        900

CTACTCCGCC TCGCC ATG GCC ACC GC                                         926
                Met Ala Thr
                 1

(2) INFORMATION FOR SEQ ID NO: 22:

(i) SEQUENCE CHARACTERISTICS:
        (A) LENGTH: 1450 Base pairs
        (B) TYPE: Nucleic acid
        (C) STRANDEDNESS: Double stranded
        (D) TOPOLOGY: linear (ii) MOLECULE TYPE: DNA (genomic)

(iii) HYPOTHETICAL: NO (iii) ANTI-SENSE: NO (vi) ORIGINAL SOURCE:
         (A) ORGANISM: Cuphea lanceolata (vii) IMMEDIATE SOURCE:
          (A) LIBRARY: genomic Lambda FIX II
          (B) CLONE: ClKRg12

(ix) FEATURE:
         (A) NAME/KEY: TATA-Signal
         (B) LOCATION: 1327..1343

(ix) FEATURE:
         (A) NAME/KEY: Transcription start
         (B) LOCATION: 1369

(ix) FEATURE:
         (A) NAME/KEY: Startcodon
         (B) LOCATION: 1421..1423

(ix) FEATURE:
         (A) NAME/KEY: CDS
         (B) LOCATION: 1421..1450

(xi) SEQUENCE DESCRIPTION: SEQ ID NO: 22:

CTGCAGTATT TATGAAAAAG AACTATAATG TCGGTTTCCA ATCTTACTAC CTCTTCTCGA         60

CAACCATTGA AAATGAAACT ATTAGATGCT TGTTATGGAT TTATAGTAGT TGGTATCTAA        120

TAATTCCCCA TGCACTTACC ATTGCATCGA GTCATACTGT CTGATTGGTC AAAGCCGTTT        180

GTTTTGAAGA AGTCGCATCT TGCTGTAAAG TTTTCGTTAC GGTGATTTGA TATATTTGGG        240

CTTCCTGATG CATTTTTATG AGCTTATACA TGAATATTGA CTCAATAAGA TCTGTATTGC        300

TGTGCTGTTT CGTTGAACCA AAACAGCGAT TATTTTGCCC TTCCGATTTC ATTTCCTAAC        360

AGCTAAGTTC ATCTTGATTA GGATTTGGAT AAAGCATTTG TGAAGATTCG GCCTAAGAAC        420
```

```
AACTCCAACA AACCATCCAA GGTCTCTGCC TAAGATTCAT GTTCACGCCC ATATTTTGTC    480

ACCTGGTACT TTTATTCCCG AGACAGACGA GGTTTTTGTG TGCTCATTTC TTCATGTATC    540

CTAGAGAATG ATCCTGTGAA TTGTCATTCC ATGCCGATGA GGAATCGAAG CCAATGTTTA    600

GTACTTCTAT AATAAATTCC AGCATTCGAC ATCTGATTTT GGTAGATAAA ATCTCAGGAT    660

TTTACTTACA CTAGAGGTTT GTGTTGAATC GATTCAATTC AATTATGGTA TGGGTGGGAG    720

GCATGTAATT AAGAGAACAA AGGGAGGGCA AATATGGAAA TTGGGAGCCC TGCAAATTAG    780

GAGCAGCCTT GCCTCTAGTG TGTCCATTGT TCGGTTTAAA CCGAACTGAA ATTCAAACCG    840

AAATTGGTCG GTTTGGTTCG GTTTCTCCTC GTATGAATTC GGTTTCAAAT TGAAATCGAA    900

CCGAAATATA TATTAGTTTG GTTTTCGGTT TGGCGGAATG ACAAATCGAA CCAAACCGAA    960

ATTTCAAAAT AATAAATAAA ATTATTAATT TTTAATTGAT TAATTTGATA ATTTATAAAC   1020

TTTTGTTATG AATTTAAAAA TAATTATATT ATTTTATAAA ATTATATGTA AAATTTATTT   1080

TTATATTTGT ATCGAAATTA AATTAATGTT GTTTTAATTA TTTCGGTTTA ATCCTAACCA   1140

AACCGAATTA ATTCAGTTTG AATTAGTTCG GTCCATGATA GTTCGGTTTG GGTTCGGTTC   1200

GGTTCCGCCG AAGAAAATTC GGTTTCGGTT TGGTTCGGTT TCCCCAGCTC GCCTCGTTTC   1260

CATCGCCGCA AGCTTTTTCT GTCGGAGCTC CCAAAGTTCT CTCGTCTCGC CTTCTTCTCC   1320

ACTCTCTTAT ATATATATAT ATAGCTTCAG TTCTCTCTTC ATTTTCCCAT TTCTGGCTAC   1380

CTTCTTGGCA TCCCGATCTC TTTCCCTCCT CCGCCTCGCC ATG GCC ACC GCC ACC    1435
                                             Met Ala Thr Ala Thr
                                              1               5

GCC GCC GGT TGT TCC                                                 1450
Ala Ala Gly Cys Ser
             10

(2) INFORMATION FOR SEQ ID NO: 23:

(i) SEQUENCE CHARACTERISTICS:
        (A) LENGTH: 1800 Base pairs
        (B) TYPE: Nucleic acid
        (C) STRANDEDNESS: Double stranded
        (D) TOPOLOGY: linear (ii) MOLECULE TYPE: DNA (genomic)

(iii) HYPOTHETICAL: NO (iii) ANTI-SENSE: NO (vi) ORIGINAL SOURCE:
        (A) ORGANISM: Cuphea lanceolata (vii) IMMEDIATE SOURCE:
        (A) LIBRARY: genomic Lambda FIX II
        (B) CLONE: ClERg5

(ix) FEATURE:
        (A) NAME/KEY: CAAT-Signal
        (B) LOCATION: 1335..1338

(ix) FEATURE:
        (A) NAME/KEY: TATA-Signal
        (B) LOCATION: 1362..1367

(ix) FEATURE:
        (A) NAME/KEY: Transcription start
        (B) LOCATION: 1415

(ix) FEATURE:
        (A) NAME/KEY: Startcodon
        (B) LOCATION: 1764..1766

(ix) FEATURE:
```

(A) NAME/KEY: CDS
        (B) LOCATION: 1764..1800

(xi) SEQUENCE DESCRIPTION: SEQ ID NO: 23:

CACGGGGAGA GGATTTAAAG AAAACTGGCC CCTAAAACAC AAGATTTCTA ATCGCTAGGT      60

GTTTGGTACT GTATGGAACA GTGATGAGAC TACTGAACTC GAAACTTTCG TTGTGGTTAT     120

AATGATGGAA AGATATGCAG TTGGCCGGTT TCAACTATGT TGATCAGTCC AAGCGATGAA     180

TGGAGGAAAT CATACTGAGC TGATCCCGGT TTTTTCAAGA TTCGACAGTT TGTGCATTGA     240

TGAGACACTT TCATGGAACA TCCTTCCCCA TCAACTGCTT CGATGTGTTA TCGGTATAGG     300

GTATGAGTAG ATTTCTAGTC ATGCAGCCTG TGAGCGATCA AACTCAAGAA TGAATGAACT     360

GATGAAGATC GATAAGAATG TATGATGCTC ATAATCAAAA CAAGTCGTGT CTCCAAACAT     420

ATGATGTTCA CTTATTTGAA AAATACTTAC ATCCGGGTTG ATCTCTCCAA ACCGAAGTAG     480

GAATGCATAA TATGAAAATG AATGATCTGA AATTGAAAAT ATATATAAAT AAAGTTGCAA     540

TAAATCGAGA AAACTTATCA AATGGATAGA TAGATCGACA CAACATAGAA CAAGCAAAGT     600

GTTGAATGAA TGAAAGAGAT CCATTATGCT GATTCATTAA TTCATTGTTA GTTCTAACTA     660

CGTACATGAA AAAATGAACA GTATATACAA CCTCGTAATT TTGAATGACA ATATAAGCAA     720

ATACAGATGA TAACTATACT TTAGGATCAA ATATATTAGT CCATAGGATC AAAGTATATA     780

GATAGATTGA TTGACAACTG ATTAATATTG CTAAAATATT ATTACATGAT AATAAAATT      840

ATCATTAGTG GTGAGCACAG AGCCGTAAAC CCGGACTGGC CACTACAGAA AGGTCCCTTA     900

ACACCAAAAT CAGTAAAAAA AAATAATTAA AAAAAAATAC TATTGACATA TATTATCCAA     960

ACATTTGAGC CTTATCCTTA ATTATCTACG AGGTAAATTA CTAAGACCGT ATCAGATGTT    1020

TTACGAAGTT TACATTTTTG ACTAATATTT TGAAAATAAC AAAAATAGAC ATGATTTGAA    1080

AGTAATGTAA AACATATTGG ACCAGAATGA CCAAAAATTA TTACAATTTT ATGAAACGGC    1140

ACCGTTTTTG TTACATTATT TAAAATTTGA CCCATTTTTA TCGTATTATT TTCGAATCAG    1200

ACCAAATTTT GTTATTTTCA AAATGTTGAC AAAAAAATTT TACGTTTGTG AAACATCGGC    1260

CACCAATTTT GTAATTTACC CTTATCTATA ACTGACCAAA TGGGCTTTTA TGTAACTGAT    1320

GAGCCCATTG GGCTCAATTG GTCGGCCCAT TAACATAATG CGATCGAAAC GTACAATCCG    1380

TTGTCACCAC CGAAACGCGT TTCTTGCCAG CTTCCTGCAA ACTTGAAACT CCTCTGCTCT    1440

GCTCTTCACA GCACTGAGGA TTGGTTTGGT TTCAGCGCAG AGAGGGATTG AGAGCTCTCT    1500

GGGTTTGAAA ATCTCCGCTT TTCCTCTTAA GTTCTCAGCT TTCATATCCC ATTTCCAAGG    1560

TTCCTTCTGT TTCTGCCATC CCTTTGTGTG TTTGGTTGCC AAAACATTGT ACAATGTTGC    1620

TTTTGTTTCT TGGTCTTATG TTCTGTCGGC TGAAATTTCT GCAACACTAT TTCCCAACAT    1680

TTGGGTTTGT CTGTCTCTGC TTTGTCTTAA CAAAAGTCAG CTCCTTTATG GGTAATGGCA    1740

GAAGTTGGAG CTGAGTGGTT CAG ATG GCT GCA ATG AGG CCA TGC TTG TCT       1790
                         Met Ala Ala Met Arg Pro Cys Leu Ser
                          1               5

ACT TCA TGT A                                                       1800
Thr Ser Cys
 10

(2) INFORMATION FOR SEQ ID NO: 24:

(i) SEQUENCE CHARACTERISTICS:
        (A) LENGTH: 302 Base pairs
        (B) TYPE: Nucleic acid
        (C) STRANDEDNESS: Double stranded
        (D) TOPOLOGY: linear (ii) MOLECULE TYPE: DNA (genomic)

(iii) HYPOTHETICAL: NO (iii) ANTI-SENSE: NO (vi) ORIGINAL SOURCE:
              (A) ORGANISM: Cuphea lanceolata (vii) IMMEDIATE SOURCE:
              (A) LIBRARY: genomic Lambda FIX II
              (B) CLONE: ClERg7

(xi) SEQUENCE DESCRIPTION: SEQ ID NO: 24:

```
GAGCTCGAAG GCTCCTTTGA GCAGATCCAG GAGGCTACTG CCATGGTAAA TGCGAGCAGT    60

CGTCCGCGCA AAACACAGCT TTGTTATAAG TTCACCGAGG GCGCCTGCAG TTTTGGTGAC   120

CGGTGTAAAT TTGCTCACGG AGAAGAGGAA TTAAAGAAAA CTGGTCCCTA AAACACGGAT   180

TTCTAATCGC TAGTGTTTGG TTACTGTATG GAACAGTGAT GAGACTACTG AACTCGAAAC   240

TTTCGTTGTG GTTATAGTGA TGGAAAGATA TGCAGTTGAT TTCAACTATT TGATCAGTC   300

CA                                                                 302
```

(2) INFORMATION FOR SEQ ID NO: 25:

(i) SEQUENCE CHARACTERISTICS:
              (A) LENGTH: 565 Base pairs
              (B) TYPE: Nucleic acid
              (C) STRANDEDNESS: Double stranded
              (D) TOPOLOGY: linear (ii) MOLECULE TYPE: DNA (genomic)

(iii) HYPOTHETICAL: NO (iii) ANTI-SENSE: NO (vi) ORIGINAL SOURCE:
              (A) ORGANISM: Cuphea lanceolata (vii) IMMEDIATE SOURCE:
              (A) LIBRARY: genomic Lambda FIX II
              (B) CLONE: ClERg7

(ix) FEATURE:
              (A) NAME/KEY: CAAT-Signal
              (B) LOCATION: 199..202

(ix) FEATURE:
              (A) NAME/KEY: TATA-Signal
              (B) LOCATION: 236..241

(ix) FEATURE:
              (A) NAME/KEY: Transcription start
              (B) LOCATION: 279

(xi) SEQUENCE DESCRIPTION: SEQ ID NO: 25:

```
AATATTGCTA ACATATAATT ACATGATTAA TAAATTATTA TTAGTTATTC ATTGTTATTA    60

GATAAATGCA ATTAACAAAT ATTATAATTA GTTAAATAAA TACTATTAAT ATATATTATC   120

CAAACATTTG AGCCTTATCC TTATTTATCT ATAGACTGAC CAAATGGGCT TTATGCAAC    180

TTATGAGCCT ATTGAGGTCA ATTGGCCGGC CCATTAACAT AATGCGAACG AAACGTACAA   240

TCCGCTGTCA TCACCGAAAC GCGTTTCTTG CCAGCTTCAT TCAAACTCGA AACTCCTCTG   300

CTCTTCACAG CATTGAGGAT TGGTTTGGTT TCAGAGCAGA GAGGGATTGA GAGCTCTCTG   360

GGTTTGAAAG TCTCCGCTTT GCCTCTCAAG TTCTCAGCTT TCATCTCCCA TTTCCAGGTT   420

TCTTCTGTTT CTGTCATCCC TTTGTGTGTT TGGTTTCCAA AACATTGGAC AATGTTGCTT   480
```

```
TTGTTTCTTG TTCTTATGTT CTGTCGGCTG AAATTTCTGC AACACTATTT CCCAACATTT        540

GGGTTTGTCT GTCTCTGCTT TGTCT                                             565
```

(2) INFORMATION FOR SEQ ID NO: 26:

(i) SEQUENCE CHARACTERISTICS:
        (A) LENGTH: 164 Base pairs
        (B) TYPE: Nucleic acid
        (C) STRANDEDNESS: Double stranded
        (D) TOPOLOGY: linear (ii) MOLECULE TYPE: DNA (genomic)

(iii) HYPOTHETICAL: NO (iii) ANTI-SENSE: NO (vi) ORIGINAL SOURCE:
        (A) ORGANISM: Cuphea lanceolata (vii) IMMEDIATE SOURCE:
        (A) LIBRARY: genomic Lambda FIX II
        (B) CLONE: ClERG9

(ix) FEATURE:
        (A) NAME/KEY: Transcription start
        (B) LOCATION: 1

(xi) SEQUENCE DESCRIPTION: SEQ ID NO: 26:

```
CCTCTTTGTA GACTTCTCCT CTTTACCCTG CTCAAAAATC TTGCAGTTTT ACTCGCAGAT        60

TTTTACTTCA CCGTCGGTGA TTTCAATTAG TTTTCATGGC CTTGAGCTCC AGCTTTTGTT       120

CCCTTTAGTG AGGGTTAATT TCGAGCTTGG CGTAATCATG GTCA                       164
```

(2) INFORMATION FOR SEQ ID NO: 27:

(i) SEQUENCE CHARACTERISTICS:
        (A) LENGTH: 552 Base pairs
        (B) TYPE: Nucleic acid
        (C) STRANDEDNESS: Double stranded
        (D) TOPOLOGY: linear (ii) MOLECULE TYPE: DNA (genomic)

(iii) HYPOTHETICAL: NO (iii) ANTI-SENSE: NO (vi) ORIGINAL SOURCE:
        (A) ORGANISM: Cuphea lanceolata (vii) IMMEDIATE SOURCE:
        (A) LIBRARY: genomic Lambda FIX II
        (B) CLONE: ClERG9

(ix) FEATURE:
        (A) NAME/KEY: Startcodon
        (B) LOCATION: 367..369

(ix) FEATURE:
        (A) NAME/KEY: CDS
        (B) LOCATION: 367..552

(xi) SEQUENCE DESCRIPTION: SEQ ID NO: 27:

```
TGATATTGTT TCATGAATGT GCTTCATTTA CTGTCTTTCT GATTGATCAT TATCATTTCC        60

TCATGTTTAT AGGAGTGTTC TCTGCTTGGT TTCATAGTTT TTCCATCTGA AATGTCAATG       120

TGCAGTGTGT TTGTGTTGTC TTTATGATGT TGTTAACGAA CCCATGTAGA TTCCATAAGT       180

GAAAGCAAGA CATGCACTTA TGTTTTACAA TGTCTGCTGA AAATGAGATG AAGGCTTAAG       240
```

-continued

```
TTTTATTGGG TTCATGCACT TATGTTCTAC TGATATGACA GTTTTCTAAT CTCTATGATT      300

TTTAACTGTA AAGTTTTCAT TTTGTTTAGA TTTTTACTTC ACCGTCGGTG ATTTCAATTA      360

GTTTTC ATG GCC TTG AGC TCG ACT CCT GGA ATC CAT ATG GCT GAT GCT         408
       Met Ala Leu Ser Ser Thr Pro Gly Ile His Met Ala Asp Ala
        1               5                  10

ACT AAG CCT GGG ATT TTC AAC CAA AAG TTC TAC AAG TCG AGT GTA TCA        456
Thr Lys Pro Gly Ile Phe Asn Gln Lys Phe Tyr Lys Ser Ser Val Ser
 15          20                  25                  30

GCT CTG GTT GTG GAC AGC AAA AGG GAA GCC TTA TGG ACC AAC ATT TCC        504
Ala Leu Val Val Asp Ser Lys Arg Glu Ala Leu Trp Thr Asn Ile Ser
             35                  40                  45

AGC TCA ACG CGC ATC TTC TCG AGA AAG CTC GTG ATG CAA AGC TTA TCG        552
Ser Ser Thr Arg Ile Phe Ser Arg Lys Leu Val Met Gln Ser Leu Ser
         50                  55                  60
```

(2) INFORMATION FOR SEQ ID NO: 28:

(i) SEQUENCE CHARACTERISTICS:
        (A) LENGTH: 2238 Base pairs
        (B) TYPE: Nucleic acid
        (C) STRANDEDNESS: Double stranded
        (D) TOPOLOGY: linear (ii) MOLECULE TYPE: DNA (genomic)

(iii) HYPOTHETICAL: NO (iii) ANTI-SENSE: NO (vi) ORIGINAL SOURCE:
        (A) ORGANISM: Cuphea lanceolata (vii) IMMEDIATE SOURCE:
        (A) LIBRARY: genomic Lambda FIX II
        (B) CLONE: ClERG10

(xi) SEQUENCE DESCRIPTION: SEQ ID NO: 28:

```
CGATAAGCTT GATATCGAAT TCGGAATGCA TTCCAGATCT CCATCCCCGC ATCCTTTCGG       60

TTTAAGCAGA AATAAACTCG ATGCAACAGA GAGTATTCCA ACTCCCTGCA GGACATAACA      120

AACATGTAAG GATCAAGTTT ATCTGATCAA ACATAATTTC ATGACATCTA AACCATATGA      180

TAGCACGGTG GAATGGAACA TTTACAACAG TCGACATATA TACGCCGACA AGTTAGGAGA      240

TGCTTTACCA CAATAAGGAT GACTTGGAAG ATGGCACAAG TCAAATACCG ACCCCAATAG      300

GAGTCGCTGA GGAATGCGCC GATCAGAGAG CAAAGGTAAA CCGTTCCCGT CCATTTGCTC      360

ACGCTGTTGG CTGCAGCTGC ATTGTCCTGA CCCATCACCC TAGTCAGGAA CAACACTAAG      420

TTCACCCCGA CACCGAAGAA AGTTAAGGTT GCTAAAGCTT GGTTCGCTGC AAATCATCGA      480

AAACAAAACA AGTCACTCAA CCATTCGTTT ATACATTGGA ATGGAATGGT TATACAATCC      540

ACTTAAGACT TTACCTAGCA AGATGAAGGT GCATCCCCAT CCTCCGGTTT TCTTGTCTTC      600

CCCATTGGAA TGGTTTGGCG CCGGCTTCTG ATCCTTGCTT TGCTCTAAGC TTAAGAAGCT      660

CGTCTCGAGA GCAGCATTTG CTGCACTTCC TCACCAACCT GCTACATTAC ATTTATATAC      720

ACCGAGTAAG CATATCATAT GCTATCGACA TACTATTAAT CGAGTTGCAG CTCAATGCAA      780

TGTATTGATA GATGTTATCA ATTAAACCTT CGTCTCGGTC TCACGGATGG CATTGGTAGA      840

CTCCATGGCA ACGATCGAGG GTTCTATCTG CACATATAGC CAGGAAATAC TTCAAAAACA      900

AGATATTATG ACCGACTAGT CGAAAGAAAA GATATGATGA AACGATCGAG TCATGAGTTA      960

TATATATAAA CAAACCTCCT GTGAAACTTG GTGGCACTCA AGATAGCTTG AAACTTAGTG     1020

CCACGGGAAG TAATGTCGAA CTCCGGCGAC GGAGAAGAGC CTGTGTCGAT ATACACAAAC     1080
```

-continued

```
CACCGATTGG GATATCACTA GGATTCGTCA GAATGTCACG AGAACCAATT GTCATTAATA    1140

TACGGCGGCG CGACTGGTGG ATTCAAATGC GAATGTGGTA GAACACGATC CCAACCGGAG    1200

CCAATCTCAA CTCCCCGTCG ATGTCAGTTC ATCAAGAACA ACTTGGACAA GGAACACGAA    1260

AATGAGACGA ACACCCGAAC CTCGGATAGC TTCGTATAAC GTTGTTCTTC GACGATACAC    1320

ACAAACACGT ACGATGGAAG AGAACAATGG ATTTATGGAC TCGAGAGAAT TATAGTTTGT    1380

CTCTGGAACA TCTCAAATGT TTATATAGAA AGTTATAAGA TCGGAGTAGA CTAGACTGTA    1440

TGGTCTAATT CTGTTGCATG GACCGAGTAA ATCTCCAAAT TCATTGTCAT GCTTTTACCA    1500

GTTTTTTTGT TTAATAATTA TCTGAAAAAG AAAAAAAAAG TCATAAAAAA TTATTAAATT    1560

CAAATTTTAA GGTAAACCTT TCTTTGTAAA TTAGGCTCCA TTCCTTTTTT CTCATTCCAC    1620

CTTTACTTCA TTTTTATTCC ATTATTCCAT TAAAAATATT ATATGTATTA TTGGAAAAAA    1680

CTAAAAGGGT TTTCTTAAAA TCCGTTGAAA TTAAGAATAA AAAAGGATAA ATGACATAAT    1740

TTAAATCCAC TATTATTATA GCTGATAAGT TGTGATTCAG CTCACCAAAT TACCCCAAAA    1800

TTTGATATGC AGTTGTGCTT ATACATATAT ATATATCTAC TCTTTTCTTT TCTTTTTTAC    1860

AAAGAAAATT TTAAAATTGC CGAAGAGAAG AAGTCAACTA ACATTATTAA TTATACTACT    1920

AATTTAAAAT AACTTAATTT TGTTTTTTTT TTATTATATT AGTATTTAAA GTAGTATTGT    1980

TTAAAAGTAT TCATATTTGT ATCTAGAATG ATCTTAAGGA ATATAATAAA TATTGCAAAA    2040

TAATGATACA CAATCGTGAA AAAATAAAAA AATAAAGGAA GTAAATATGG ATAATCGAAA    2100

ATTTGATGAA ACGAAGTTTT AAAATTTGGC ATAAGAAGAT AAATATTTTT TTTAATTTAT    2160

TATATGTTTA TAAAAAATGT AATATATATA TAAAATATGT GTAAAATGTT ATATGAATGA    2220

CAAAATTTGG TTGTCATT                                                  2238
```

(2) INFORMATION FOR SEQ ID NO: 29:

(i) SEQUENCE CHARACTERISTICS:
        (A) LENGTH: 484 Base pairs
        (B) TYPE: Nucleic acid
        (C) STRANDEDNESS: Double stranded
        (D) TOPOLOGY: linear (ii) MOLECULE TYPE: DNA (genomic)

(iii) HYPOTHETICAL: NO (iii) ANTI-SENSE: NO (vi) ORIGINAL SOURCE:
        (A) ORGANISM: Cuphea lanceolata (vii) IMMEDIATE SOURCE:
        (A) LIBRARY: genomic Lambda FIX II
        (B) CLONE: ClERG10

(ix) FEATURE:
        (A) NAME/KEY: Startcodon
        (B) LOCATION: 472..474

(ix) FEATURE:
        (A) NAME/KEY: CDS
        (B) LOCATION: 472..484

(xi) SEQUENCE DESCRIPTION: SEQ ID NO: 29:

```
GAAAATTCGA AGAGCCGTAT TAGGCCTCAA TTGGTCGGCC CATCGAAACG TAACAACGAA      60

ACGCGTTTTT TTGCCCAGCT TCATGCAAAC CTCGAAACTC CCTTACTCTG CTCTGTACTG     120

TTCCTTCACC GCACTCTGGA GGATTGGTTT GGTTTCAGCA CAGAGAGGGA TCGATTGGAA     180
```

```
AGCTCTCTGG GTTTGAAAAA TTCTCAGCTT TCCCCTGTCA AGTTGTCAGC TTTCATCTCC      240

AACCTCTAAG GTTTTCTTCG TTTCGTATCA TCCCTTTGTG TGTTTGCTTG CCGAGACTTG      300

TCCAATGTTG CTTTAGTTCT GTTTTTTTAA AATGTCCTGT CGGCCTGCAA ATGTCCGCAA      360

CACATTTTCC GAAGTTGTGG GATATTTATC TGTTTTTGTC TTTGTATTAA TCTTATCGAA      420

AGTCTTCTCC TTTATGGGTA TTGGCCAGTA TTTTGGAGTT GAGGGGTTCA A ATG GCT      477
                                                        Met Ala
                                                         1

GCA TTG A                                                              484
Ala Leu
```

(2) INFORMATION FOR SEQ ID NO: 30:

(i) SEQUENCE CHARACTERISTICS:
        (A) LENGTH: 315 Base pairs
        (B) TYPE: Nucleic acid
        (C) STRANDEDNESS: Double stranded
        (D) TOPOLOGY: linear (ii) MOLECULE TYPE: DNA (genomic)

(iii) HYPOTHETICAL: NO (iii) ANTI-SENSE: NO (vi) ORIGINAL SOURCE:
        (A) ORGANISM: Cuphea lanceolata (vii) IMMEDIATE SOURCE:
        (A) LIBRARY: genomic Lambda FIX II
        (B) CLONE: ClERg20

(ix) FEATURE:
        (A) NAME/KEY: CAAT-Signal
        (B) LOCATION: 159..162

(ix) FEATURE:
        (A) NAME/KEY: TATA-Signal
        (B) LOCATION: 211..215

(xi) SEQUENCE DESCRIPTION: SEQ ID NO: 30:

```
AAAAAAAAAT TACTTAATTT TTACTCTTTT TACTTGTAAA AGAGAAGGAG TTGTGAGTAT       60

GGTATGGTGT AGGCAATAAT AATTTTCCAG CCCGGCCCGT TGTGTTGTGT TGTGCGGCGT      120

CTGCGGCAAC TACAAAGTTA AGTTTGGTTC CCACCCAACA ATAACCAAAC TTCGATCTCA      180

TCGAAACCTC GCTGGTTCCT CCTTCCTTCG TATAAATCGA CACCCACCAC TGACCTGACC      240

CCTTTCCCCT TCGCCCACCC CTCTCCATCT GCCCTTTCCA AGCTCCAATC TTGCAAGATC      300

TAACTCAGGT TCAGA                                                      315
```

(2) INFORMATION FOR SEQ ID NO: 31:

(i) SEQUENCE CHARACTERISTICS:
        (A) LENGTH: 740 Base pairs
        (B) TYPE: Nucleic acid
        (C) STRANDEDNESS: Double stranded
        (D) TOPOLOGY: linear (ii) MOLECULE TYPE: DNA (genomic)

(iii) HYPOTHETICAL: NO (iii) ANTI-SENSE: NO (vi) ORIGINAL SOURCE:
        (A) ORGANISM: Cuphea lanceolata (vii) IMMEDIATE SOURCE:
        (A) LIBRARY: genomic Lambda FIX II (B) CLONE: ClERg20

(ix) FEATURE:
    (A) NAME/KEY: Startcodon
    (B) LOCATION: 598..600

(ix) FEATURE:
    (A) NAME/KEY: CDS
    (B) LOCATION: 598..740

(xi) SEQUENCE DESCRIPTION: SEQ ID NO: 31:

```
CCTCTCCTTT GATCTCTCGC TGACTGCGTA ATGTGATGTT GTTTCTGTCA AATGTGCTTC    60

ATTTACTCTT CTTTGCATGT GGGCTTGTGT TCTTTTCTCA TTTTTTTTCC CATGTTGAAG   120

TTTTTTGTGC TATGTCATGA AATGTAATAT GATCATCTTC TCAAACTTAT TGCTTGAGAA   180

ATATTCTGGG ACAGGACAGG ACAAGGAATG ATCTTGTCTT TCATTTTTAG CTTTTTGTTG   240

ATGTAGTTAT GATCATTTGG TTAAGGCTTT TGTAAATTAA AAACCCGATT TTCTTTTGCT   300

ATCTGGTTCT CTCCTATATC CTGGTTTTCC ATCTAAAGTG TCTCATTTTT TTTGTGGCGA   360

GTTACTGGGT GTTGAGGGTG TCATGTGGCT TTGTTATGTA ATGTGATGAC CTGCTGCTTG   420

ATGCCTAACA TGTTACATAC AGAGTTTGGA TCATGATGTA TGCTTTATTG ACTTACCATT   480

ATCATATCAT TACCATCTAT CTTGAGAAAT GGTGTTTTCT GTCATCAGCA ATTCCCCTGT   540

CACTCATAAT GTTATCCATT TTTTTAGGGG CTTACTAGGT GGTTTAGATT TGTGATC      597

ATG GCC TCG ACT GTG ACT TCT GGG ACC CAC TTG GCA GCT GTT AAG CCC    645
Met Ala Ser Thr Val Thr Ser Gly Thr His Leu Ala Ala Val Lys Pro
 1               5                  10                  15

GGA ATA TCT TTC CAA AAG TCT TGC AAG CCT AGT ATA GTG GCA TTG TGC    693
Gly Ile Ser Phe Gln Lys Ser Cys Lys Pro Ser Ile Val Ala Leu Cys
             20                  25                  30

ATG GAT GAT ATT AAG GAA GCC TCA TGG ACA AAG CTT ATC GAT ACC GT     740
Met Asp Asp Ile Lys Glu Ala Ser Trp Thr Lys Leu Ile Asp Thr
         35                  40                  45
```

(2) INFORMATION FOR SEQ ID NO: 32:

(i) SEQUENCE CHARACTERISTICS:
        (A) LENGTH: 1850 Base pairs
        (B) TYPE: Nucleic acid
        (C) STRANDEDNESS: Double stranded
        (D) TOPOLOGY: linear (ii) MOLECULE TYPE: DNA (genomic)

(iii) HYPOTHETICAL: NO (iii) ANTI-SENSE: NO (vi) ORIGINAL SOURCE:
        (A) ORGANISM: Cuphea lanceolata (vii) IMMEDIATE SOURCE:
        (A) LIBRARY: genomic Lambda FIX II
        (B) CLONE: ClTEg1

(ix) FEATURE:
        (A) NAME/KEY: CAAT-Signal
        (B) LOCATION: 1428..1432

(ix) FEATURE:
        (A) NAME/KEY: TATA-Signal
        (B) LOCATION: 1553..1556

(ix) FEATURE:
        (A) NAME/KEY: Transcription start
        (B) LOCATION: 1585

(ix) FEATURE:

(A) NAME/KEY: Leguminbox
    (B) LOCATION: 1642..1657

(ix) FEATURE:
    (A) NAME/KEY: Startcodon
    (B) LOCATION: 1797..1799

(ix) FEATURE:
    (A) NAME/KEY: CDS
    (B) LOCATION: 1797..1850

(xi) SEQUENCE DESCRIPTION: SEQ ID NO: 32:

```
CACCCATAAG AACCCAAAAG TCTGAAATAC AGTCAAAACC CGTAAAATTT TGATATATTA      60

TCGAATATTT TGGGATATTT GGTCCTTATG AGTGTTCGAG GGATATTTCA AATTTTACGA     120

ATATTCGGGA ATATTTCGCT ATTTAAAATT TTGCGGGATA TATTTGTAAT ATTTTATGAA     180

TTATTGAAAT ATTTTTTGAA ATTTTAAAAT ATTTTTTAAA ATTTAAATAT ATTTTAAATT     240

CTTTTAAAAA AAATATTTTT AAATATTATA AAATTAGTTT TTAAAATTTT TTAAATATTT     300

TAAAATTAGT TTTTTTTATT TTTAAAATAT TGTTGAATTT TTAAAATATT TTTTGGTTTT     360

AAAAATATAT TTAAAAGTTT TTAAATATTT TTTGAATTTT TGAAATATTG AAAAAATTTT     420

GTTGGAGATA ACCGGAGAAT TTATATATAT ATATATATAT ATATATATAT ATATATATTT     480

CGTCCATTTC GGTTAAACCA AACGTAGTTC GTAACAGAAT GATAAACGTG ATCTATGGAA     540

TGAAAGTTTA AGAGCAAACG AAGCTATTAT TTTAATTTAA AGACAAAAGT AGTGACAATT     600

TATACTTTTA AGGCAAGTTT GACCGTTAAG TCTATTTTTT ATATTGACGG GACGTGGCCA     660

TGTAATTGGT TACTTTGTCG ATGTATGCCA TGTAAGAATC ATACGCCAAC GTTCGTTAAC     720

GCCATTAACC ATACGTCATG TAAGAATATA CGTTCATTAG AAGGAACATG AAAGAAAGGG     780

TACATATTCG ATCTATATAC CGATCTATAT ACCATAGTAT TCCATATAAA TACCTTATTT     840

AGAAATACCA TATTATATAG ATATCAACGT CATTAATAAA AAATAGAAGG TTGGACCCTG     900

CATGTTACGA AATATAATGA GTTATATTTT AAATTTTGCT TTTGGATAAG TGATCCCGAA     960

AATAAGTGGA CGAAGTAATT AACCCAAATT TTTAAGCTCA AACTGATACA GTTGGATTCA    1020

TAGTTGAGGA AATGAAAACA GCTGAAGATC GCAAAGTTTC CATTGCCATA CTCATACCTC    1080

TTCATTCAGC TATGTCCCTT CCCTTGGCTT CCTATTTAAG CTGTTGTTTG TGTATGTCGC    1140

CATTTGGCCC CTCCCTCCCC TCCTCTTCAG GTATACCCAC GGCCCTCATC ATTCTCTCAC    1200

TACGTGTCTG TGTTTCCATC CCATTCCCCG CCCCGTCTCC TTTCCTTCCT TCACGGGACT    1260

TTGCTTTTGC ATACCCAGTG AACTGAACCC ACCCACCCCC AGTCACCCAG TTGTCATCTT    1320

TTTTCTGCAA AGCCTCTCTG CTTTCTTCGT TTACCGTCGT CCTGAGCCCA TAGAAAAGTT    1380

TGCCCATTTC CTCCTCGTGT TGATCGACCT CATGTCCCGT TTCTTGCCAA ATGTGCGGCC    1440

CTTCTTCTCC TGCCCACTTT CTGTTTTTTA ATGTTATGCT CCGAGCCACG TTTCTTTGAT    1500

TCTCTGTTCT CCTCACGGCG CCTTCCGGGC CACCGTCACT GTCCCCCTTC TTTATATGGC    1560

TTCCGTTTTC CTTCGTTGCT GGATATCCCA TCCCATGTTC ATCTGAGTTT GCTGTCTACC    1620

ATTTCCCTG TATGTTATTT CCATGCATGC ATGCATGTCT ATGGCTTCCT TGTAGAAATG    1680

TGTTGTGTTT TGTTATAAAG CTTCCATCTT TCCCTTCTGT TTGAATCCGA GGTTGTCGTT    1740

TTAATGCAAT TAAAGCTTCT GCTAACTGAC CCTCTTGTGT TTACAGGCGA AGAAAC       1796

ATG GTG GCT GCT GCA GCA ACT TCT GCA TTC TTC CCT GTT CCA GCC CCG      1844
Met Val Ala Ala Ala Ala Thr Ser Ala Phe Phe Pro Val Pro Ala Pro
  1               5                  10                  15

GGA ACC                                                              1850
Gly Thr
```

(2) INFORMATION FOR SEQ ID NO: 33:

(i) SEQUENCE CHARACTERISTICS:
        (A) LENGTH: 2750 Base pairs
        (B) TYPE: Nucleic acid
        (C) STRANDEDNESS: Double stranded
        (D) TOPOLOGY: linear (ii) MOLECULE TYPE: DNA (genomic)

(iii) HYPOTHETICAL: NO (iii) ANTI-SENSE: NO (vi) ORIGINAL SOURCE:
        (A) ORGANISM: Cuphea lanceolata (vii) IMMEDIATE SOURCE:
        (A) LIBRARY: genomic Lambda FIX II
        (B) CLONE: ClTEg4

(ix) FEATURE:
        (A) NAME/KEY: Startcodon
        (B) LOCATION: 2637..2639

(ix) FEATURE:
        (A) NAME/KEY: CDS
        (B) LOCATION: 2637..2750

(xi) SEQUENCE DESCRIPTION: SEQ ID NO: 33:

```
CCCTCACTAA AGGGAACAGA ATGATCTTTC TTAATCAATA CATATGCATT TGGGATATGG      60

ACGCACAACC GTCGCCCCCC GCATCCCCCT TAAGCTGAAA CTGCGATGAT CAACCGACAA     120

CCATTCGGTT TATGGCACAT TCAGCACGAC GCTCGGAGTT GTTCGCGTGG GGCCAATTCT     180

TCCTAGCGGT CGTGACTAAG ATCTTTCTCT AATTGTAGAT GGAAATATTG AATGATTCCG     240

ATCCAATTTA GAGGCTTGGA ATTAATTGAG TGCATGGCTT AGCTTTCCAC CTGCCTACTT     300

TTGTGTTTTG AGGGCAAACC CCATAAGTTT CGAACCCTCA ACTGCCGAAT GTAACACATG     360

ATATCACATT AAATTCCTCC CCTCCTAAGG ATTAAGTTAA AACCCCATCA ACCAAAACCG     420

ATTATTGATA TAAGTTATAA TGTTTGTATT TGTAGACGTC ATCGAATGAG AAGACTATAC     480

TATATATGAT CGCCAAACCA AATGCAACTC TTTTTGTTCT AACCAATAAA CTAAGCTAAG     540

AATTAAAATC CAACTTTTGT AAATCTATTT AGATCACAAG CAATCGAGAT CAGGTTTATT     600

TTGATGTTCG TATTGATTGA TATACGTCTA ACGAGACTGG ATGATGATCA ACCTCTTTTA     660

CAATCTTCTT TCTTATTTAA ATGAACGTTT TATGCAAATT GTAGTTTTAT TGATCATAGT     720

TTTTTTATAT TGGTTTAACG TTTGAAGGAA CCTACGCAAT GCAATGTGCC ATGGAGCAAT     780

CCAAATTCGA ACAATATTCA CTTTATATAT ATTTTAAGTA TTATTTAATT AATATACATA     840

CATATATATA GAAAATACAT CGACACTAAC TTTATATGCC ACATGAATCT TCTCTGACAG     900

TTGTAATAAA TACTTAAATA AATACCCCCA ATCATAAGAT CAATTACGTG AAGAATTATA     960

GAGATGGATG CATAGTAGGC CGTCCTAATA TAATTGATGC TTGAATTTTA GAGATAACTA    1020

TATGTCGTAG CATTTCAAGT AGTGTATTAT TATTAATAAT TGTAGCCCGA CATAATATTT    1080

GAATATGGTT TGAGATATTG CCGGATATAA TATCCATCGG TGCAGAGTGC AGAAGGCTCT    1140

ACAAAGGTCA AGGATTGACA GCCATCCGTA TGCAAAGCTC GATTATATTA ATCTTAAGCA    1200

TATAATTATA TTAAGATATT CAATTCGGCA AATATTGAGA ATGATGGCAG AAATTGTAGT    1260

TTATAAATTG GTAAATTAGT CTCTAGCAAG TTCCATTGAG TCCTAACTCT GAACCAATAT    1320

ATAAAAAATA TGTAATCCAC CTGCTGACAG TAACCGTATG CTAATTTATT TACCAATCTA    1380
```

-continued

```
CCTCTTATAT GTTTCGATGG CAAAAGAAAT CCATGTCACC TGATAAAAAT TTAATTTAAT        1440

GCACATATAT TATTAGCAAG GTTGAAATAT TACCCAACTT TGATATCAAC TTAATCATTT        1500

AAGAGATTAA ATAAAATAAA AAGACTTAGT CGAAATATAA ATAATATAGT ACACAATTTA        1560

TACTATTTTA TTAAGTAAAA AAAAACTAAA AAAGTATTTG TAATTGGTTT TCAATTTTTC        1620

TCTTCAATTG AAATTATTAC AAAATATATA ATTTAATAAA AATTAAATTT AAAGATAAAT        1680

TTGTAATTTT TTTAATACTT CGACTAATTT ATTTTTCGTT TAATATTAAA AATTTTAGTT        1740

GAAAAGGGCA TAATAATCCA TAAAACATTG TAAACCATTC AAATGTTTCG GGCCAGAAGA        1800

AAAGAGAAGA GAAGAGAAGA CTTGCATTGT ATAAATATGG CCCTTTCCAA ACATTGCCTG        1860

CCTGCCTGAC AGCCAACCAA TGATATGCCA TTGCCACTCT CTCCAATTCA ATTCAATTAG        1920

GAATTAGCTG TTGACAGAAA CAGCACAATT TTTTTTTCTT TAGAGAGAAA GGAGGAGAAG        1980

AAAGAAAGGA AGGAAGAAAG GAAGGCATTG TGGCCAATCT TTGAGTCCAT TCTTTTTTTT        2040

CTCACGCTCA TAATTGACCC TTTAGCCCTC TTTGCCTTCT TCAAACCCTC CTTTCCTTTC        2100

CCTTCTTCCT CTTCCTCTCT GGGAATTTTA AAGCTTTGTC CTCTTTCCCG CATTTGTTGA        2160

GCTGTTTTTG TCGCCATTTG CCTCTCCTCT TCAGGTTCGT CCCTTTCCTC TCTTCCTTTG        2220

CATGCCCCAA TTTGGGTGTT GTAGATCTGC AAAGTCCCCT CCTTTTCCCT TCTCCGCCGC        2280

CCGAGACCCT TTACGAGGTT GCCCATTCAC CCTTTTTTTT TGGTCGGGTT GTTGTCTCTT        2340

TGTTAGATCT GCCGAATGTC CCTGTCGTTT TTCATTCTTT GTTTATGTCT TCTCTGACCC        2400

TTTTTCCTGA ATGTTCTCAT CCCATCATCA AAGTTTGATT ATATTGATAT CCTGTGTGTT        2460

TTATTTGCGA TTTGTTGGTC CCCATTTCCC CTCTGCATGT CGGTTGAATT GTATCAATCT        2520

GAATGTCTCA TCTTACGGTG AAAGCTTAGA TCTTTGTCGT CTGTTTAAAT CCTGCGTTTT        2580

TCGGTTTAAT CTAATCGAAA AATGATCCTT TTTTCTGTGA TTGCAGCTCA AAAATC           2636

ATG GTG GCT ACC GCT GCA AGT TCT GCA TTC TTC CCC GTG CCA TCT GCC         2684
Met Val Ala Thr Ala Ala Ser Ser Ala Phe Phe Pro Val Pro Ser Ala
 1               5                  10                 15

GAC ACC TCC TCC AGA CCC GGA AAG CTC GGT AAT GGT CCA TCG AGC TTC         2732
Asp Thr Ser Ser Arg Pro Gly Lys Leu Gly Asn Gly Pro Ser Ser Phe
             20                  25                  30

AGC CCC CTC AAG CCC AAA                                                  2750
Ser Pro Leu Lys Pro Lys
         35
```

(2) INFORMATION FOR SEQ ID NO: 34:

(i) SEQUENCE CHARACTERISTICS:
        (A) LENGTH: 850 Base Pairs
        (B) TYPE: Nucleic acid
        (C) STRANDEDNESS: Double stranded
        (D) TOPOLOGY: linear (ii) MOLECULE TYPE: DNA (genomic)

(iii) HYPOTHETICAL: NO (iii) ANTI-SENSE: NO (vi) ORIGINAL SOURCE:
        (A) ORGANISM: Cuphea lanceolata (vii) IMMEDIATE SOURCE:
        (A) LIBRARY: genomic Lambda FIX II
        (B) CLONE: ClTEg7

(ix) FEATURE:
        (A) NAME/KEY: Startcodon
        (B) LOCATION: 783..785

(ix) FEATURE:
        (A) NAME/KEY: CDS
        (B) LOCATION: 783..850

(xi) SEQUENCE DESCRIPTION: SEQ ID NO: 34:

```
GTCGACTCGA TCCTTTCCTC CCGCTCGTAA TGACCCTTTA GCCCCCTTTG CCTTCTTCAA      60

ATCCTCCTTT CCTTTCCCTT CTTCCTCTCT GGGAAGCTTA AAGCTTTGTC CCCCACAACC     120

TCTTTCCCGC ATTCGTTGAG CTGTTTTTTT GTCGCCATTC GCCTCTCCTC TCCTCTCCTC     180

TCCTCTTCAG GTTCGCCCCT ATCTCTCTCC CTCTCTCTTG TTTCGTCTCT TTGCCGGATT     240

TGCAAACCCA TTGAATCCAG CTTGAGCCAC CCAATTGGTT ATAGATCTGC AAAGTCCCTT     300

TTTTCCCCCT TCTCCGGCGC CGGAGCCCGT TTAGAAGTTC CCCATTTTCC ATTTTTTTTT     360

CTCTTTTTTG CTGTCGGGTT GATGTCTCCT TGTTAGATCT GCCGAATGTC AGGCCTTTCC     420

TGTCGTTTTT CAATCTTCTC TGATGATTTT TGACCCAGGT TCCTTTGTTT ATGTGTTCTT     480

CTTCTTTGGA TGTTTCCTTC TTATCCCATC ATCAAAGTTT CTCTTTTTTT CCCAATGATT     540

GTTGGGTCTT CCATCTTATT TGATTATGTT GTTTCGATGA TATCCCATGT TTATCTGCGT     600

TTTTCGAGCG ATTTTTCGGT CGCCATTTCC CTGCATGTCG GTGGCATTGG ATATTCTTGT     660

AACAATCTGA ATGGCATGTG TTGTGGTGAA AGCTTGGATC TTTGCCCTCT GTTTAAATCC     720

TGCGTTTTCG GTTAATCTA ATTGAAGATT GATCATTTTT CTGTGATTGC AGTTGGAAAA     780

CA ATG GTG GCC ACC GCT GCA AGT TCT GCA TTC TTC CCC CTG CCG TCC        827
   Met Val Ala Thr Ala Ala Ser Ser Ala Phe Phe Pro Leu Pro Ser
     1               5                  10                  15

CCG GAC ACC TCC TCT AGG CCG GG                                        850
Pro Asp Thr Ser Ser Arg Pro
                 20
```

(2) INFORMATION FOR SEQ ID NO: 35:

(i) SEQUENCE CHARACTERISTICS:
       (A) LENGTH: 3350 Base pairs
       (B) TYPE: Nucleic acid
       (C) STRANDEDNESS: Double stranded
       (D) TOPOLOGY: linear (ii) MOLECULE TYPE: DNA  (genomic)

(iii) HYPOTHETICAL: NO (iii) ANTI-SENSE: NO (vi) ORIGINAL SOURCE:
       (A) ORGANISM: Cuphea lanceolata (vii) IMMEDIATE SOURCE:
       (A) LIBRARY: genomic Lambda FIX II
       (B) CLONE: ClTEg16

(ix) FEATURE:
       (A) NAME/KEY: CAAT-Signal
       (B) LOCATION: 2914..2918

(ix) FEATURE:
       (A) NAME/KEY: TATA-Signal
       (B) LOCATION: 3035..3038

(ix) FEATURE:
       (A) NAME/KEY: Transcription start
       (B) LOCATION: 3068

(ix) FEATURE:
       (A) NAME/KEY: Legumin-Box
       (B) LOCATION: 3120..3132

(ix) FEATURE:
    (A) NAME/KEY: Startcodon
    (B) LOCATION: 3291..3293

(ix) FEATURE:
    (A) NAME/KEY: CDS
    (B) LOCATION: 3291..3350

(xi) SEQUENCE DESCRIPTION: SEQ ID NO: 35:

```
GTCGACTCGA TCCACCCAAC TTAATGCAAG TGGCTCTTAA ACTCTTGCTT GTTTGCTTGC      60

TGCACTTGTC ATGCAGGTTG GTGGAATCTA TGTGAGGCTG TTCTTGAAAG ACCCCAAGTT     120

TCCTCTCCGA ATCCGAAGA GGTTCCTTGA AGGTCTCCTG GATCAGTATC TATCAGCAGT     180

GGCTGCAACA CACTATGAAA CGCAAGTGGA CCCCGAGCTT CCCTTGCTTT TATCAGCTGC     240

CCTAGTTTCT TTACTGCGAG TTCACCCTGC ACTCGCTGAT CATGTGGGTT ATCTCGGCTA     300

TGTGCCTAAG CTTGTTGCTG CTGTTGCCTA TGAAAGTAGA AGAGAAACAA TGTCCTCAGT     360

GGAGGAGAAT AATGGCCACG CAGACAGAGC AGCCTATGAG CCTGGTGATG GGTTAGAACA     420

ACCCACTCAG ACCCCACGAG AGCGAGTCCG ACTCAGCTGC TTACGTGTTT TGCATCAGCT     480

TGCAGCGAGT ACAACTTGTG CTGAAGCTAT GGCTGCAACT AGTGTTGGGA CACCACAGGT     540

AGATCTTATT TCTCGTATAT GTATATGCAT TGGTGTCTGC AATTTACATG ATTAGCTAAG     600

AAGAATGTTC CTGATATATG TCAAAGATTC TTCCGAGTTG AATGCCCTGA CAGGTTCATG     660

CATACCTTGA GTTGCAGGTT GTTCCAATTC TAATGAAAGC AATAGGCTGG CAAGGCGGAA     720

GTATATTAGC CCTTGAGACA CTGAAACGGG TTGTTGTCGC TGGAAATCGG GCTAGGGATG     780

CCCTGGTGGC TCAAGGACTC AAGTAAGTTT ATTATCGGAT ACAGGGCCTT CCATACTTCG     840

ATAGAAGTTC ATTCTCGTGT CTGATTGAGT GAAATTTTCA GGGCTGGTCT AGTTGAAGTC     900

CTTCTCGGGC TTCTTGACTG GAGAGCTGGA GGAAGACATG GACTCTGTGC TCAGATGAAG     960

TGGAACGAAT CTGAAGCATC TATTGGAAGG GTTCTTGCCA TAGAGGTCAG GATAGTTAAC    1020

TTTATTTTGT CTGCAGTATC GTGACATTGT TGCCTCACGA TATGCCGTTA ATTTTTTGGA    1080

CCGCCAACAC GGGTGTAAAA AAAGTATCT TAAATGTATG ACTCAGGTTT TACACGCATT    1140

TGCAACCGAA GGCCCATTGT ACTAAAGTGC GTGAACTGCT GGATTCGTCT GATGTAAGTT    1200

TCCTCAGCTT TCTTCTGTTG TGTCTTTATC CTGCAAACCT TTTCATGCAG TTGGCGATAT    1260

CTTAGGGCCG GCATGGTGGT TGCTCGTTGC TTGATATTAT AGTCGAGTTA GATATTGTGA    1320

TTCCAGTAAT GTAATATTTT GCACTTGCAT GTTGCCAATG GTCATAATCA GTGTTGTCTA    1380

GAGAATAGTA TTTGGATCTT TTCTAAATAT CGAGTTCTGA TATGCTAATC CTAAATCTTA    1440

TCTTTTTAAC CTCTCTTTTC TTTGATTGTT TTCAGGTTTG GGGTGCATAC AAAGACCAAA    1500

AGCACGACCT CTTCCTTCCA TCAAGTGCTC AGTCCGCTGC TGGAGTGGCT GGCTTGATTG    1560

AGAACTCGTC CTCTCGACTC ACGTATGCCC TCACAGCCCC GCCTCCCACA TCATCTCCTC    1620

CATCATACTC CAATGGCAAC GAAGATATCT TCCATCTGTA AAGACAAGTC CTGTAGTGAT    1680

ATAAAATAGC TCATTTCTGT ACAGGTTTTC GTTGGCTTTA GTCATCAGGC TTTCGAGTTT    1740

GTTCATGTTT CGTTTCTTCT TACATCATAT ATATCCTTGG GGGCGTTGCA GATTGGCATG    1800

GCGTTTTCAT TTTCAATCTC CTGATATCAA ACCTTGGAAT TTATTCCTTT GCTTCATTTT    1860

TACTCCACAC TCCACTGTAA AGATCACTCG ATCATTTATG TGTAAATTGA GGTTCTGGTT    1920

GCTTTCTGCA CATTTTTTAT ATGATCATTT TCAATGGTCA CTATTTCTTC TGTATCACTA    1980

AAGAGCCTAT ATTAATAAAT AAAGATTCAT CATCATCCCA TTCATATATT TGCTCTATTC    2040

CTATGTATAA TATTATTTTC ATTCAAAAAT TGTTTGTGAA TTCCGACTTC AATGAGATTC    2100
```

-continued

```
TAAATTTAGA ATCCCATGCC AACTAAGATA GACTCTAATG TAGATTCAAA TTATTTTGAA    2160

GACTCTAAAT TGACATTTAA AAAGTTTTTA TGGAGATGTT CTAAGCGGCA CCTTCATAAG    2220

AATTAAAAAT ACTAAATAAA TTTTTTAGTG AAAGGTCAAA TGTGCCTATA ATAAGTAAAG    2280

AAAAGTTATT ATTAATGATT TATTAAAGTA ATATCTCTTT TTTTTTTTTT TACAAGTTCT    2340

AATATTTGAA GATAAAAAAA AAAAAAAAAT TACACGTGAA AGCTGAAATG AAACTCAAAC    2400

TCCCCTGACA CCTTTCGCTT CGCACTGTCT CTGTCTTCTA AAATCCACGA GTCGGGAAAG    2460

AAAGATTCAA TTTGATTCAC TGTTGACGAA GCTGAAGATC ACAAATTTTC CAACCTCAGG    2520

ATACCCTCTT TACCTTTGCC TTTGCCTTTG CTTTTTTCTT TGCCTCTCTT CTCTTCATTC    2580

GGCTCTGTCC CTTCCCCTCG CTTCGCTTGC TTCTTCTATT GAACTGTTGT CTGTTCATGT    2640

CACCGTTTGC CCTTCCACTT CAGCTATATG GCCCTCTCTC TCTCGCACTA CGTGTCTGTC    2700

TGCGTTTCCC ATTCCCGCTT CTGTCTCCTT CCTTCACAAG ACTTCATTTG CATACACCAC    2760

TGACCTGAGC CCACCCACCC TCGTCACCCA GTGTCACTCT TCTGCAAACC CATCTGCTCT    2820

CTTCTTTTTC CCTCCACCGT AGCCCATAGA AACCACCTTC GCCCTTTTCC TCCTCGTGTT    2880

GATCGGACCT CATCATGTCT CCTTTCTTTC TGCCAAATGT CTGGCCTTTC TTCTCGCGCC    2940

CACTTTTGTT TTTAATGTTA TGCTCCCAGC CACGTTCCTT CCATTCTCTG CTCTCCTCAT    3000

GGCTCCTTCC GGGCCACCAT CAGAGTCCCC TTCTTTATAT GGCTTCCATT TTCCTTCCTT    3060

GATGGATATC CCATCTTCAT CTGTGTTTGC TGGATACCAT TTTCCCTGTA TGTTCAGTTC    3120

ATGCCATGCA TGTCTATGCC TTTCTTTCCC CTTACTACAT TTGCTGTAAC ATTGTGTTGT    3180

GTTTTGTCAT AAAGCTTTCA TCTTTCCCTT CTGTTTGAAT CCGAGGTTGT CTTTTTTATG    3240

CATTTCAAGC TTCTGATGAC TGACCCTTTT GTGCTTTCAG GCGAACAAAC ATG GTG       3296
                                                         Met Val
                                                           1

GCT GCC GCA GCA AGC TCT GCA TTC TTC TCC TTT CCA ACC CCC GGA ACC     3344
Ala Ala Ala Ala Ser Ser Ala Phe Phe Ser Phe Pro Thr Pro Gly Thr
          5                  10                  15

TCC CCC                                                              3350
Ser Pro
    20
```

KETO-ACYL-(ACP) REDUCTASE PROMOTER FROM *CUPHEA LANCEOLATA*

BACKGROUND OF THE INVENTION

On the basis of compartmentalization, the biosynthesis of fatty acids and triacylglycerides may be regarded as separate pathways of biosynthesis, but in view of the end product, as one pathway of biosynthesis. De novo biosynthesis of fatty acids takes place in plastids and is catalyzed by three enzymes or enzyme systems, namely (1) acetyl-CoA carboxylase (ACCase), (2) fatty acid synthase (FAS), and (3) acyl-[ACP] thioesterase (TE). In most organisms the end products of these reaction sequences are either palmitic acid, stearic acid or, after desaturation, oleic acid.

Fatty acid synthase consists of an enzyme complex of dissociable single enzymes with the individual enzymes acetyl-[ACP] transacylase, malonyl-[ACP] transacylase, β-ketoacyl-[ACP] synthases I, II, III, β-ketoacyl-[ACP] reductase, liydroxyacyl-[ACP] dehydratase, enoyl-[ACP] reductase and ACP=acyl carrier protein.

Then, in the so-called Kennedy pathway, triacylglyceride biosynthesis takes place from glycerol 3-phosphate and fatty acids—which are present as acyl-CoA substrates—in the cytoplasm at the endoplasmic reticulum.

The expression of genes of fatty acid biosynthesis is decisively regulated by their upstream promoters. They control the strength of the tissue-specific, development-specific or external stimulus-induced expression of the genes downstream thereto.

A large number of plant promoters, including seed-specific promoters, have been isolated and characterized during the last few years. A few examples are the HMW promoter (L. S. Robert et al., Plant Cell 1, pp. 569–578 (1989); V. Colot et al., Mol. Gen. Genet. 216, pp. 81–90 (1989)), Bäumlein et al., The Plant Journal 2, pp. 233–239, 1992; zein promoter (A. J. M. Matzke et al., Plant Mol. Biol. 14, pp. 323–332 (1990)), lectin promoter (P. Guerche et al., Mol. Gen. Genet. pp. 306–314 (1990), USP promoter (H. B äumlein et al., Mol. Gen. Genet. 225, pp. 459–467 (1991)), napin promoter (M. Stayton et al., Aust. J. Plant Physiol. 18, pp. 507–517 (1991), oleosin promoter (J. S. Keddie et al. Plant Mol. Biol. 19, pp. 443–453 (1992)) or ACP promoter (J. de Silva et al., Plant Mol. Biol. 18, pp. 1163–1172 (1992)). The extent to which they are suitable for the expression of a given gene, and the differences which they show with regard to the desired phenotype, cannot be predicted. Frequently the studies of their specificity were carried out on plant species other than the respective cultivated plants of interest. Investigated in rape and found suitable for modifications of the fatty acid metabolism were a napin promoter (J.C. Kridl et al., Seed Sci. Res. 1, pp. 209–219 (1991), D.S. Knutzon et al., Proc. Natl. Acad. Sci. 89, pp. 2624–2628 (1992), and an ACP promoter (Knutzon et al., D. E. Scherer et al., Plant. Mol. Biol. 9, pp. 127–134 (1987)).

SUMMARY OF THE INVENTION

The object of the present invention is first of all to provide promoters with which foreign genes can be expressed in plants with a high efficiency, or be brought to expression in a targeted manner in certain tissues or cell types.

This object is accomplished with the promoters and/or other regulatory elements in the 5' non-translated region according to claim 1.

The invention relates to promoters and/or other regulatory elements in the 5' non-translated region of genes which code for proteins of de novo fatty acid biosynthesis, and alleles and derivatives of these promoters.

Furthermore, the invention relates to genomic clones containing a gene which codes for a protein of de novo fatty acid biosynthesis, and alleles and derivatives of this gene, where the gene comprises the promoter, the structural gene or at least parts thereof, as well as other regulator sequences.

The invention also relates to a process for the preparation of transgenic plants, plant parts and plant products in which a promoter and/or other regulatory elements in the 5' non-translated region of genes coding for proteins of de novo fatty acid biosynthesis are coupled with a desired gene to be expressed, and then transmitted in an appropriate vector.

Furthermore the invention relates to plants, plant parts and plant products which have been prepared by the above process.

Finally the invention relates to the use of a promoter and/or other regulatory elements in the 5' non-translated region of genes which code for proteins of de novo fatty acid biosynthesis, for the preparation of plants with altered gene expression.

The subsidiary claims relate to preferred embodiments of the invention.

The figures serve to explain the invention.

DETAILED DESCRIPTION OF THE INVENTION

It is self-evident that the invention also encompasses allelic variants and derivatives of the promoters and other regulatory elements in the 5' non-translated region according to the invention, subject to the condition that these modified units exhibit the desired activity. The allelic variants and derivatives include e.g. deletions, substitutions, insertions, inversions or additions of the promoters of the invention. The same applies also to the genomic clones which contain the above-mentioned units.

The isolation of the promoters and/or other regulatory elements in the 5' non-translated region takes place via the isolation of the genes downstream thereto. The genes for the proteins of fatty acid biosynthesis are present in all plants and hence can also be isolated therefrom. Found to be a particularly suitable plant material in the present invention was rape (Brassica napus) and "Köcherblümchen" or "H öckerblümchen" with lancet-shaped leaves (Cuphea lanceolata).

Genes of fatty acid biosynthesis were isolated by means of specific hybridization probes. The latter were prepared, starting with polyA+-RNA, from approximately two-to-three- week-old immature seeds of Brassica napus or from approximately two-week-old embryos of Cuphea lanceolata, using a cDNA first-strand synthesis by polymerase chain reaction (PCR). The synthetic oligonucleotide primers required therefor will be described later on. In this way the promoters of the gene families of acetyl-CoA carboxylase (ACCase) of the acyl carrier protein (ACP), of β-ketoacyl-[ACP] synthase I (KASI), of β-ketoacyl-[ACP] reductase (KR), of enoyl-[ACP] reductase (ER), and acyl-[ACP] thioesterase (TE) were isolated.

The sizes (in terms of bp) of the PCR products for the isolation for the above-mentioned gene families are given in the following Table 1.

TABLE 1

|  |  | PCR-Product (Bp) | |
| --- | --- | --- | --- |
|  |  | Raps | Cuphea |
| Acetyl-CoA carboxylase | (ACC) | 260 | — |
| Acyl carrier protein | (ACP) | 634 | 158 |
| β-Ketoacyl[ACP] synthase I | (KASI) | 491 | 593 |
| β-Ketoacyl[ACP] reductase | (KR) | — | 325 |
| Enoyl[ACP] reductase | (ER) | — | 149 |
| Thioesterase | (TE) | — | 528 |

The promoters of the invention and other regulatory units in the 5' non-translated region are described as follows. Considered as a basis for the promoter sequences and other regulation sequences in the non-translated 5' region are the DNA sequences situated before the initiation codon, i.e. before the translation initiation of the respective structural genes. The indicated transcription initiation points describe only one of several transcription initiation points. The fact that several transcription initiation points can be determined for a gene is generally known.

1. Promoters of the genes of the acetyl-CoA carboxylase (ACC) gene family

Figure 1:
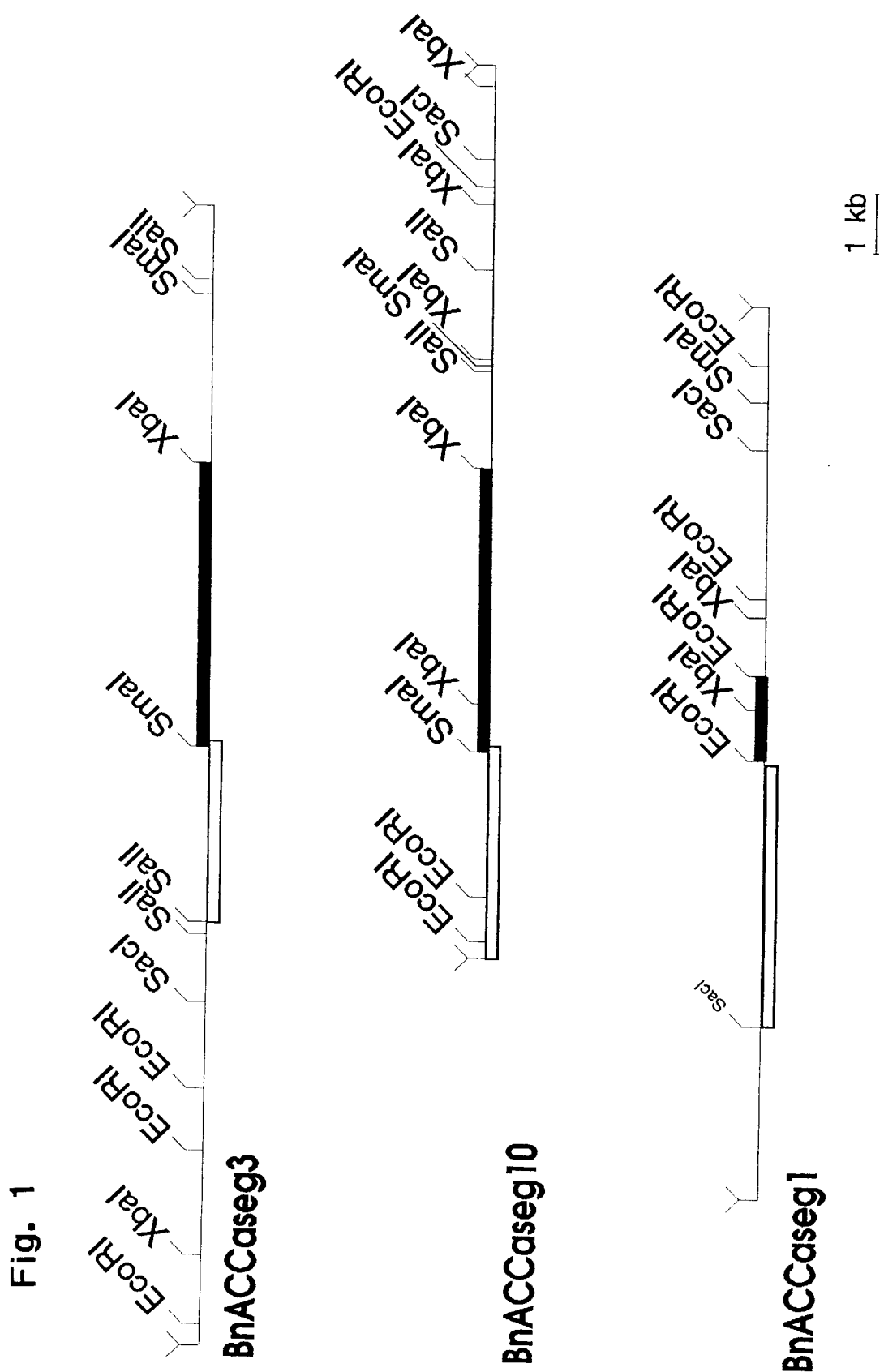
FIG. 1 shows the restriction maps of the genomic clones BnACCaseg3, BnACCaseg10 and BnACCaseg1.

Using the PCR product shown in Table 1, 15 genomic clones were isolated from a bank of genomic DNA of Brassica napus. Restriction mapping of nine clones yielded three different classes of genes, which are represented by the clones BnACCaseg3 (about 20 kb), BnACCaseg10 (15 kb), and BnACCaseg1 (15 kb). The restriction maps of these genomic clones are shown in FIG. 1. The black bars indicate the regions hybridizing with the PCR product, whereas the white bars comprise the DNA fragments which were sequenced.

Shown as SEQ NO: 1 in the sequence protocol is the DNA sequence of the promoter region and parts of the DNA sequence of the structural gene of the ACC gene from the genomic clone BnACCaseg3. This sequence comprises 2505 bp of the promoter region and about 700 bp of the structural gene. The initiation codon "ATG" of the ACCase gene is located at position 2506 of the DNA sequence. The initiation codon in position 2506 with the adjacent nucleotides is in good agreement with the plant consensus motif for translation initiation regions (G. Heidecker and J. Messing, Annual Review Plant Physiology 37, pp. 439–466 (1986), H. A. Lütcke et al., EMBO J. 6, pp. 43–48 (1987), C. P. Joshi et al., Nucl. Acids Res. 15, pp. 6643–6653 (1987)). Situated at a distance of 41 nucleotides upstream is a motif which acts as transcription start, since it comes very close to the consensus motif (CTCATCA) of Joshi, supra (position 2456). If the adenine in position 2456 based on 5'-RACE experiments is taken as the first nucleotide of an mRNA, then a possible TATA box is situated at a suitable distance of 36 nucleotides (positions 2416 to 2422). Furthermore, a CAAT box is located another 130 nucleotides away (positions 2283 to 2286). Thus the most important elements of a promoter region and 5' non-translated region are present.

Thus the DNA fragments, described below, from the other two genomic clones BnACCaseg10 and BnACCaseg1 also contain the promoter region of the ACC gene as well as parts of the structural gene. A 4450 bp DNA fragment from the BnACC1 clone (SEQ ID NO:2 in the sequence protocol) contains before the translation start with the initiation codon "ATG" (position 4089) the promoter sequence and other 5' regulatory units of the ACC gene with 4088 bp. The protein-coding region of the ACC extends to position 4421. The 5' non-translated region is interrupted by an intron and, on the basis of 5'-RACE data, begins at position 3367 (transcription initiation). This intron extends from position 3493 to 4078. The promoter sequence of the ACC gene is located in a 3350 bp DNA fragment of the BnACCaseg10 clone (SEQ ID NO:3 in the sequence protocol) before the translation start with the initiation codon at position 2611. The protein-coding sequence of the ACC extends to position 3341 and is interrupted by a non-translated region (intron), positions 2909 to 3000.

The genomic clone BnACCaseg1 and the genomic clone BnACCaseg10 were deposited on Aug. 27, 1993 under No. DSM 8480 and DSM 8481, respectively, at the DSM-Deutsche Sammlung von Mikroorganismen und Zellkulturen [DSM German Collection of Microorganisms and Cell Cultures] GmbH, Mascheroder Weg 1B, D-38124 Braunschweig.

2. Promoters of the genes of the acyl carrier protein (ACP) gene family

Figure 2:
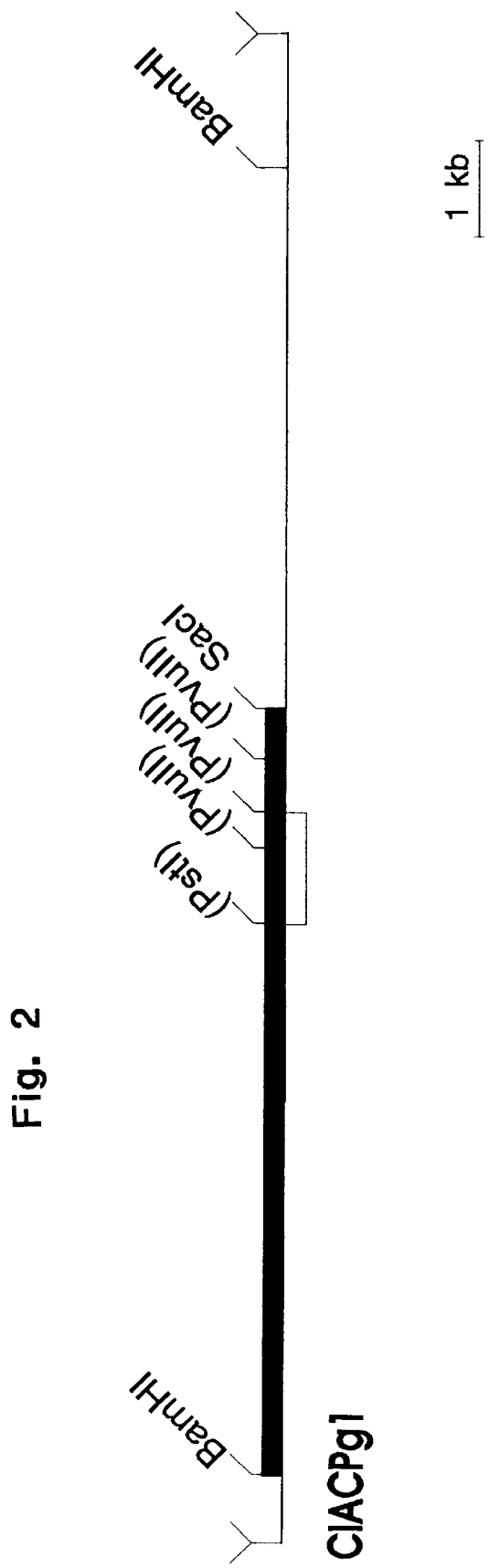
FIG. 2 shows the restriction map of the genomic clone ClACPg1.

Using the PCR product listed in Table 1, a bank of genomic DNA of Cuphea lanceolata was investigated for genes for acyl carrier protein. In this way 20 genomic clones were isolated. These clones could be classified by means of already available class-specific cDNAs as hybridization probes into three classes: classes ClACP1-1, ClACP1-2 and ClACP1-3. Of Class ClACP1-1 the genomic clone ClACPg1 was mapped. The restriction map of the genomic clone ClACPg1 can be seen in FIG. 2. The size of the insertion is 15.8 kb for ClACPg1. Within the aforementioned insertion the promoter region was identified and the corresponding restriction fragment subcloned. Thus, from ClACPg1 an 8 kb BamHI/SacI-fragment was subcloned into pUC19, whose sequencing gave the orientation of the gene. Besides the structural gene of the ACP this clone contains the promoter for this gene. The black bar in FIG. 2 shows the subcloned DNA fragment of the ClACPg1 clone and the white bar the DNA section which was sequenced.

DNA sequence analysis of a 1200 bp DNA fragment of the subcloned DNA fragment from ClACPg1 (SEQ ID NO:4 in the sequence protocol) showed that this fragment contains the promoter region of the ACP gene. It is located before the protein-coding sequence of the ACP gene which starts at position 1160 with the initiation codon "ATG". The TATA signal typical of the promoter region is located at positions 1051 to 1054.

Figure 9:
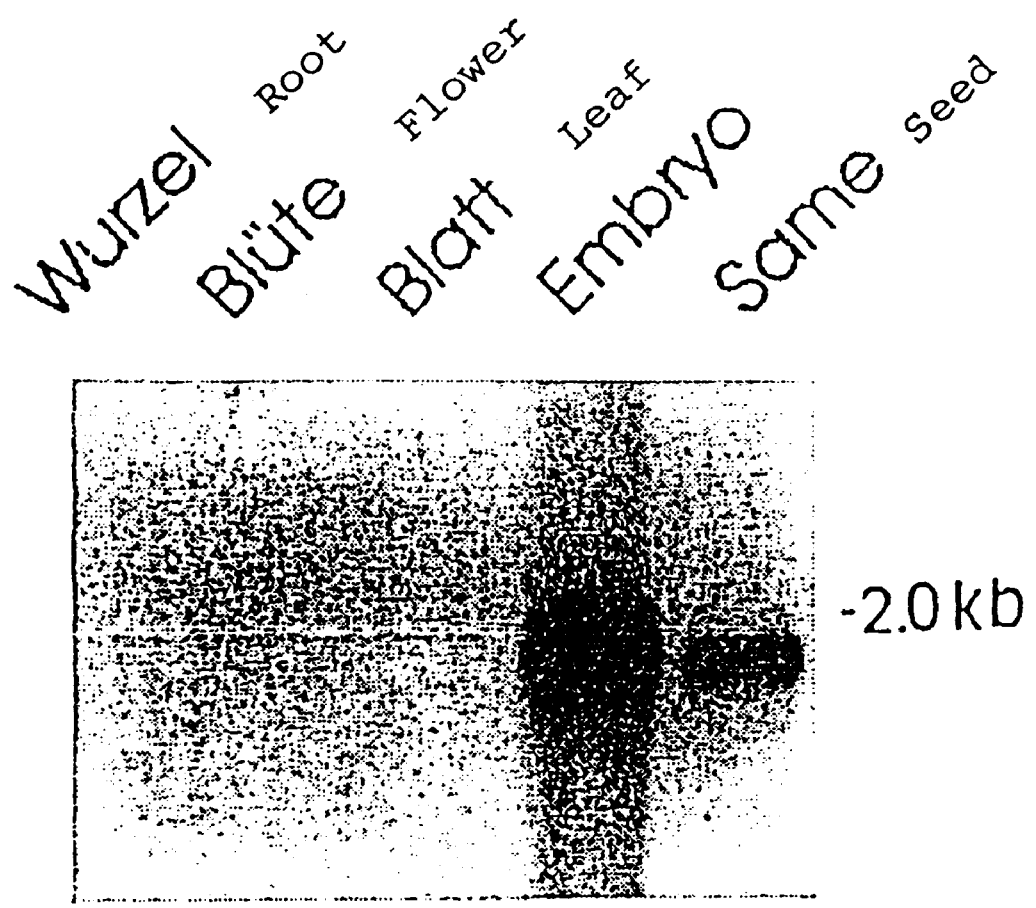
FIG. 9 shows a Northern blot with RNAs from different plant tissues, hybridized with a specific ACP CDNA probe.
Figure 10:
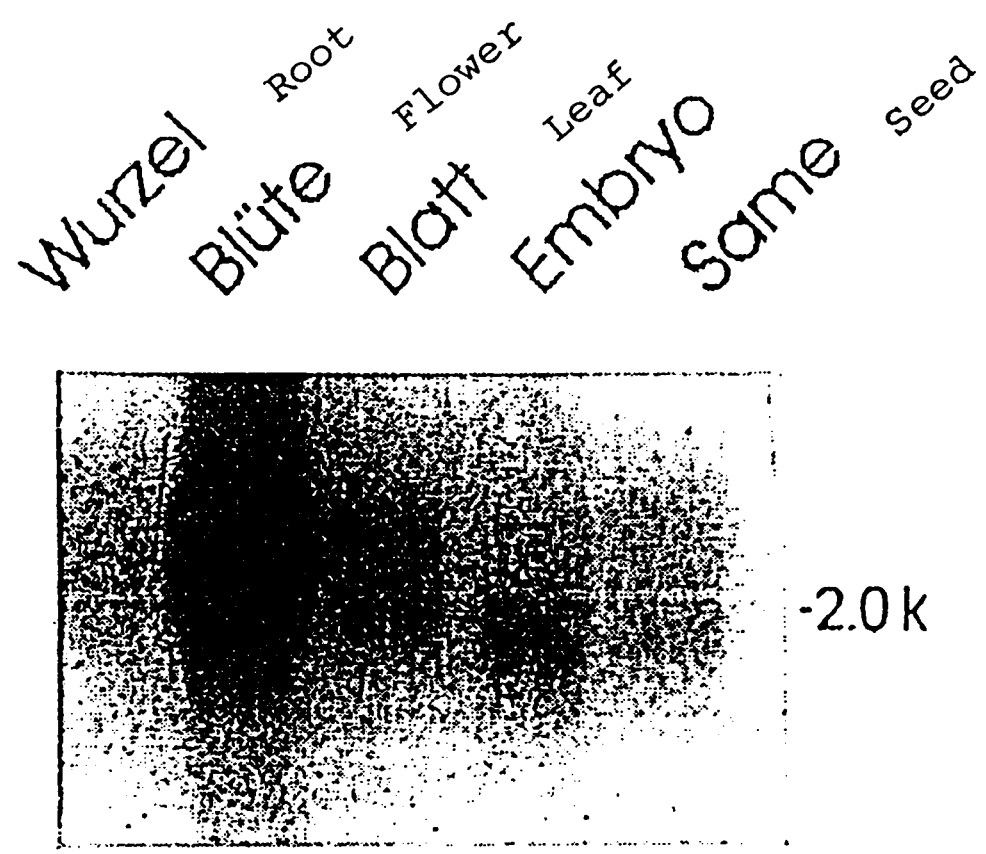
Figure 11:
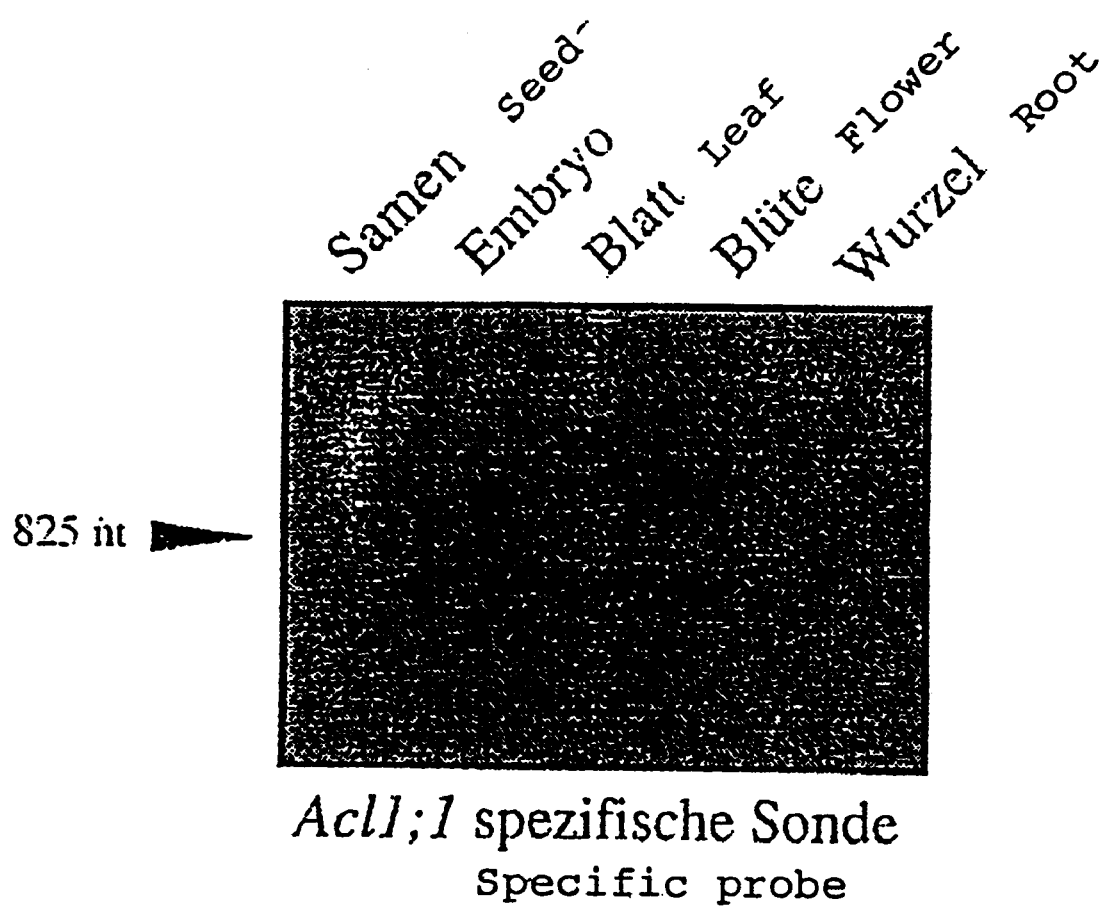

Under the control of the ACP promoter from the genomic clone ClACPg1 from Cuphea lanceolata the GUS gene was brought to expression in rape. Measurements of the β-glucuronidase expression of a fusion of the ACP promoter from ClACPg1 as a 1.2 kb PstI-PvuII-part. fragment with the GUS gene showed promoter activity in the tissues investigated (leaf, flowers and immature seeds). Northern blot analyses (see FIG. 9) showed that the corresponding ACP gene in Cuphea lanceolata is expressed in leaf, flower, root, and preferentially in the embryonal tissue.

The genomic clone ClACPg1 was deposited on Aug. 27, 1993 under No. DSM 8482 at the DSM-Deutsche Sammlung von Mikroorganismen und Zellkulturen GmbH, Mascheroder Weg 1B, D-38124 Braunschweig.

3. Promoters of the genes of the β-ketoacyl-[ACP] synthase I (KASI) gene family

By means of the PCR product listed in Table 1 nine genomic clones were isolated from a genomic DNA bank of Cuphea lanceolata, and then mapped. On the basis of restriction mapping these nine clones could be classified into six different types. A Southern blot analysis showed that in Cuphea lanceolata the β-ketoacyl-[ACP] synthase is coded by a gene family which probably consists of four classes.

Figure 3:
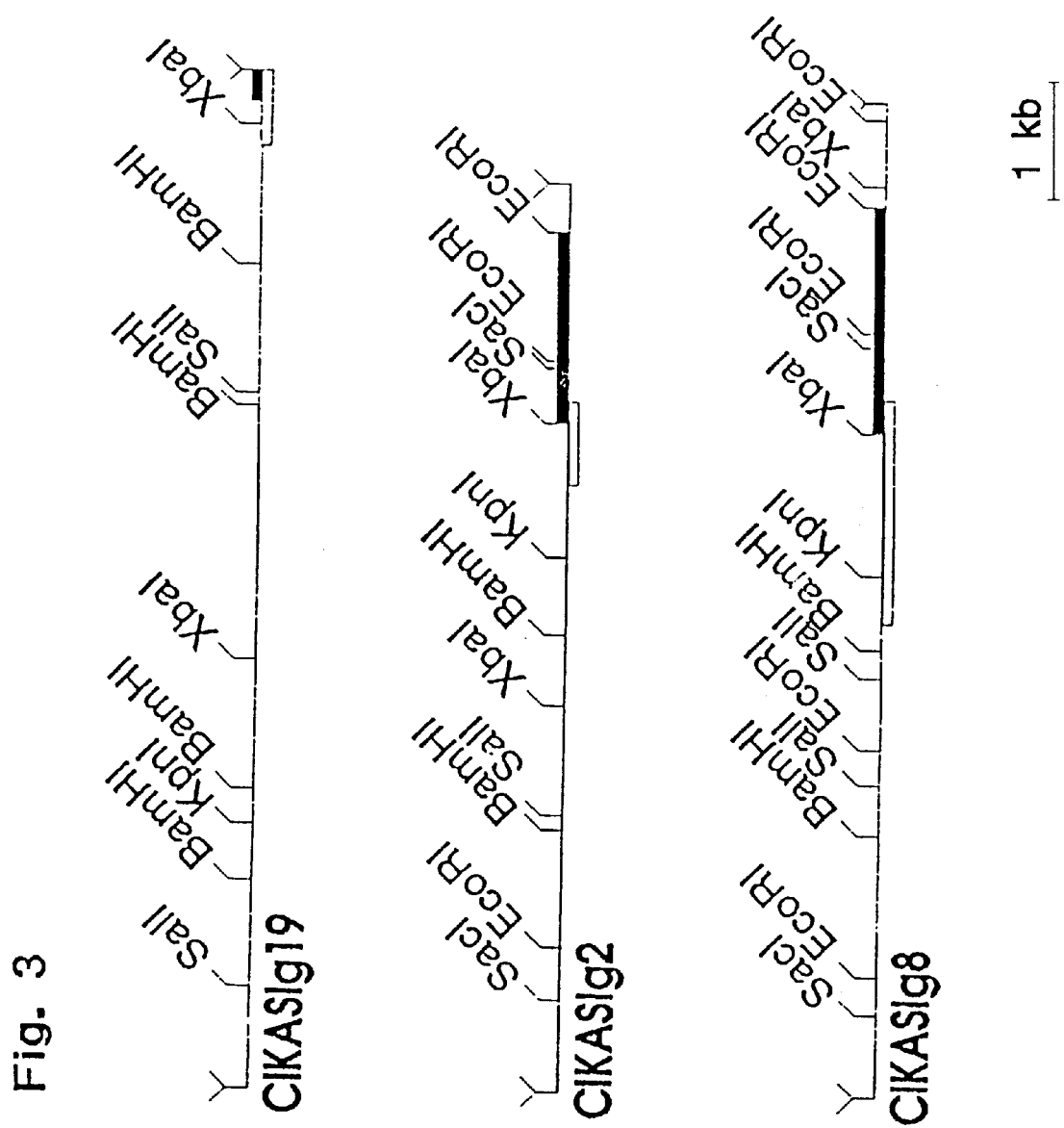
FIG. 3 shows the restriction maps of the genomic clones ClKASIg2, ClKASIg8, ClKASIg4, ClKASIg13, ClKASIg19 and ClKASIg20.

Of the isolated genomic clones the clones ClKASIg2 (12.8 kb), ClKASIg8 (14 kb), ClKASIg4 (12.3 kb), ClKASIg13 (12 kb), ClKASIg19 (19.5 kb) and ClKASIg20 (11.8 kb) were mapped. The restriction maps are shown in FIG. 3. The black bars indicate the fragments hybridizing with the probe and the white bars the fragments sequenced for the promoter region, and which originate from appropriate subclones.

Analysis of the DNA fragments of the 6 genomic clones relating to the promoter region showed that the clones together exhibit the promoter region in addition to the structural gene, or at least parts of the structural gene.

An approximately 2870 bp partial sequence from the genomic clone ClKASIg2 (SEQ ID NOS: 5, 6, 7 and 8 in the sequence protocol) shows the promoter region of the KASI gene, which ends at position 1142 (SEQ ID NO:8 in the sequence protocol), followed at position 1143 by the initiation codon "ATG". About 90 bp of this sequence were not sequenced (3 gaps).

A 2450 bp partial sequence from the genomic clone ClKASIg4 (SEQ ID NO:9 in the sequence protocol) comprises the promoter region on 1962 bp, in front of the presumable "ATG" at position 1963. A presumable intron extends from positions 2053 to 2242. The mature protein begins at position 2402.

An approximately 2894 bp partial sequence from the genomic clone ClKASIg8 (SEQ ID NOS: 10, 11, 12, 13, 14, 15, and 16 in the sequence protocol) which is interrupted by 6 non-sequenced smaller gaps (a total of about 150 bp) contains the promoter region up to position 65 (SEQ ID NO: 16 in the sequence protocol). The presumable ATG is located at position 66. This is followed by an incomplete transit peptide.

Contained in a 1350 bp partial sequence from the genomic clone ClKASIg3 (SEQ ID NO:17 in the sequence protocol) are parts of the promoter region. It contains 472 bp up to the initiation codon "ATG" (position 473 to 475). The beginning of the mature protein is at position 1075. Situated before it is the transit peptide, which is interrupted by a not precisely definable intron.

A 1141 bp fragment from the genomic clone ClKASIg19 (SEQ ID NO:18 in the sequence protocol) contains the promoter region in a 520 bp fragment. The presumable ATG is situated at position 521. The start of the mature protein is at position 956. Located before it is the transit peptide, which is interrupted by a not precisely definable intron.

Situated in a 3750 bp partial sequence from the genomic clone ClKASIg20 is the promoter region as a 3067 bp DNA fragment. The presumable "ATG" is at position 3068. The mature protein begins at position 3661. Situated before it is the transit peptide, which is interrupted by a not precisely definable intron.

For the gene from ClKASIg4 seven exons have been identified so far, which code for the mature protein. They were derived on the basis of the high homology with β-ketoacyl-[ACP] synthase I of barley. The mature protein showed a homology of 86.4% (at 77.4% identity). Due to the slight homology in the region of the transit peptide its exon/intron limits can be assumed. The structural gene extends over a length of about 2.3 kb without regulatory elements. Compared with the sequence of the genomic clone from barley (S. Kauppinen, J. Biol. Chem. 267, pp. 23999–24006 (1992)) the distribution of the exons and introns is very similar. In contrast to barley, the first exon of KASI is probably interrupted by a further intron.

Sequencing of the clone ClKASIg8 showed that the nucleotide sequence of the structural gene shows a 98% identity with ClKASIg4. The derived protein also shows a 98% identity with ClKASIg4. Also very similar to ClKASIg4 is the promoter region of ClKASIg2. The close relationship between ClKASIg2, ClKASIg4 and ClKASIg8 is clear not only on the sequence level but also on the level of the restriction maps. These three genes could be alleles which in each case show significant sequence differences in the promoter region.

On Aug. 27, 1993 the genomic clone ClKASg2 was deposited at the DSM-Deutsche Sammlung von Mikroorganismen und Zellkulturen GmbH, Mascheroder Weg 1B, D-38124 Braunschweig under No. DSM 8484, the genomic clone ClKASg8 under No. DSM 8485, the genomic clone ClKASg13 under No. DSM 8486, the genomic clone ClKASg19 under No. DSM 8487, and the genomic clone ClKASg20 under No. DSM 8488. These are the genomic clones designated in the introduction with the additional letter "I."

4. Promoters of the genes of the β-ketoacyl-[ACP] reductase (KR) gene family

The specific PCR product listed in Table 1 was used first for the isolation of cDNAs from Cuphea lanceolata. Identified, among other things, were two types of cDNAs, ClKR10 and ClKR27, which differ from one another also on the amino acid level (B. Klein et al., Plant Lipids, pp. 156–59 (1992)). The cDNAS had a size of 1295 and 1276 bp (with poly A residue), and code for an open reading frame of 326 and 320 amino acids, respectively, including the transit peptides of 69 and 63 amino acids. The proteins derived from the DNA sequence have a molecular weight of 27 kDa.

Expression of the cDNA ClKR27 from nucleotide 210 on as fusion with glutathione-S-transferase in vector pGEX-KG resulted in the purification of a fusion protein of 53 kDa. This fusion protein was used for enzyme determination for β-ketoacyl-[ACP] reductase with acetoacetyl-CoA. The measured values showed that the cDNA ClKR27 codes for an NADPH-dependent KR, which can be specifically inhibited by phenylglyoxal (Klein, supra).

Figure 4:
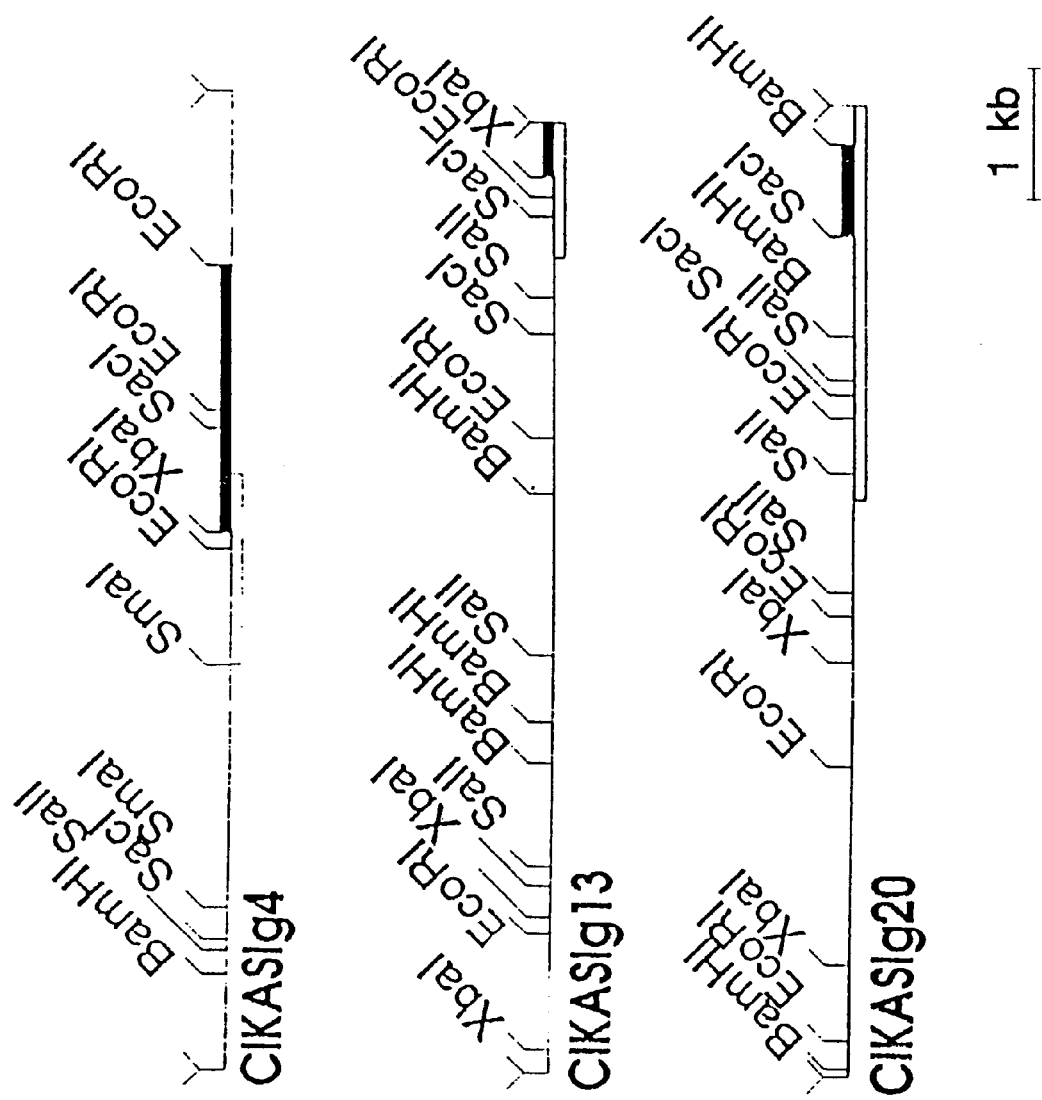
FIG. 4 shows the restriction maps of the genomic clones ClKRg2, ClKRg12 and ClKRg3.

A Southern blot analysis showed that a gene family with probably three classes of β-ketoacyl-[ACP] reductase genes exists in Cuphea lanceolata. With the cDNA ClKR27 as probe eight genomic clones were isolated from a gene bank of genomic DNA from Cuphea lanceolata, which clones could be classified into three classes. One representative of each class is shown in the restriction maps of FIG. 4. These are the restriction maps of the genomic clones ClKRg2 (13.4 kb), ClKRg12 (13.1 kb) and ClKRg3 (14 kb). The black bars indicate the regions hybridizing with the cDNA ClKR27. The white bars represent subcloned fragments. From ClKRg2 was subcloned a 4.0 kb KpnI/SmaI fragment, from ClKRg12 an 8.5 kb SalI/XbaI fragment, and from ClKRg3 an 8.7 kb SalI/XbaI fragment, and then sequenced for their identification.

The promoter region of the gene from ClKRg2 is localized on a 1570 bp DNA fragment (SEQ ID NO: 20 in the sequence protocol). With non-translated region it comprises 1511 bp. Beginning from position 1512 on with the initiation codon "ATG" is the protein-coding sequence of the KR gene. The TATA signal is located at positions 1412 to 1429, and the presumable transcription initiation at position 1445 (see above).

The promoter region of the gene from ClKRg3 is localized on a 926 bp DNA fragment (SEQ ID NO:21 in the sequence protocol). With 915 bp it comprises the region before the initiation codon "ATG" at position 916. The TATA box region is situated at positions 827 to 838, and the presumable transcription initiation is at position 864 (see above).

The complete gene is contained in ClKRgl2. It was subjected to two-stranded sequencing and the exon and intron regions were determined. The promoter region of this gene is localized on a 1450 bp DNA fragment (SEQ ID NO:22 in the sequence protocol). It is situated in a region of 1420 bp before the initiation codon "ATG" at position 1421. The TATA box region extends from positions 1327 to 1343, and the presumable transcription initiation is located at position 1369 (see above).

The promoter regions of the three KR genes show a TATA box motif, which corresponds to the consensus sequence for plants according to Joshi (1987) supra, TCACTATATATAG; ClKRg2 is in agreement in 18 positions (positions 1412–1429), ClKRg12 in 16 positions (positions 1327–1343), and ClKRg3 in 12 positions (positions 827–838). The translation initiation sequence also shows a high degree of homology with the known consensus sequence motifs (Kozak (1984), supra; Joshi (1987), supra, Lütcke et al. (1987), supra). With the exception of an approximately 500 bp insertion in the promoter ClKRg12 the promoters of genes ClKRg12 and ClKRg3 show a very high degree of agreement with one another. This insertion has numerous inverted repeats of unknown function.

5. Promoters of the genes of the enoyl-[ACP] reductase (ER) gene family

Using the PCR product listed in Table 1 as probe, eight cDNAs were isolated from Cuphea lanceolata, which, due to relatively great differences, may be classified into two classes. One cDNA, ClER18, has a length of 1533 bp and codes for a protein having a length of 391 amino acids, including 75 amino acids for a transit peptide. The mature protein has a calculated molecular weight of 33.4 kDa and shows 83.3% identical amino acids with the ER of Brassica napus. To determine the co-substrate specificity the cDNA ClER7 was fused from nucleotide 297 on with glutathione S-transferase, expressed in *E. coli*, and the appropriate fusion protein was subjected to enzyme activity determination with crotonyl-CoA as substrate and NADH or NADPH as co-substrate. On the basis of the higher activity with NADH as co-substrate it was demonstrated that the cDNA ClER7 (=Type A) codes for an NADH-dependent enoyl-[ACP] reductase.

Figure 5:
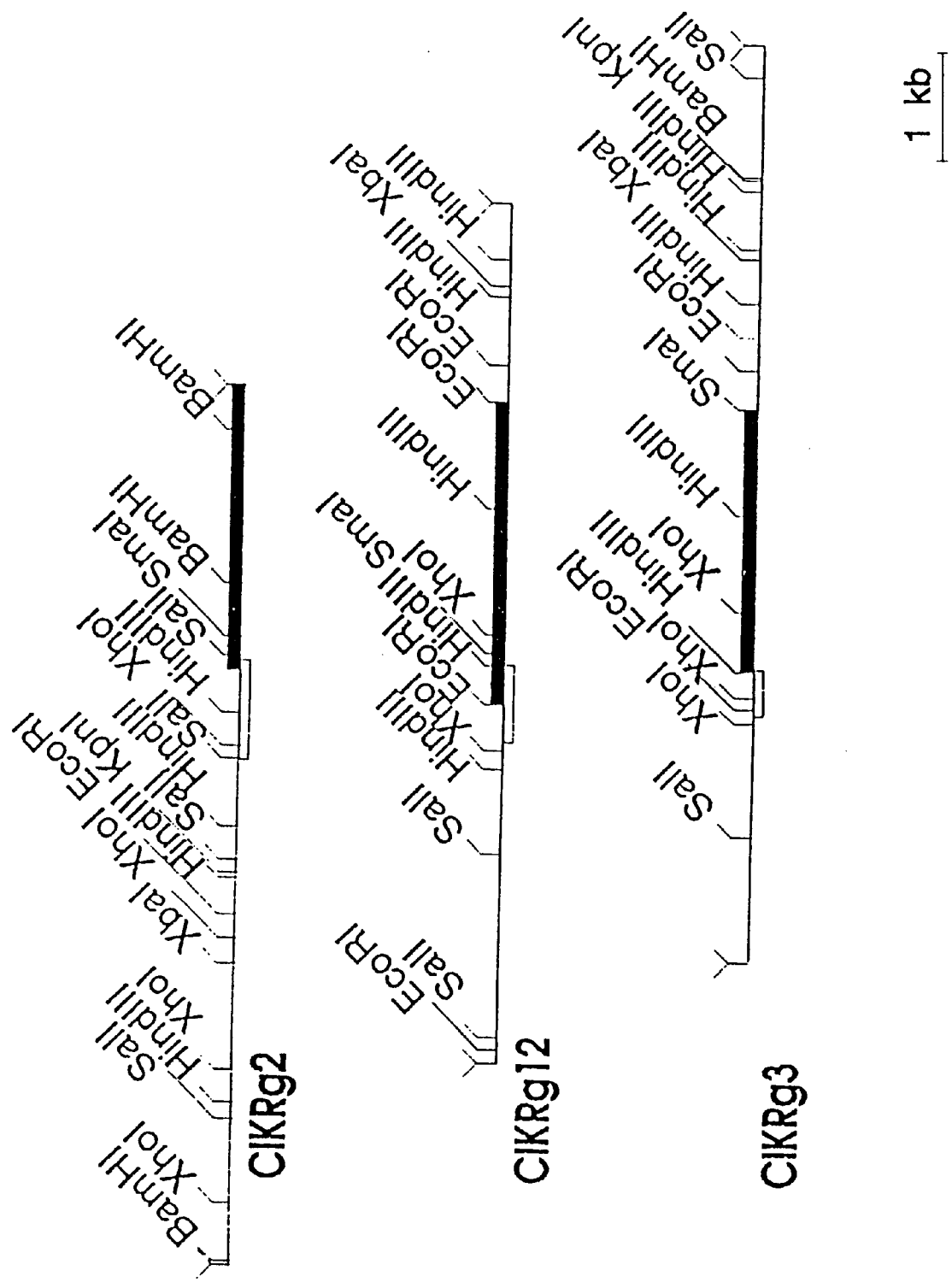
FIG. 5 shows the restriction maps of the genomic clones ClERg5, ClERg7, ClERg9, ClERg10 and ClERg20.

Using the PCR product as probe, five genomic ER clones were isolated from a λ-genomic bank of Cuphea lanceolata DNA. FIG. 5 shows the restriction maps of the genomic clones ClERg5 (12.5 kb), ClERg7 (14.4 kb), ClERg9 (16.4 kb), ClERg10 (12 kb) and ClERg20 (11.8 kb). The black bars show the region hybridizing with the probe, and the white bars the DNA sections sequenced for the promoter region.

By hybridization with specific oligonucleotides, which go back to the cDNA ClERg8, the gene ClERg9 was assigned to Type B. The sequencing of the hybridizing SalI fragment of the gene from ClERg5 showed differences in the derived amino acid sequence in comparison to the two identified classes of enoyl-[ACP] reductases, and thus constitutes the third class of ER genes (Type C).

The genomic structure of the coding region for the mature protein from ClERg5 was identified. The mature protein has 11 exons. An 1800 bp partial sequence of the gene from ClERg5 (SEQ ID NO: 23 in the sequence protocol) shows parts of the promoter with other regulatory units as a 1763 bp DNA sequence. Located in this region are the CAAT box (1335 to 1338) and TATA box (1362 to 1367). The transcription initiation is at position 1415, based on 5' RACE. An intron in the noncoding 5' region is located at positions 1560 to 1741. The translation begins with the initiation codon "ATG" at position 1764.

Fusions of the promoter region with the GUS gene showed a pronounced activity in the tissues investigated (leaf and flower) of transgenic rape plants.

Further analyses of DNA sequence regions of genomic clones ClERg7, ClERg9, ClERg10 and ClERg20 situated in the 5' region of the ER genes have indicated that they show partial regions or the whole region of the promoter sequences and sequences of other regulatory elements. An 890 bp DNA fragment from ClERg7 (SEQ ID NOS: 24 and 25 in the sequence protocol) contains the CAAT box and TATA box at positions 199 to 202 and at positions 236 to 241, respectively (SEQ ID NO: 25 in the sequence protocol). The presumable transcription initiation is situated at position 279 (see above). A non-sequenced gap of about 1200 bp exists between SEQ ID NO: 24 and SEQ ID NO: 25. At position 418 is the beginning of an intron in 5' non-translated region.

Fusions of the promoter region with the GUS gene showed a pronounced activity in the tissues investigated (leaf and flower) of transgenic rape plants.

An approximately 870 bp DNA fragment from ClERg9 (SEQ ID NOS: 26 and 27 in the sequence protocol) contains, as an approximately 690 bp DNA section, other regulatory elements in the 5' non-translated region. On the basis of 5' RACE the transcription initiation is assumed to be at position 1. An incomplete intron in the non-translated region extends up to position 329 (SEQ ID NO: I 6b in the sequence protocol). The translated region begins with the initiation codon "ATG" at position 367 (SEQ ID NO:27 in the sequence protocol). A non-sequenced region of about 160 bp is situated between SEQ ID NOS: 26 and 27.

Parts of the promoter and other regulatory elements are present on an approximately 2800 bp DNA fragment from ClERg10 (SEQ ID NOS: 28 and 29 in the sequence protocol). This region comprises about 2709 bp and contains an intron in the 5' non-translated region at positions 251 to 448 (SEQ ID NO: 29 in the sequence protocol). The translation start begins with the initiation codon "ATG" at position 472 (SEQ ID NO: 29 in the sequence protocol). A non-sequenced region of about 78 bp is present between SEQ ID NOS: 28 and 29.

A part of the promoter and other regulatory elements are contained in an approximately 1060 bp DNA fragment from ClERg20 (SEQ ID NOS: 30 and 31 in the sequence protocol). This region comprises about 912 bp and contains, apart from the CAAT box (positions 159 to 162) (SEQ ID NO: 30 in the sequence protocol) and the TATA box (positions 211 to 215) SEQ ID NO: 30 also an intron at positions 309 (SEQ ID NO: 30) to 567 (SEQ ID NO: 31). The translation begins with "ATG" at position 598 (SEQ ID NO: 31 in the sequence protocol). A short, non-sequenced region of about 5 bp is situated between SEQ ID NOS: 28 and 30.

On Aug. 27, 1993 the genomic clone ClERg7 was deposited at the DSM-Deutsche Sammlung von Mikroorganismen und Zellkulturen GmbH, Mascheroder Weg 1B, D-38124 Braunschweig under No. DSM 8489, the genomic clone ClERg9 under No.

DSM 8490, the genomic clone ClERg10 under No. DSM 8491 and the genomic clone ClERg20 under No. DSM 8492.

6. Promoters for genes of acyl-[ACP] thioesterase (TE)

By means of the PCR product listed in Table 1, corresponding cDNAs from maturing embryos of Cuphea lanceolata were used. One of the cDNAs obtained, ClTE13, has a length of 1404 bp and codes for a protein of 414 amino acids, including a transit peptide with 111 amino acids. The molecular weight of the mature protein is 34 kDa. In addition to the cDNA ClTE13, other, albeit incomplete, cDNAs were also isolated. One of these cDNAs, ClTE5, which lacks 34 amino acids of the transit peptide, was included in the comparison of derived sequences of mature proteins of the hitherto known plant TEs. The ClTE5 also shows greater similarity to medium chain-specific TEs than to long chain-specific TEs.

On screening a genomic DNA bank of Cuphea lanceolata with ClTE5 as probe, 23 genomic clones could be isolated. Restriction mapping gave four different classes of genes.

Figure 6:
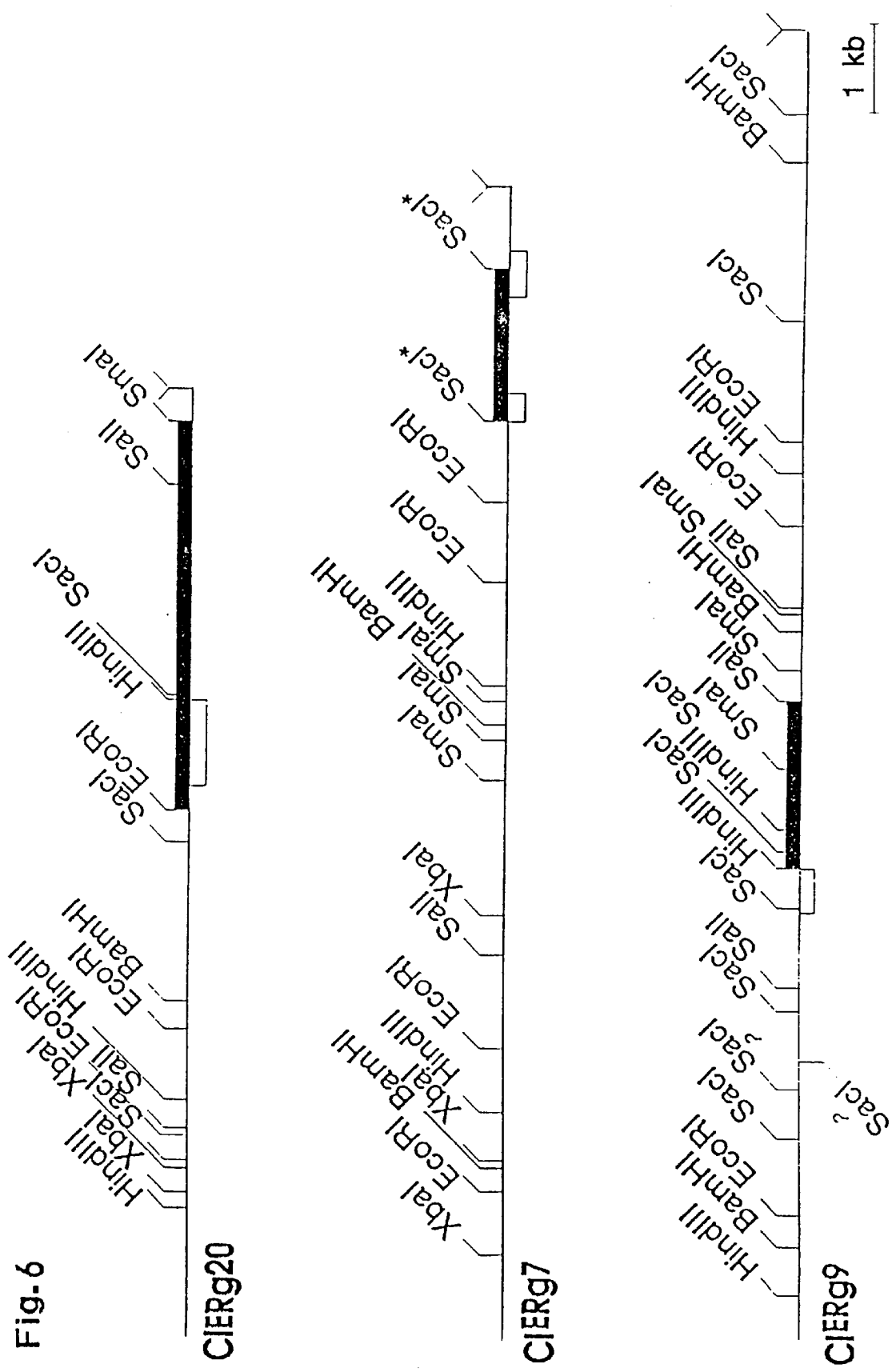
FIG. 6 shows the restriction maps of the genomic clones ClTEg1, ClTEg4, ClTEg7 and ClTEg16.

FIG. 6 shows restriction maps of the genomic clones ClTEg1, ClTEg4, ClTEg7 and ClTEg16. The black bars show the regions hybridizing with the probe, and the white bars indicate the DNA sections sequenced for the promoter region.

The clones presented contain the complete gene of Acyl-[ACP] thioesterase. A 3350 bp partial sequence of the gene with the promoter region from ClTEg16 (SEQ ID NO:35 in the sequence protocol) shows the promoter region with other regulatory elements as a DNA sequence of 3290 bp. The regions of the CAAT box and TATA box are situated at positions 2914 to 2918 and 3035 to 3038, respectively. The transcription initiation is probably at position 3068 (see above). Exon or intron regions are situated at positions 3068 to 3107 (exon I), 3108 to 3280 (intron I) and 3281 to 3350 (exon II, incomplete). The legumin box can be recognized at position 3120 to 3132. The translation begins at position 3291 with the initiation codon "ATG."

An 1850 bp partial sequence of the gene from ClTEg1 (SEQ ID NO: 32 in the sequence protocol) comprises the promoter as well as other 5'-regulatory units of the TE gene in the non-translated region, as a DNA sequence having 1796 bp. The CAAT box and TATA box are situated in the promoter region at positions 1428 to 1432 and at 1553 to 1556, respectively. The mapped transcription initiation is at position 1585. Following thereafter are exon and intron regions at positions 1585 to 1629 (exon I), 1630 to 1786 (intron I) and 1787 to 1850 (exon II, incomplete). The legumin box is located at position 1642 to 1657. The translation start begins with the initiation codon "ATG" at position 1797.

A 2750 bp partial sequence of the gene from ClTEg4 (SEQ ID NO:33 in the sequence protocol) contains the promoter and other 5'-regulatory units in the non-translated region of the TE gene as a DNA sequence with 2636 bp. An exon (exon I) ends at position 2193 and an intron (intron I) and another exon (exon II, incomplete) are located at positions 2194 to 2626 and at 2627 to 2750, respectively. The translation initiation begins with the initiation codon "ATG" at position 2637.

An 850 bp partial sequence of the gene from ClTEg7 (SEQ ID NO:34 in the sequence protocol) shows the promoter and other 5'-regulatory units in the non-translated region of the TE gene as a DNA sequence with 782 bp. Exon and also intron regions are situated at position 143 to 190 (exon I, possibly incomplete), 191 to 772 (intron I) and 773 to 850 (exon II, incomplete). The translation initiation begins with the initiation codon "ATG" at position 783.

In contrast to the 5' non-translated regions of ClTEg1 and ClTEg16 the legumin box for seed-specific expression (B äumlein et al., supra, 1992) is missing in the corresponding regions of ClTEg4 and ClTEg7. On the basis of experimental data, and in view of the specificity of the promoters, it is to be assumed that the promoters of the gene from the genomic clones ClTEg1 and ClTEg16 are seed-specific, whereas the promoters of the genes from the genomic clones ClTEg4 and ClTEg7 are of low activity in the embryo, but are all the more active in the other tissues investigated, with a maximum in the flowers and with always at least two transcript species of different lengths.

Figure 7:
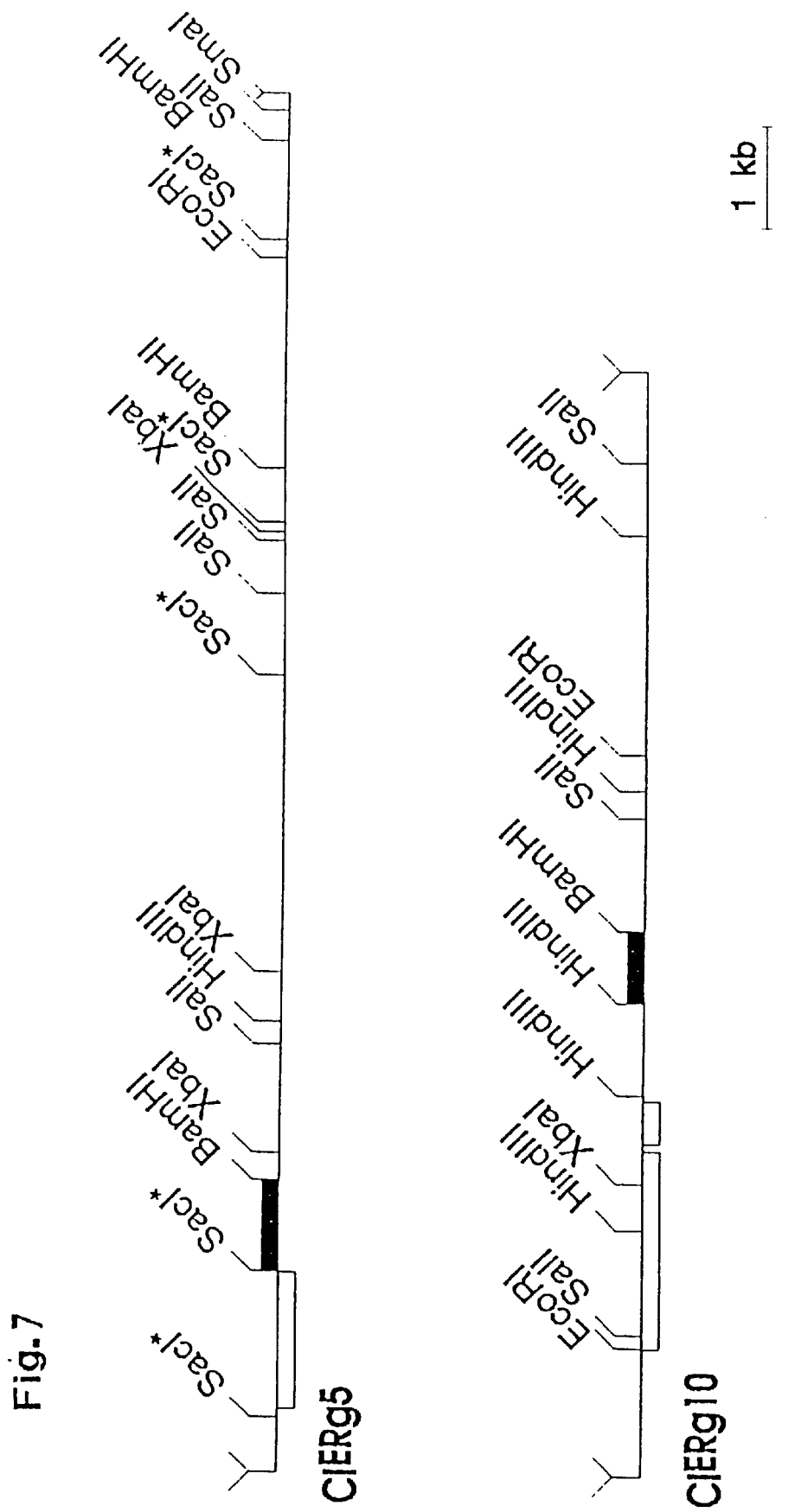
FIG. 7 shows a Northern blot with RNAs from different plant tissues, hybridized with a gene-specific probe for ClTEg1.
Figure 8:
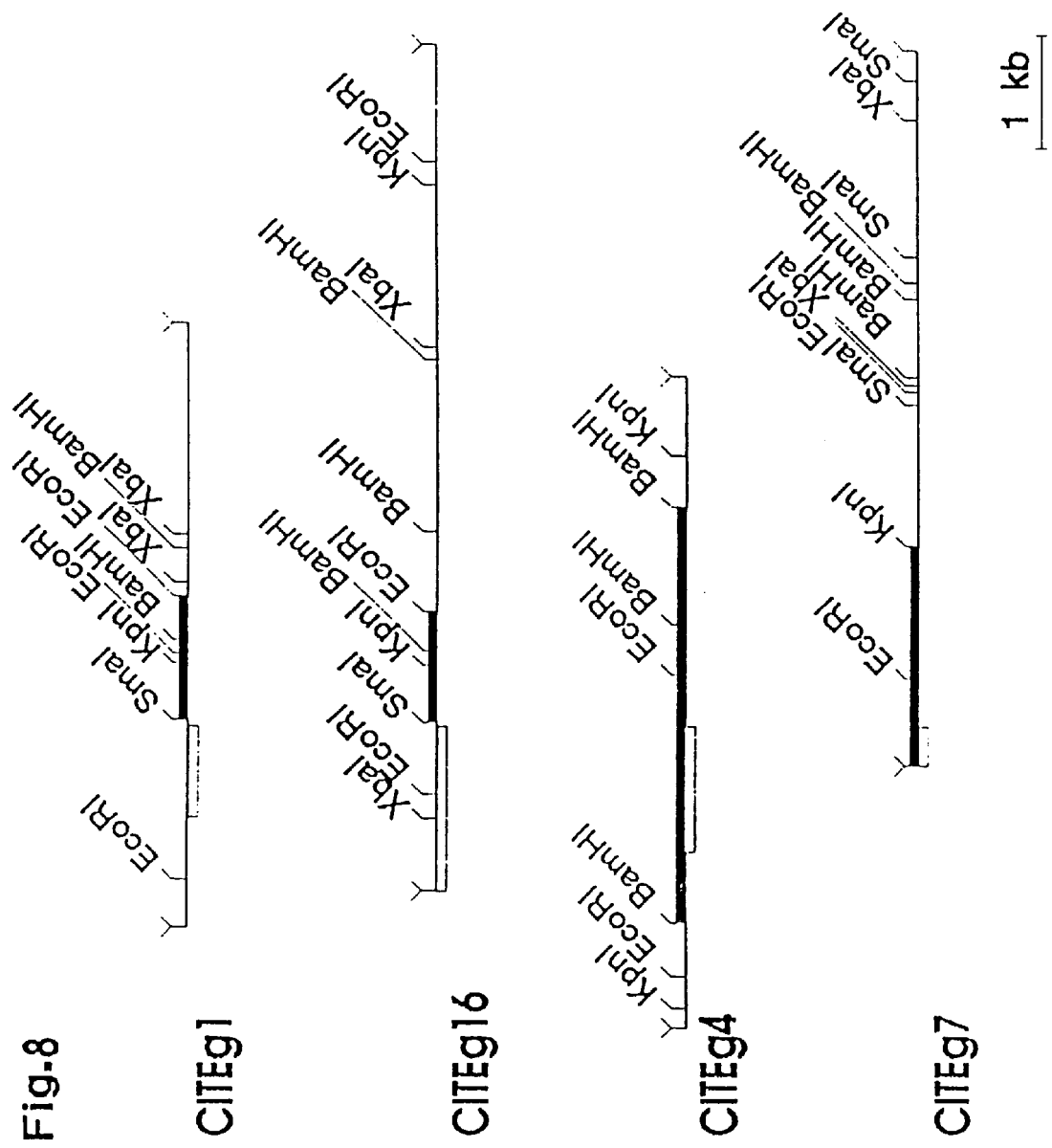
FIG. 8 shows a Northern blot with RNAs from different plant tissues, hybridized with the cDNA ClTE13 corresponding to the gene from ClTEg7.

A Northern blot analysis with PolyA$^+$-RNA from different tissues of Cuphea lanceolata shows very large amounts of specific RNA in embryos with a specific probe for the gene from ClTEg1 (see FIG. 7; the same applies to ClTEg16, not shown), whereas no specific transcript was detected in roots, leaves and flowers. By contrast, in the same experimental arrangement, very large amounts of specific RNA were detected in flowers, and always less RNA in leaves, roots, embryos and seeds when using, as a probe, the cDNA ClTE13 corresponding to the gene from ClTEg7 (see FIG. 8; the same applies to ClTEg4, not shown).

Hence the promoters of the genes from the clones ClTEg1 and ClTEg16 of the invention, in particular, are suitable e.g. for a targeted expression of chimeric genes in embryo-specific plant tissues, and the promoters of the genes from the clones ClTEg4 and ClTEg7 of the invention e.g. for an extraordinarily strong expression of chimeric genes in flowers.

On Aug. 27, 1993 the following genomic clones were deposited at the DSM-Deutsche Sammlung von Mikroorganismen und Zellkulturen GmbH, Mascheroder Weg 1B, D-38124 Braunschweig: Genomic clone ClTEg4 under No. DSM 8493, and genomic clone ClTEg7 under No. DSM 8494. The other two genomic clones ClTEg1 and ClTEg16 were deposited on August 27, 1993 at the DSM-Deutsche Sammlung von Mikroorganismen und Zellkulturen GmbH, Mascheroder Weg 1B, D-38124 Braunschweig as plasmids in which parts of these genomic clones are present, under No. DSM 8477 (pNBM99-TEgI) and DSM 8478 (pNBM99-TEg16).

On the basis of these extensive analyses it is possible to prepare clonable 5'-regulatory DNA fragments from the genomic clones which, in combination with any desired gene, effect their expression in any plant in a targeted manner. The following Table 2 shows examples of clonable fragments from the investigated genomic clones with the possible fusions.

TABLE 2

| Genomic clone | clonable 5'-regulatory fragment | Size kb | Translational fusion | Transcriptional fusion |
|---|---|---|---|---|
| BnACC1 | ClaI/BamHI | 5,6 | + | |
| BnACC3 | SalI/SmaI | 3,2 | + | |
| BnACC10 | SalI/SmaI | 3,3 | + | |
| ClACPg1 | PstI/PvuII | 1,2 | + | |
| ClKASg2 | BamHI/NcoI | 3,4 | + | |
| ClKASg4 | SmaI/NcoI | 2,4 | + | |
| ClKASg8 | BamHI/NcoI | 3,6 | + | |
| ClKASg13 | NcoI/NcoI | 3,4 | + | |
| ClKASg19 | SpeI/NcoI | 4,4 | + | |
| ClKASg20 | NcoI/NcoI | 3,3 | + | |
| ClKRg2 | SalI/NcoI | 1,5 | + | |
| ClKRg3 | PatI/NcoI | 0,9 | + | |
| ClKRg12 | PstI/NcoI | 1,4 | + | |
| ClERg5 | SalI/BamHI | 3,2 | + | |
| ClERg7 | EcoRI/SalI | 4,0 | + | |
| ClERg9 | EcoRI/HindIII | 4,4 | + | |
| ClERg10 | SalI/BamHI | 4,4 | + | |
| ClERg20 | BamHI/HindIII | 3,2 | + | |
| ClTEg1 | EcoRI/BbvI | 2,8 | | + |
| ClTEg4 | BamHI/BbvI | 3,7 | | + |
| ClTEg7 | SalI/BbvI | 0,8 | | + |
| ClTEg16 | SalI/BbvI | 3,0 | | + |

It is within the scope of knowledge of persons active in this field to use the clonable 5'-regulatory elements listed in Table 2 for the preparation of transcriptional promoter-gene fusions through suitable enzymatic manipulations. For example, cutting the sticky ends of the NcoI cleavage site of the fragments of the KR clones, e.g. with S1-nuclease, permits the preparation of transcriptional fusions.

Cloning of promoter parts and of other regulatory elements of regulatory importance, e.g. of the introns in the 5' non-translated region, may be used for constructions of chimeric promoter/expression units.

By means of genetic engineering the promoters of the invention may, with any desired gene and by forming chimeric genes, be transmitted to plants in an appropriate vector, to produce transgenic plants. The genes which come into consideration can be expressed constitutively or inductively. The induced expression can be development-specific, externally induced (biotic/abiotic) or cell-type specific. Such genes include, in particular, selectable marker genes for the transformation of plants, resistance genes (herbicide resistance, pathogen resistance), regulatory genes, and genes responsible for the seed-specific expression of genes of fatty acid metabolism, carbohydrate metabolism, amino acid metabolism, secondary metabolism, such as e.g. the polyhydroxy butyrate synthesis.

Suitable gene transfer vectors are e.g. binary vectors of the pPCV 002 series (Konz and Schell, Mol. Gen. Genet. 204, pp. 383–396 (1986)) and vectors of the pRT series for direct DNA transfer (Topfer et al., Methods in Enzymology, Ed. R. Wu, Academic Press Inc., New York, 217, pp. 66–78 (1993)), as well as viral vectors.

Thus, by means of the promoters of the invention the expression of foreign genes in transgenic plants may be regulated. This means that the gene expression can either by decisively enhanced or inhibited (by endogenic genes) or a targeted expression can be brought about in certain plant tissues.

The invention is illustrated by the following examples.
Listed first are the materials and methods used.
1. Chemicals and enzymes Unless expressly specified, chemicals and fine chemicals were obtained from Merck AG (Darmstadt), Serva Feinbiochemika GmbH & Co KG (Heidelberg), and Sigma Chemie GmbH (Deisenhofen) in analytical grade form or in a higher quality. In addition, Amersham Buchler GmbH & Co. KG (Braunschweig) supplied us with radiochemicals, Difco Laboratories (Detroit, USA) with yeast extract and Bacto-Trypton, and Biozym Diagnostik GmbH (Hameln) with FMC Seakem agarose. Restriction endonucleases and nucleic acid-modifying or synthesizing enzymes were furnished by Boehringer Mannheim GmbH (Mannheim), GIBCO-BRL (Eggenstein), New England Biolabs GmbH (Schwalbach), Perkin Elmer Cetus (Norwalk, USA), Pharmacia Biotech GmbH (Freiburg), and Stratagene GmbH (Heidelberg).

2. Purification, analysis and synthesis kits

A number of purification, analysis or synthesis methods are facilitated and speeded up by previously prepared or assembled materials accompanied by specific instructions of use, called "kits." The following list is a review of the kits employed, which were used in accordance with the manufacturers' protocols:

| | |
|---|---|
| mRNA isolation | Oligotex dT mRNA kit (Diagen) |
| cDNA synthesis | cDNA-ZAP ® II Synthesis Kit (Stratagene) |
| Plasmid purification | Quiagen Plasmid Kit (Diagen) |
| DNA fragment elution | Geneclean II ® Kit (Bio 101 Inc., La Jolla, USA) |
| DNA sequencing | $^{T7}$Sequencing Kit ® (Pharmacia) |
| Preparation of deletion clones | ExoIII/Mung Deletion Kit (Stratagene) |
| Radioactive DNA labeling | Multiprime DNA labeling system (Amersham) |
| Nonradioactive DNA labeling | DIG-Luminescent detection kit (Boehringer) |

3. Laboratory materials

Hybond N® membrane filters and Amersham, Buchler GmbH & Co. KG (Braunschweig) were used for Southern and Northern blots as well as for screening cDNA and genomic DNA banks. Moreover, X-Omat X-ray films from Kodak (Rockland, USA) were used for autoradiographies, Sephadex G 50 columns and NAP 25-columns from Pharmacia Biotech GmbH (Freiburg) for purification of radioactively labeled hybridization probes and for the purification of synthetic oligonucleotides, respectively; Dynabeads® Oligo(dT)$_{25}$ from Dynal (Oslo, Norway) for the polyA$^+$ isolations, Type 52 and Type 55 films for Model 545 plane film cassettes from Polaroid (Cambridge, USA); Quiagen-tip 100 from Diagen GmbH (Hilden) for DNA isolations, and 3MM paper from Whatman (Maidstone, USA) in the screening of cDNA and genomic DNA banks.

4. Plant material

The studies were carried out with plant material of the species Brassica napus (Cruciferae) (rape) and Cuphea lanceolata (Lythraceae) ("Kocherblumchen" or "Höckerblümchen" with lanceolate leaves). Used were the rape variety AKELA (winter rape, ++grade) and, for the C. lanceolata material, the wild type and the mutant C. lanceolata K$^-$ (Hirsinger et al., Züchtungsforsch. 85, pp. 275–286 (1980)).

5. Plasmid and vector systems

| | |
|---|---|
| Plasmids | pBluescript ® II SK(−) Strategene No. 212206) |
| | pUC18, pUC19 (C. Yanisch-Perron et al., Gene 41, pp. 103–119 (1985) |

-continued

| | | |
|---|---|---|
| | pK18 | (R. D. Pridmore, Gene 56, pp. 309–312 (1987)) |
| | pGEX-KG | (K. L. Guan et al., Anal. Biochem. 192, pp. 262–267 (1991)) |
| Lambda-phage vector | ZAP ® II | (Stratagene) |
| | FIX ® II | (Stratagene) |
| Helper phages | R408, ExAssist ® | (Stratagene) |
| Binary vectors | pGSC1706A | (Van Rompaey, unpublished) |
| | pRE1, pRE9 | (modified in the present invention from pGSC1706A) |

6. Bacterial strains a) *Escherichia coli* for clonings

| | |
|---|---|
| XL1-Blue (Stratagene) | endA1, hsdR17, supE44, thi-1, recA1, gyrA96, relA1, lac, [F'pro AB, lacl$^q$ZΔM15, Tn10(tet$^r$)] |
| DH5α (Hanahan, J. Mol. Biol. 166, pp. 557–580 (1983) | supE44, ΔlacU/69, (80lacZ M15), hsdR17, recA1, ndA1, gyrA96, Thi-1, relA1 |
| Sure ® (Stratagene) | e14 (mcrA), Δ(mcrCB-hsdSMR-mrr)171, end A1, supE44, thi-1, gyrA96, relA1, lac, recB, recJ, sbcC, umuC:Tn5(kan$^r$), uvrC, [F'proAB, lacl$^q$ZΔM15, Tn10(tet$^r$)] | b) *Escherihia coli* for lambda phage propagation

| | |
|---|---|
| K803 (H. G. Wood, Ann. Rev. Biochem. 46, pp. 385–413 (1977) | rk$^-$, mk$^-$, gal$^-$, met$^-$ |
| PLKF (Stratagene) | recA, hsdR, hsdM$^+$, rk$^-$, mk$^-$, mcrA, mcrB, gal, supE, lac, [F'proAB, lac$^q$, lacZΔM15) |
| XL1-Blue (see above) | |

The molecular biological studies were carried out by standard methods as described in J. Sambrook et al., A Laboratory Manual, 2nd Ed., Cold Spring Harbor Laboratory, Cold Spring Harbor, N.Y. (1 989).

7. cDNA and genomic DNA banks

A cDNA bank from C. lanceolata (wild type) was prepared with the aid of the cDNA ZAP® synthesis kit in accordance with the manufacturer's indications. Starting material for the synthesis of the cDNAs was mRNA from isolated, approx. two-to-three-week old, immature embryos.

The cDNA bank obtained has a size of $9.6 \times 10^5$ recombinant phages with a proportion of about 50% clones, whose insertions exceed 500 bp.

Prepared in a similar manner were the genomic DNA banks with the Lambda-FIX®II vector systems from DNA of B. napus (AKELA variety) and C. lanceolata K$^-$. The size of the genomic DNA bank of rape is $7.5 \times 10^5$ recombinant phages (with insertions of an average of 15 kb) and thus represents 3.6 times the rape genome (the size of the rape genom is $3.1 \times 10^6$ kb; C. Hallden et al., J. Mol. Evol. 25, pp. 318–323 (1987)). The size of the genomic DNA bank from C. lanceolata is $3.5 \times 10^5$ recombinant phages (with insertions of an average of about 15 kb), and thus comprises about 17 times the genome of these plants, whose genome has a size of $3 \times 10^5$ kb.

8. DNA Sequencing

To determine the sequence of a DNA fragment, cloning in pBluescript®, pK18 order pUC18 was carried out to prepare suitable subclones from which, by means of exonuclease III (Stratagene), deletion clones were prepared and sequenced according to the method of F. Sanger et al., Proc. Nat. Acad. Sci. 74, pp. 5463–5467 (1977). The DNA sequencing was done partly radioactively with the aid of the $^{T7}$Sequencing kit or with a Pharmacia Automated Laser Fluorescent A.L.F.® DNA sequencing apparatus. The sequences were analyzed by means of the computer software of the University of Wisconsin Genetics Computer Group (J. Devereux et al., Nucl. Acids Res. 12, pp. 387–395 (1984)).

9. Determination of enzyme activities

The β-glucuronidase activity was determined fluorimetrically with 4-methyl umbelliferyl glucuronide, or histochemically with 5-bromo-4-chloro-3-indolyl-β-D-glucuronic acid (X-gluc., Clontech Laboratories, Palo Alto) (R. A. Jefferson et al., EMBO J. 6, pp. 3901–3907, (1987)).

EXAMPLE 1

Preparation of specific hybridization probes a) Derivation of degenerate oligonucleotides Polymerase chain reactions (PCR) were carried out with different synthetic oligonucleotides (called primers for short). As specified below they were derived on the basis of sequence comparisons and synthesized on an Applied Biosystems DNA Synthesizer (Model 380B). A summary of the successfully used primer combinations is given in Table 3.

TABLE 3 a) Acetyl-CoA Carboxylase

```
5' Primer Nummer 3455           3'Primer Nummer 3464
    G   Y   P   V   I/              H   O   K   VA  VA  E   E   A
M I     K       A
5'    GGI IAT CCT GTI ATI-     3'   GTA GTT TTT TAI TAI CTT CTT CG
   ATA AAA GC
            C                      C  G     G   C   c c   C     c   C
                                   T
``` b) Acyl Carrier Protein

```
5' Primer Nummer 1488            3' Primer 1489
5' TCTAGACGTGAGTAACGACC ATG GCG 3' GTCTTACTTAATACTTAAGAGCTC
5' Primer Nummer 3098            3'    Primer Nummer 3240
   O   A   K   P   E   T   V   A V   M   G   L   E   E   E   F
5    CAA GCI   AAA  CCT-         3'   CAC TAC CCA AAI CTT CTT CTT AA
   GAA ACI GTI GC
       G               G     G
  G G       C     C    C
```

TABLE 3-continued

```
c) β-Ketoacyl-[ACP] Synthase 1

5' Primer Nummer 2763          3' Primer Nummer 2762
  K   R   V   V   I   T-         N   Y   S   I   S   T   A   C   A
      G       M       G
5'    AAA AGI GTI GTI ATA ACI G- 3'   TTA ATA AGI TAA AGI TGI CGI A-
GI ATG GG                        CA CG
       G                  C         G     G TC    G                G
                          T                       T d) β-Ketoacyl-[ACP] Reduktase 5' Primer Nummer 2189          3' Primer Nummer 2187
  T   A   V   0   A   W   G      N   I   N   V   N   A   I   A
5'    ACI GCI GTI GAC GCI TGG GG 3'   TTA TAA TTA CAI TTA CGI TAA CG
                  T                   G   G   G       G       G
                                          T                   t e) Enoyl-[ACP]Reduktase 5' Primer Nummer 3389          3' Primer Nummer 3391
      D   D   N   A/
  C Y     G   W   A
      M   E   I   K   K   V   Y   P
5'    GAC GAC AAC GCI TAC G-      3'     C CTC TAA TTC TTC CAI ATA GG
GI TGG GC
      T   T       T G   T                  T   G   T   T       G
                                                T f) Acyl[ACP]-Thioesterase 5' Primer Nummer 3532          3' Primer Nummer 2740
      W   N   D   L   D-
      V   N       O
5'    TGG AAC GAC CTI GAC G-   3'    T₁₈CGAAGGATCCAAGCTTGTCGACT
TI AAC GA
              T   T T     T              T
```

Glossary: Nummer = Number; Reduktase = Reductase

Acetyl-CoA carboxylase: Specific primers for acetyl CoA carboxylase were derived on the basis of a comparison of different biotin-containing proteins, among other things the ACCase from chicken and the ACCase (more exactly: biotin carboxylase) from *E. coli* in the publication of Kondo et al., Proc. Natl. Acad. Sci. 88, pp. 9730–9733 (1991) from conserved sections of the sequences. Degenerate oligonucleotides were prepared on the basis of the degenerate genetic code and the possible variability of the amino acid sequence at individual positions; i.e. different bases were incorporated at individual positions in the oligonucleotide primer, e.g. C or T resp. A or G in primer 3464. Beyond that, inosin (I) was inserted, which can interact with all nucleotides and hence should be regarded as unspecific base. The sequence of synthesized oligonucleotide primers (3455 and 3464) is based on the amino acids of regions 304 to 311 and 383 to 390 referred to the amino acid sequence of the ACCase of rat (Kondo et al., supra).

Acyl carrier protein: Degenerate oligonucleotides for the N-terminus of the acyl carrier protein from C. lanceolata were derived from N-terminal amino acid sequence data, kindly placed at our disposal by F. Spener (Münster) prior to a publication (Kopka et al., Planta 191, pp. 102–111 (1993)). This amino acid sequence, together with the conserved VMGLEEEF motif from acyl carrier proteins (e.g. Souciet and Weil 1992; Kopka et al. 1993) were used for the synthesis of the primers (3098 and 3240) mentioned in Table 2.

β-Ketoacyl-[ACP]synthase I: A comparison of β-ketoacyl-[ACP] synthase I from barley with that from *E. coli* shows only a few regions of relatively great homology (Siggaard-Anderson et al., Proc. Natl. Acad. Sci. 88, pp. 4114–4118 (1991)). For the synthesis of a specific primer pair (Table 2) an N-terminally situated sequence section was chosen (Pos. 13 to 21 for primer 2763), and the region around the cysteine which binds the inhibitor cerulenine (pos. 71 to 79 for primer 2762) (Siggaard-Anderson et al., supra). The sequence of the KAS from barley was kindly placed at our disposal by P. von Wettstein-Knowles, prior to publication (Siggaard-Anderson et al., supra).

β-Ketoacyl-[ACP] reductase: A sequence comparison of two typical fragments of β-ketoacyl-[ACP] reductase from avocado with the sequence of the nodG protein from Rhizobium meliloti in the publication of Sheldon et al., Biochem. J. 271, pp. 713–729 (1990) shows short regions of high homology between the two proteins. On the basis of the fragment-like sequences of β-ketoacyl-[ACP] reductase from avocado indicated in this publication and the homology with nodG, the two oligonucleotide primers 2189 and 2187 were synthesized (Table 2).

Enoyl-[ACP] reductase: To obtain a specific primer pair (Table 2), amino acid sequence sections of enoyl-[APC] reductase from rape (Kater et al., Plant Mol. Biol. 17, pp. 895–909 (1991)) with a relatively slightly degenerate genetic code were selected. The sequences selected correspond to amino acid positions 101 to 108 (primer 3389) and 153 to 160 (primer 3391) (Table 2).

Acyl-[ACP] thioesterase: In the publication of Voelker et al., Science 257, pp. 72–74 (1992) the first sequence of a plant acyl-[ACP] thioesterase is reproduced. Since, in addition, it is the sequence of a medium chain-specific enzyme, oligonucleotide primers were derived from some regions of the sequence whose derived DNA sequence is as little degenerated as possible, and were then synthetized. The primer 3532 (Table 2), which corresponds to amino acids 277 to 284 of the acyl-[ACP] thioesterase of *Umbellularia california*, was found in PCR reactions, in combination with the primer No. 2740 (a modified oligo-dT primer with cleavage sites for the restriction endonucleases BstBI, BamHI, HindIII and SalI), to be suitable for amplification of a specific hybridization probe.

b) Polymerase chain reaction (PCR)

Starting with 1 μg of polyA$^+$-RNA a cDNa synthesis was carried out with reverse transcriptase (Boehringer Mannheim GmbH from avian myeloblastosis virus (AMV) for 30 minutes at 37° C. To this end the respective 3'-oligonucleotide primers shown in Table 3 were used for the synthesis of a specific hybridization probe. After inactivation of the reverse transcriptase by heating at 95° C. for 5 minutes, the PCR reaction was performed in the same reaction batch with 50 pmol end concentration per primer (see Table 3) and four units of Ampli-Tag® polymerase (Perkin Elmer Cetus). The reactions were carried out under the following conditions: a) Buffer conditions: 10 mM Tris-HCl, pH 8.0; 50 mM KCl; 1.5 mM MgCl$_2$; 0.01% gelatin, and 5 mM dNTPs; b) Reaction time and reaction temperatures: 3 minutes at 92° C. for first-time denaturing, then 25 to 30 temperature cycles consisting of 2 minutes at 92° C. for denaturing, 2 minutes at the temperature given in Table 4 for annealing the oligonucleotides, and 2.5 minutes at 72° C. for amplification of the DNA, and finally 7 minutes at 72° C. to achieve complete synthesis of the last products of synthesis.

TABLE 4

| Oligonucleotide specific for | | 5' primer No. | 3' primer No. | Annealing at |
|---|---|---|---|---|
| Acetyl-CoA carboxylate | (ACC) | 3455 | 3464 | 51° C. |
| Acyl carrier protein, rape | (ACP) | 1488 | 1489 | 48° C. |
| Acyl carrier protein, Cuphea | (ACP) | 3098 | 3240 | 48° C. |
| β-Ketoacyl[ACP] synthase I | (KASI) | 2763 | 2762 | 48° C. |
| β-Ketoacyl[ACP] reductase | (KR) | 2189 | 2187 | 48° C. |
| Enoyl[ACP] reductase | (ER) | 3389 | 3391 | 49° C. |
| Thioesterase | (TE) | 3532 | 2740 | 50° C. |

Residual single-stranded DNA of the PCR products was filled in with Klenow polymerase and then phosphorylated with polynucleotide kinase (Sambrook et al., supra). Purification of the PCR products was carried out by standard protocols according to Sambrook et al., supra, using agarose gel electrophoresis, gel elution, extraction with phenol/chloroform and subsequent precipitation with isopropanol. The DNA purified in this manner was ligated in pBluescript®-vector-DNA cleaved in SmaI, and sequenced.

EXAMPLE 2

Preparation of promoters

The PCR products described in Example 1 were used for isolation of the genomic clones. This was done either directly by using the PCR product as a probe for screening a bank of genomic DNA, or via a cDNA as probe, which was employed by using the PCR product as a suitable probe for screening cDNA banks. The genomic clones found were sequenced in the usual manner and characterized with a view to the promoter regions.

If, by any chance, some molecular biological operations were not adequately described herein, they were carried out by standard methods, as described in Sambrook et al., A Laboratory Manual, 2nd edition (1989).

DEPOSIT INFORMATION

The biological materials referenced in this application by deposit number were deposited on Aug. 27, 1993 with the Deutch Sammlung von Mikroorganismen und Zellkulturen GmbH, located at Mascheroder Weg 1 B, D-38124 Braunschweig, Germany, in compliance with the Budapest Treaty on the International Recognition of the Deposit of Microorganisms for the Purpose of Patent Procedure and are as follows:

| | |
|---|---|
| BnACCaseg1 as Deposit Number | DSM 8480 |
| BnACaseg10 as Deposit Number | DSM 8481 |
| C1ACPg1 as Deposit Number | DSM 8482 |
| C1KASg2 as Deposit Number | DSM 8484 |
| C1KASg8 as Deposit Number | DSM 8485 |
| C1KASg13 as Deposit Number | DSM 8486 |
| C1KASg19 as Deposit Number | DSM 8487 |
| C1KASg20 as Deposit Number | DSM 8488 |
| C1ERg7 as Deposit Number | DSM 8489 |
| C1Erg9 as Deposit Number | DSM 8490 |
| C1Erg10 as Deposit Number | DSM 8491 |
| C1Erg20 as Deposit Number | DSM 8492 |
| C1TEg4 as Deposit Number | DSM 8493 |
| C1TEg7 as Deposit Number | DSM 8494 |
| pNBM99-TEg1 as Deposit Number | DSM 8477 |
| pNBM99-TEg16 as Deposit Number | DSM 8478 |

What is claimed is:

1. An isolated promoter from the 5' non-translated region of a gene which belongs to the β-ketoacyl-(ACP) reductase gene family from Cuphea Lanceolata.

2. The isolated promoter of claim 1 as defined in SEQ ID NO:20.

3. The isolated promoter of claim 1 as defined in SEQ ID NO:21.

4. The isolated promoter of claim 1 as defined in SEQ ID NO:22.

5. A method of producing a transformed plant cell, said method comprising the steps of: (i) operably linking the isolated promoter of claim 1 with the coding region of a desired gene to be expressed, and (ii) transferring by means of gene technology the fusion of promoter and coding region of step (i) into a cell of a plant to form a transformed plant cell, wherein said desired gene is expressed under control of said promoter.

6. The method of claim 5, further comprising the step of regenerating transformed plants or transformed plant parts from the transformed plant cell.

7. Transformed plants or transformed plant parts produced by the method of claim 5.

8. An isolated nucleotide sequence comprising a promoter from the 5' non-translated region of a β-ketoacyl-(ACP) reductase gene from Cuphea Lanceolata as defined in SEQ ID NO:20.

9. An isolated nucleotide sequence comprising a promoter from the 5' non-translated region of a β-ketoacyl-(ACP) reductase gene from Cuphea Lanceolata as defined in SEQ ID NO:21.

10. An isolated nucleotide sequence comprising a promoter from the 5' non-translated region of a β-ketoacyl-(ACP) reductase gene from Cuphea Lanceolata as defined in SEQ ID NO:22.

* * * * *